US010391201B2

(12) United States Patent
Kajaste-Rudnitski et al.

(10) Patent No.: US 10,391,201 B2
(45) Date of Patent: Aug. 27, 2019

(54) GENE THERAPY

(71) Applicants: Ospedale San Raffaele S.r.l., Milan (IT); Fondazione Telethon, Rome (IT)

(72) Inventors: Anna Kajaste-Rudnitski, Milan (IT); Eugenio Montini, Milan (IT)

(73) Assignees: OSPEDALE SAN RAFFAELE SRL, Milan (IT); FONDAZIONE TELETHON, Rome (IT)

( * ) Notice: Subject to any disclaimer, the term of this patent is extended or adjusted under 35 U.S.C. 154(b) by 0 days.

(21) Appl. No.: 15/306,682

(22) PCT Filed: Apr. 24, 2015

(86) PCT No.: PCT/IB2015/053000
§ 371 (c)(1),
(2) Date: Oct. 25, 2016

(87) PCT Pub. No.: WO2015/162594
PCT Pub. Date: Oct. 29, 2015

(65) Prior Publication Data
US 2017/0056558 A1 Mar. 2, 2017

(30) Foreign Application Priority Data

Apr. 25, 2014 (GB) .................................. 1407322.5

(51) Int. Cl.
A61K 35/28 (2015.01)
A61L 27/38 (2006.01)
C07K 7/64 (2006.01)
C12N 5/0789 (2010.01)
C12N 15/86 (2006.01)
A61L 27/36 (2006.01)

(52) U.S. Cl.
CPC .......... *A61L 27/3834* (2013.01); *A61K 35/28* (2013.01); *A61L 27/3608* (2013.01); *A61L 27/3616* (2013.01); *A61L 27/3687* (2013.01); *C07K 7/645* (2013.01); *C12N 5/0647* (2013.01); *C12N 15/86* (2013.01); *C12N 2510/00* (2013.01); *C12N 2740/15043* (2013.01); *C12N 2740/16043* (2013.01)

(58) Field of Classification Search
None
See application file for complete search history.

(56) References Cited

U.S. PATENT DOCUMENTS

2015/0352228 A1* 12/2015 Torbett ................. A61K 31/436
514/44 R

FOREIGN PATENT DOCUMENTS

| WO | WO 98/005635 | 2/1998 |
| WO | WO 98/007859 | 2/1998 |
| WO | WO 98/009985 | 3/1998 |
| WO | WO 98/017815 | 4/1998 |
| WO | WO 2004/098531 | 11/2004 |
| WO | WO 2014/109728 | 7/2014 |
| WO | WO 2015/059674 | 4/2015 |

OTHER PUBLICATIONS

Cornilescu, C. et al., "Structural Analysis of the N-Terminal Domain of the HUman T-Cell Leukemia Virus Capsid Protein", J. Mol. Biol., 2000, VOl. 306: pp. 783-797.*
De Iaco et al., Cyclophilin A promotes HIV-1 reverse transcription but its effect on transduction correlates best with its effect on nuclear entry . . . ; Retrovirol. 11:11 (2014).
Kajaste-Rudnitski et al., Cellular Innate Immunity and Restriction of Viral Infection: Implications for Lentiviral Gene Therapy . . . ; Human Gene Ther. 26:201-209 (2015).
Liu et al., The Interferon-Inducible MxB Protein Inhibits HIV-1 Infection; Cell Host & Microbe 14:398-410 (2013).
Montini et al., Hematopoietic stem cell gene transfer in a tumor-prone mouse model uncovers low genotoxicity . . . ; Nature Biotechnol, 24:687-696 (2006).
Petrillo et al., Cyclosporin A and Rapamycin Relieve Distinct Lentiviral Restriction Blocks in Hematopoietic Stem and Progenitor Cells; Molec. Ther. 23:352-362 (2015).
Rits et al., Efficient Transduction of Simian Cells by HIV-1-based Lentiviral Vectors that Contain Mutations in the Capsid Protein; Molec. Ther. 15:930-937 (2007).
Sutherland et al., Effects of Cyclosporine A on Lentiviral Transduction of Mouse Hematopoietic Stem Cells and Transplantation . . . ; Blood 110:Abstract 5147 (2007).
Uchida et al., Optimal conditions for lentiviral transduction of engrafting human CD34+ cells; Gene Ther. 18:1078-1086 (2011).
Uchida et al., Efficient transduction of human hematopoietic repopulating cells with a chimeric HIV1-based vector including SIV capsid; Exper. Hematol. 41:779-788 (2013).
Wang et al., Rapamycin relieves lentiviral vector transduction resistance in human and mouse hematopoietic stem cells; Blood 124:913-923 (2014).
Fujita et al., Cyclophilin A-Independent Replication of a Human Immunodeficiency Virus Type 1 Isolate Carrying a Small Portion of the Simian Immunodeficiency Virus SIVmAc gag.
Kahl et al., "Tissue-specific restriction of cyclophilin A-independent HIV-1- and SIV-derived lentiviral vectors," Gene Therapy, (2008), vol. 15, pp. 1079-1108.
Noser et al., "Cyclosporine Increases Human Immunodeficiency Virus Type 1 Vector Transduction of Primary Mouse Cells," Journal of Virology, (2006), vol. 80, No. 15, pp. 7769-7.
Santoni De Sio et al., "Lentiviral Vector Gene Transfer is Limited by the Proteasome at Postentry Steps in Various Types of Stem Cells," Stemcells, (2008), vol. 26, pp. 2142-2.
Petrillo et al. (2014) Dissecting Immunomodulatory Relief of Lentiviral Restriction in Human Hematopoietic Stem and Progenitor . . . , Molec. Ther. 22(Supp. 1): S205, Abstract 528.

(Continued)

*Primary Examiner* — Michael D Burkhart
(74) *Attorney, Agent, or Firm* — Grimes & Yvon LLP

(57) ABSTRACT

Use of cyclosporin A (CsA) or a derivative thereof for increasing the efficiency of transduction of an isolated population of human haematopoietic stem and/or progenitor cells by a vector derived from HIV-1, HIV-2, FIV, BIV, EIAV, CAEV or visna lentivirus.

15 Claims, 39 Drawing Sheets
Specification includes a Sequence Listing.

(56) References Cited

OTHER PUBLICATIONS

Agudo, J. et al. (2012) A TLR and Non-TLR Mediated Innate Response to Lentiviruses Restricts Hepatocyte . . . , Molec. Ther., vol. 20, No. 12, pp. 257-2267.
Aiuti, A. et al. (2009) Gene therapy for immunodeficiency due to adenosine deaminase deficiency., N. Engl. J. Med. 360: 447-458.
Aiuti, A. et al. (2013) Lentiviral hematopoietic stem cell gene therapy in patients with Wiskott-Aldrich syndrome, Science 341: 1233151.
Allouch, A. et al. (2011), The TRIM Family Protein KAP1 Inhibits HIV-1 Integration, Cell Host Microbe vol. 9(6): 484-495.
Ausubel, F. M. et al. (1995 and periodic supplements) Current Protocols in Molecular Biology, John Wiley & Sons; pp. iii-xxii.
Biffi, A. et al. (2013) Lentiviral hematopoietic stem cell gene therapy benefits metachromatic leukodystrophy, Science 341: 1233158.
Boztug, K. et al. (2010), Stem-cell gene therapy for the Wiskott-Aldrich syndrome, N. Engl. J. Med. 363(20) pp. 1918-1927.
Breckpot, K. et al. (2010) HIV-1 Lentiviral Vector Immunogenicity is Mediated by Toll-Like Receptor 3 (TLR3) and TLR7, J. Virol. 84: 5627-5636.
Bukrinsky, M.I. et al. (1992) Active nuclear import of human immunodeficiency virus type 1 preintegration complexes, Proc. Natl. Acad. Sci, USA 89: 6580-2584.
Campbell, G. R. et al. (2011) Hormonally active vitamin D3 (1alpha,25-dihydroxycholecalciferol) triggers autophagy in human macrophages . . . , J. Biol. Chem. 286: 18890-18902.
Cao, W. et al. (2008) Toll-like receptor-mediated induction of type I interferon in plasmacytoid dendritic cells requires . . . , Nat. Immunol. 9(10): pp. 1157-1164.
Cartier, N. et al. (2009) Hematopoietic Stem Cell Gene Therapy with a Lentiviral Vector in X-Linked Adrenoleukodystrophy, Science 326: 818-823.
Chang, A. H. et al. (2007) The genetic engineering of hematopoietic stem cells: the rise of lentiviral vectors, the conundrum of the LTR . . . , Mol. Ther. 15(3): 445-456.
Coffin, J. M. et al. (1997) Retroviruses, Cold Spring Harbour Laboratory Press, 757-63.
Colgan, J. et al, (2005) Cyclophilin A-deficient mice are resistant to immunosuppression by cyclosporine, J. Immunol. 174: 6030-6038.
Colina, R. et al. (2008) Translational control of the innate immune response through IRF-7, Nature 452: 323-328.
De Iaco A and Luban J. Inhibition of HIV-1 infection by TNPO3 depletion is determined by capsid and detectable after viral cDNA enters the nucleus. Retrovirology. 2011; 8: 98.
Doulatov S et al., Revised map of the human progenitor hierarchy show the origin of mcarophages and denedritic cells . . . , Nat. Immunol., Jul. 2010, vol. 11, No. 7, pp. 585-593.
Doulatov, S. et al. (2012) Hematopoiesis: a human perspective, Cell Stem Cell 10(2) pp. 120-136.
Dull, T. et al. (1998) A third-generation lentivirus vector with a conditional packaging system, J. Virol. 72: 8463-8471.
Esplin, B. L. et al. (2011) Chronic exposure to a TLR ligand injures hematopoietic stem cells, J. Immunol. 186: 5367-5375.
Evans, M. E. et al. (2014) TRIM5alpha Variations Influence Transduction Efficiency With Lentiviral Vectors . . . , Molec. Ther. vol. 22 No. 2 pp. 348-358.
Fassati, A. (2012) Multiple roles of the capsid protein in the early steps of HIV-1 infection, Virus Research 170(102): 15-24.
Follenzi, A. et al. (2000) Gene transfer by lentiviral vectors is limited by nuclear translocation and rescued by HIV-1 pol sequences, Nat. Genetics 25(2): 217-222.
Follenzi, A. et al. (2002) Generation of HIV-1 derived lentiviral vectors, Methods Enzymol. 346: 454-465.
Frausto, S. D. et al. (2013) Cyclophilins as modulators of viral replication, Viruses 5(7): 1684-1701.
Gait, M. J. (1984) Oligonucleotide Synthesis: A Practical Approach, IRL Press; pp. vii-xiii.
Goujon, C. et al. (2013) Human MX2 is an interferon-induced post-entry inhibitor of HIV-1 infection, Nature 502: 559-562.

Grütter, M. G. et al. (2012) TRIM5 structure, HIV-1 capsid recognition, and innate immune signaling, Current Opinion Virology 2 (2): 142-150.
Hacein-Bey-Abina, S. et al. (2010) Efficacy of gene therapy for X-linked severe combined immunodeficiency, N. Engl. J. Med. 363(4): 355-364.
Harding, M. W. et al. (1989) A receptor for the immunosuppressant FK506 is a cis-trans peptidyl-prolyl isomerase, Nature 341(6244): 758-760.
Hatziioannou T et al., Retrovirus resistance factors Ref1 and Lv1 are species-specific variants of TRIM5α, Proc Natl Acad Sci, Jul. 20, 2004, vol. 101, No. 29, pp. 10774-10779.
Huang, J. et al. (2012) Maintenance of hematopoietic stem cells through regulation of Wnt and mTOR pathways, Nat. Medicine 18: 1778-1785.
Kajaste-Rudnitski, A. et al. (2006) The 2',5'-oligoadenylate synthetase 1b is a potent inhibitor of West Nile virus replication . . . , J. Biol. Chem. 281(8): 4624-4637.
Kajaste-Rudnitski, A. et al. (2011) TRIM22 inhibits HIV-1 transcription independently of its E3 ubiquitin ligase activity . . . , J. Virol. 85: 5183-5196.
Kane, M. et al. (2013) MX2 is an interferon-induced inhibitor of HIV-1 infection, Nature 502: 563-6.
Keckesova, Z. et al. (2006) Cyclophilin A renders human immunodeficiency virus type 1 sensitive to Old World monkey but not human TRIM5 . . . , J. Virol. 80(1): 4683-4690.
Kondo, Y. et al. (2005) The role of autophagy in cancer development and response to therapy, Nature Rev, Cancer 5(9): 726-734.
Leavitt, A. D. et al. (1996) Human immunodeficiency virus type 1 integrase mutants retain in vitro integrase activity yet fail to integrate . . . , J. Virol, 70(2): 721-728.
Leuci, V. et al, (2011) Transient proteasome inhibition as a strategy to enhance lentiviral transduction . . . , J. Biotechnol. 156(3): 218-226.
Lewis, P. et al. (1992) Human immunodeficiency virus infection of cells arrested in the cell cycle, EMBO J. 11(8): 3053-3058.
Lewis, P. F. et al. (1994) Passage through mitosis is required for oncoretroviruses but not for the human immunodeficiency virus, J. Virol. 68(1): 510-516.
Li, Y. et al, (2009) Target Cell Type-Dependent Modulation of Human Immunodeficiency Virus Type 1 Capsid Disassembly by Cyclophilin A, J. Virol. 83(21): 10951-10962.
Lilley, D. M., and Dahlberg, J. E. (1992) Methods in Enzymology: DNA Structures Part A: Synthesis and Physical Analysis of DNA, Academic Press, pp. v-vii.
Liu, Z. et al. (2013) The interferon-inducible MxB protein inhibits HIV-1 infection, Cell Host Microbe 14(4): 398-410.
Luban, J. et al. (1993) Human immunodeficiency virus type 1 Gag protein binds to cyclophilins A and B, Cell 73(6): 1067-1078.
Matrai, J. et al. (2011) Hepatocyte-targeted expression by integrase-defective lentiviral vectors induces antigen-specific tolerance . . . , Hepatology 53: 1696-1707.
Merten, O. W. et al. (2011) Large-scale manufacture and characterization of a lentiviral vector produced for clinical ex vivo gene therapy . . . , Human Gene Ther. 22(3): 343-356.
Monini, P. et al. (1999) Reactivation and Persistence of Human Herpesvirus-8 Infection in B Cells and Monocytes . . . , Blood 93: pp. 4044-4058.
Nagai, Y. et al. (2006) Toll-like receptors on hematopoietic progenitor cells stimulate innate immune system replenishment, Immunity 24(6): 801-812.
Nagy, P. D. et al. (2011) Emerging picture of host chaperone and cyclophilin roles in RNA virus replication, Virology 411(2): 374-382.
Naldini, L. (2011) Ex vivo gene transfer and correction for cell-based therapies, Nat. Rev. Genetics 12: 301-15.
Naldini, L. et al. (1996a) In vivo gene delivery and stable transduction of nondividing cells by a lentiviral vector, Science 272(5259): 263-267.
Naldini, L. et al. (1996b) Efficient transfer, integration, and sustained long-term expression of the transgene . . . , Proc. Natl. Acad. Sci. USA, vol. 93(21), pp. 11382-11388.

(56) References Cited

OTHER PUBLICATIONS

Nightingale, S. J. et al. (2006) Transient gene expression by nonintegrating lentiviral vectors, Mol. Ther. 13(6): 1121-1132.
Notta F et al. (2011) Isolation of single human hematopoietic stem cells capable of long-term multilineage engraftment, Science, vol. 333, pp. 218.
Petrillo C et al. (2014) Cyclosporin A and Rapamycin Relieve Distinct Lentiviral Restriction Blocks . . . , Molec. Ther. 23(2): 352-362.
Petrillo C et al. (2014) Rapa and CSA Improve LV Transduction in Human HSPC, Supplementary Materials, Molec. Ther. 23(2): 28 pages.
Polak, J. M., and McGee, J. O'D, (1990) In Situ Hybridization: Principles and Practice, Oxford University Press, pp. vii-viii.
Price, A. J. et al. (2012) CPSF6 defines a conserved capsid interface that modulates HIV-1 replication, PLoS Pathog. 8(8): e1002896.
Qi, M. et al. (2008) Cyclophilin A-dependent restriction of human immunodeficiency virus type 1 capsid mutants . . . , J. Virol. 82(24): 12001-12008.
Rasaiyaah, J. et al. (2013) HIV-1 evades innate immune recognition through specific cofactor recruitment, Nature 503(7476): 402-405.
Roe, B., Crabtree, J., and Kahn, A. (1996) DNA Isolation and Sequencing: Essential Techniques, John Wiley & Sons, pp. v-vii.
Rohrabaugh, S. L. et al. (2011) Ex vivo Rapamycin treatment of human cord blood CD34+ cells enhnaces . . . , Blood Cells Mol. Dis. 46: 318-20.
Rowe, H. M. et al. (2010) KAP1 controls endogenou retroviruses in embryonic stem cells, Nature 463: 237-40.
Rubinsztein, D. C. et al. (2012) Autophagy modulation as a potetial therapeutic target for diverse diseases, Nat. Rev. Drug Discovery 11: 709-30.
Sabers, C. J. et al. (1995) Isolation of Protein Target of the FKBP12-Rapamycin Complex in Mammalian Cells, J. Biol. Chem. 270: 815-22.
Sambrook, J., Fritsch, E. F., and Maniatis, T. (1989) Molecular Cloning: A Laboratory Manual, 2nd Edition, Cold Spring Harbor Laboratory Press, pp. v-xxxii.
Santoni de Sio, F. R. et al (2006) Proteasome activity restricts lentiviral gene transfer into hematopoietic stem cells and is down-regulated . . . , Blood 107: 4257-65.
Sarkar, S. et al. (2008) Small molecule enhancers of autophagy for neurodegenerative diseases, Molecular bioSystems 4: 895-901.
Schaller, T. et al. (2011) HIV-1 Capsid-Cyclophilin Interactions Determine Nuclear Import Pathway, Integration Targeting ad Replication Efficiency, PLoS Pathog. 7: e1002439.
Schreiber, S.L. et al. (1992) The mechanism of action of cyclosporin A and FK506, Immunology Today 13: 136-42.
Siekierka, J. J. et al. (1989) A cytosolic binding protein for the immunosuppressant FK506 has peptidyl-prolyl isomerase activity but is distinct . . . , Nature 341: 755-7.
Sokolskaja, E. et al. (2004) Target Cell Cyclophilin A Modulates Human Immunodeficiency Virus Type 1 Infectivity, J. Viral. 78: 12800-8.
Sokolskaja, E. et al. (2006) Cyclophilin, TRIM5, and innate immunity to HIV-1, Curr. Opin, Microbiol. 9: 404-8.
Song, C. et al. (2007) Analysis of Human Cell Heterokaryons Demonstrates that Target Cell Restriction of Cyclosporine-Resistant [HIV1] Mutants . . . , J. Virol. 81(21): 11946-56.
Strebel, K. et al. (2009) Human cellular restriction factors that target HIV-1 replication, BMC Medicine 7: 48.
Stremlau, M. et al. (2004) The cytoplasmic body component TRIM5α restricts HIV-1 infection in Old World monkeys, Nature 427: 848-853.
Sutlu, T. et al. (2012) Inhibition of Intracellular Antiviral Defense Mechanisms Augments Lentiviral Transduction . . . , Human Gene Therapy 23:1090-1100.
Takeuchi, H. et al. (2012) Host cell species-specific effect of cyclosporine A on simian immunodeficiency virus replication, Retrovirology 9: 3.
Towers, G. J. (2007) The control of viral infection by tripartite motif proteins and cyclophilin A, Retrovirology 4: 40.
Towers, G. J. et al. (2003) Cyclophilin A modulates the sensitivity of HIV-1 to host restriction factors, Nat. Medicine 9: 1138-43.
Uchida N et al. (2012) High-efficiency Transudction of Rhesus Hematopoietic Repopulating Cells . . . , Molecular Therapy. vol. 20, No. 10, pp. 1882-1892.
Veillette, M. et al. (2013) The V86M mutation in HIV-1 capsid confers resistance to TRIM5-alpha by abrogation of cyclophilin A-dependent restriction . . . , Retrovirology 10: 25.
Wang X et al. (2013) Rapamycin Treatment of Hematopoietic Stem Cells . . . , Advancing Sci. Gene Ther. Hematol. Dis. vol. 21, Special Issue , S13-S14.
Wang, X. et al. (2011) A Common Path to Innate Immunity to HIV-1 Induced by Toll-Like Receptor Ligands in Primary Human Macrophages, PLoS One 6: e24193.
Warr, M. R. et al. (2013) FoxO3a Directs a Protective Autophagy Program in Hematopoietic Stem Cells, Nature 494: 323-7.
Werneck, M. B. et al. (2012) Cyclosporin A inhibits colon cancer cell growth independently of the calcineurin pathway, Cell Cycle 11: 3997-4008.
Wolf, D. et al. (2007) TRIM28 Mediates Primer Binding Site-Targeted Silencing of Murine Leukemia Virus in Embryonic Cells, Cell 131: 46-57.
Ylinen, L. M. et al. (2009) Cyclophilin A Levels Dictate Infection Efficiency of Human Immunodeficiency Virus Type 1 Capsid Escape Mutants . . . , J. Virol. 83: 2044-7.
Ylinen, L. M. et al. (2005) Differential Restriction of Human Immunodeficiency Virus Type 2 and Simian Immunodeficency Virus . . . , J. Virol. 79(18): 11580-11587.
Zhang, Y (2001) Rational Design of Cyclosporin A Derivatives for selective enzyme Inhibition, Dissertation, Martn Luther Universität Halle-Wittenberg.
Zhou, L. et al. (2011) Transportin 3 Promotes a Nuclear Maturation Step Required for Efficient HIV-1 Integration, PLoS Pathog. 7.
Zhu, K. et al. (2010) Proteasome inhibitors activate autophagy as a cytoprotective response in human prostate cancer cells, Oncogene 29: 451-62.

* cited by examiner

Figure 1

```
gtagacaggatgaggattaacacatggaattccggagcggccgcaggagctttgttccttgggttcttgggagcagcaggaagcactatgggcgcag
cctcaatgacgctgacggtacaggccagacaattattgtctggtatagtgcagcagcagaacaatttgctgagggctattgagcgcaacagcatct
gttgcaactcacagtctgggcatcaagcagctccaggcaagaatcctggctgtggaaagatacctaaaggatcaacagctcctggggatttggggt
tgctctggaaaactcatttgcaccactgctgtgccttggaatgctagtttggagtaataaatctctgggaacagatttggaatcacacgacctggatgg
agtgggacagagaaattaacaattacacaagcttccgcgcgaattcaccccaccagtgcaggctgcctatcagaaagtggtggctggtgtggctaatg
ccctggcccacaagtttcactaagctcgcttccttgctgtgtccaatttctattaaaggttccttggttccctaagtccaactactaaactgggggata
ttatgaagggccttgagcatctggattctgcctaataaaaaaacatttattttcattgcaatgatgtatttaaattattttctgaatatttttactaaaa
agggaatgtgggaggtcagtgcatttaaaacataaagaaatgaagagctagttcaaacct tgggaaaatacactatatcttaaactccatgaaagaa
ggtgaggctgcaaacagctaatgcacattggcaacagccctgatgcctatgccttattcatccctcagaaaaggattcaagtagaggcttgatttgg
aggttaaagtttggctatgctgtatttacattacttattgttttagctgtcctcatgaatgtcttttcactacccatttgcttatcctgcatctct
cagccttgactccactcagttctcttgcttagagataccaccttt ccctgaagtgttccttccatgttttacggcgagatggtttctcctcgcctg
gccactcagccttagttgtctctgttgtcttatagaggtctacttgaagaaggaaaaacaggggg catggtttgactgtcctgtgagcccttcttcc
ctgcctccccactcacagtgaccggaatccctcgacatggcagtctagcactagtgcggccgcagatctgcttcctcgctcactgactcgctgcg
ctcggtcgttcggctgcggcgagcggtatcagctcactcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgctctcctgttccgaccctgcc
gcttaccggatacctgtccgcctttctcccttcgggaagcgtggcgctttctcaatgctcacgctgtaggtatctcagttcggtgtaggtcgttcgc
tccaagctgggctgtgtgcacgaacccccgttcagcccgaccgctgcgccttatccggtaactatcgtcttgagtccaacccggtaagacacgact
tatcgccactggcagcagccactggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgatccggcaaacaaaccaccgct
ggtagcggtggtttttttgtttgcaagcagcagattacgcgcagaaaaaaaggatctcaagaagatcctttgatcttttctacgggtctgacgctc
agtggaacgaaaactcacgttaagggattttggtcatgagattatcaaaaggatcttcacctagatccttttaaattaaaaatgaagttttaaatc
aatctaaagtatatatgagtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgataccgcgagacccacgctcaccgg
ctccagatttatcagcaataaaccagccagccggaagggccgagcgcagaagtggtcctgcaactttatccgcctccatccagtctattaattgttg
ccgggaagctagagtaagtagttcgccagttaatagtttgcgcaacgttgttgccattgctacaggcatcgtggtgtcacgctcgtcgtttggtatg
gcttcattcagctccggttcccaacgatcaaggcgagttacatgatcccccatgttgtgcaaaaaagcggttagctccttcggtcctccgatcgttg
tcagaagtaagttggccgcagtgttatcactcatggttatggcagcactgcataattctcttactgtcatgccatccgtaagatgcttttctgtgac
tggtgagtactcaaccaagtcattctgagaatagtgtatgcggcgaccgagttgctcttgcccggcgtcaatacgggataataccgcgccacatagc
agaactttaaaagtgctcatcattggaaaacgttcttcggggcgaaaactctcaaggatcttaccgctgttgagatccagttcgatgtaacccactc
gtgcacccaactgatcttcagcatcttttactttcaccagcgtttctgggtgagcaaaaacaggaaggcaaaatgccgcaaaaaagggaataagggc
gacacggaaatgttgaatactcatactcttcctttttcaatattattgaagcatttatcaggttattgtctcatgagcggatacatatttgaatgt
atttagaaaaataaacaaataggggttccgcgcacatttccccgaaaagtgccacctgacgt
```

Figure 1 (cont.)

```
atgggtgcgagagcgtcagtattaagcgggggagaattagatcgatgggaaaaaattcggttaaggccaggggggaaagaaaaaatataaattaa
aacatatagtatgggcaagcagggagctagaacgattcgcagttaatcctggcctgttagaaacatcagaaggctgtagacaaatactgggaca
gctacaaccatcccttcagacaggatcagaagaacttagatcattatataatacagtagcaaccctctattgtgtgcatcaaaggatagagata
aaagacaccaaggaagctttagacaagatagaggaagagcaaaacaaaagtaagaaaaaagcacagcaagcagcagctgacacaggacacagca
atcaggtcagccaaaattacCCTATAGTGCAGAACATCCAGGGGCAAATGGTACATCAGGCCATATCAGCTAGAACTTTAAATGCATGGGTAAA
AGTAGTAGAAGAGAAGGCTTTCAGCCCAGAAGTGATACCCATGTTTTCAGCATTATCAGAAGGAGCCACCCCACAAGATTTAAACACCATGCTA
AACACAGTGGGGGGACATCAAGCAGCCATGCAAATGTTAAAAGAGACCATCAATGAGGAAGCTGCAGAATGGGATAGAGTGCATCCAGTGCATG
CAGGGCCTATTGCACCAGGCCAGATGAGAGAACCAAGGGGAAGTGACATAGCAGGAACTACTAGTACCCTTCAGGAACAAATAGGATGGATGAC
ACATAATCCACCTATCCCAGTAGGAGAAATCTATAAAAGATGGATAATCCTGGGATTAAATAAAATAGTAAGAATGTATAGCCCTACCAGCATT
CTGGACATAAGACAAGGACCAAAGGAACCCTTTAGAGACTATGTAGACCGATTCTATAAAACTCTAAGAGCCGAGCAAGCTTCACAAGAGGTAA
AAAATTGGATGACAGAAACCTTGTTGGTCCAAAATGCGAACCCAGATTGTAAGACTATTTTAAAAGCATTGGGACCAGGAGCGACACTAGAAGA
AATGATGACAGCATGTCAGGGAGTGGGGGGACCCGGCCATAAAGCAAGAGTTttggctgaagcaatgagccaagtaacaaatccagctaccata
atgatacagaaaggcaattttaggaaccaaagaaagactgttaagtgtttcaattgtggcaaagaagggcacatagccaaaaattgcagggccc
ctaggaaaaagggctgttggaaatgtggaaaggaaggacaccaaatgaaagattgtactgagagacaggctaattttttagggaagatctggcc
ttcccacaagggaaggccagggaatttcttcagagcagaccagagccaacagccccaccagaagagagcttcaggtttggggaagagacaaca
actccctctcagaagcaggagccgatagacaaggaactgtatcctttagcttccctcagatcactctttggcagcgacccctcgtcacaataa
```

Figure 2

```
CCTATAGTGCAGAACATCCAGGGGCAAATGGTACATCAGGCCATATCACCTAGAACTTTAAATGCATGGGTAAAAGTAGTAGAAGAGAAGGCTT
TCAGCCCAGAAGTGATACCCATGTTTTCAGCATTATCAGAAGGAGCCACCCCACAAGATTTAAACACCATGCTAAACACAGTGGGGGGACATCA
AGCAGCCATGCAAATGTTAAAAGAGACCATCAATGAGGAAGCTGCAGAATGGGATAGAGTGCATCCAGTGCATGCAGGGCCTATTGCACCAGGC
CAGATGAGAGAACCAAGGGGAAGTGACATAGCAGGAACTACTAGTACCCTTCAGGAACAAATAGGATGGATGACACATAATCCACCTATCCCAG
TAGGAGAAATCTATAAAAGATGGATAATCCTGGGATTAAATAAAATAGTAAGAATGTATAGCCCTACCAGCATTCTGGACATAAGACAAGGACC
AAAGGAACCCTTTAGAGACTATGTAGACCGATTCTATAAAACTCTAAGAGCCGAGCAAGCTTCACAAGAGGTAAAAAATTGGATGACAGAAACC
TTGTTGGTCCAAAATGCGAACCCAGATTGTAAGACTATTTTAAAAGCATTGGGACCAGGAGCGACACTAGAAGAAATGATGACAGCATGTCAGG
GAGTGGGGGGACCCGGCCATAAAGCAAGAGTT
```

Figure 3

PIVQNIQGQMVHQAISPRTLNAWVKVVEEKAFSPEVIPMFSALSEGATPQDLNTMLNTVGGHQAAMQMLKETINEEAAEWDRVHPVHAGPIAPG
QMREPRGSDIAGTTSTLQEQIGWMTHNPPIPVGEIYKRWIILGLNKIVRMYSPTSILDIRQGPKEPFRDYVDRFYKTLRAEQASQEVKNWMTET
LLVQNANPDCKTILKALGPGATLEEMMTACQGVGGPGHKARVX

Figure 4

```
CLUSTAL 2.1 multiple sequence alignment

Gag_IIIB_LAI    MGARASVLSGGELDRWEKIRLRPGGKKKYKLKHIVWASRELERFAVNPGLLETSEGCRQI 60
p24_pMDL        ------------------------------------------------------------

Gag_IIIB_LAI    LGQLQPSLQTGSEELRSLYNTVATLYCVHQRIEIKDTKEALDKIEEEQNKSKKKAQQAAA 120
p24_pMDL        ------------------------------------------------------------

Gag_IIIB_LAI    DTGHSSQVSQNYPIVQNIQGQMVHQAISPRTLNAWVKVVEEKAFSPEVIPMFSALSEGAT 180
p24_pMDL        ------------PIVQNIQGQMVHQAISPRTLNAWVKVVEEKAFSPEVIPMFSALSEGAT 48
                            ************************************************

Gag_IIIB_LAI    PQDLNTMLNTVGGHQAAMQMLKETINEEAAEWDRVHPVHAGPIAPGQMREPRGSDIAGTT 240
p24_pMDL        PQDLNTMLNTVGGHQAAMQMLKETINEEAAEWDRVHPVHAGPIAPGQMREPRGSDIAGTT 108
                ************************************************************

Gag_IIIB_LAI    STLQEQIGWMTNNPPIPVGEIYKRWIILGLNKIVRMYSPTSILDIRQGPKEPFRDYVDRF 300
p24_pMDL        STLQEQIGWMTHNPPIPVGEIYKRWIILGLNKIVRMYSPTSILDIRQGPKEPFRDYVDRF 168
                ***********:************************************************

Gag_IIIB_LAI    YKTLRAEQASQEVKNWMTETLLVQNANPDCKTILKALGPAATLEEMMTACQGVGGPGHKA 360
p24_pMDL        YKTLRAEQASQEVKNWMTETLLVQNANPDCKTILKALGPGATLEEMMTACQGVGGPGHKA 228
                ***************************************.********************

Gag_IIIB_LAI    RVLAEAMSQVTNSATIMMQRGNFRNQRKIVKCFNCGKEGHIARNCRAPRKKGCWKCGKEG 420
p24_pMDL        RVX--------------------------------------------------------- 231
                **

Gag_IIIB_LAI    HQMKDCTERQANFLGKIWPSYKGRPGNFLQSRPEPTAPPEESFRSGVETTTPSQKQEPID 480
p24_pMDL        ------------------------------------------------------------

Gag_IIIB_LAI    KELYPLTSLRSLFGNDPSSQ 500
p24_pMDL        --------------------
```

Figure 5(a)

```
CLUSTAL 2.1 multiple sequence alignment

Gag_HXB2_LAI        MGARASVLSGGELDRWEKIRLRPGGKKKYKLKHIVWASRELERFAVNPGLLETSEGCRQI 60
p24_pMDL            ------------------------------------------------------------

Gag_HXB2_LAI        LGQLQPSLQTGSEELRSLYNTVATLYCVHQRIEIKDTKEALDKIEEEQNKSKKKAQQAAA 120
p24_pMDL            ------------------------------------------------------------

Gag_HXB2_LAI        DTGHSNQVSQNYPIVQNIQGQMVHQAISPRTLNAWVKVVEEKAFSPEVIPMFSALSEGAT 180
p24_pMDL            ------------PIVQNIQGQMVHQAISPRTLNAWVKVVEEKAFSPEVIPMFSALSEGAT 48
                                ************************************************

Gag_HXB2_LAI        PQDLNTMLNTVGGHQAAMQMLKETINEEAAEWDRVHPVHAGPIAPGQMREPRGSDIAGTT 240
p24_pMDL            PQDLNTMLNTVGGHQAAMQMLKETINEEAAEWDRVHPVHAGPIAPGQMREPRGSDIAGTT 108
                    ************************************************************

Gag_HXB2_LAI        STLQEQIGWMTNNPPIPVGEIYKRWIILGLNKIVRMYSPTSILDIRQGPKEPFRDYVDRF 300
p24_pMDL            STLQEQIGWMTHNPPIPVGEIYKRWIILGLNKIVRMYSPTSILDIRQGPKEPFRDYVDRF 168
                    ***********:************************************************

Gag_HXB2_LAI        YKTLRAEQASQEVKNWMTETLLVQNANPDCKTILKALGPAATLEEMMTACQGVGGPGHKA 360
p24_pMDL            YKTLRAEQASQEVKNWMTETLLVQNANPDCKTILKALGPGATLEEMMTACQGVGGPGHKA 228
                    ***************************************.********************

Gag_HXB2_LAI        RVLAEAMSQVTNSATIMMQRGNFRNQRKIVKCFNCGKEGHTARNCRAPRKKGCWKCGKEG 420
p24_pMDL            RVX--------------------------------------------------------- 231
                    **

Gag_HXB2_LAI        HQMKDCTERQANFLGKIWPSYKGRPGNFLQSRPEPTAPPEESFRSGVETTTPPQKQEPID 480
p24_pMDL            ------------------------------------------------------------

Gag_HXB2_LAI        KELYPLTSLRSLFGNDPSSQ 500
p24_pMDL            --------------------
```

Figure 5(b)

```
CLUSTAL 2.1 multiple sequence alignment

Gag_BAL    ARASVLSGGELDRWEKIRLRPGGKKKYRLKHIVWASRELERFAVNPGLLETSEGCRQILG 60
p24_pMDL   ------------------------------------------------------------

Gag_BAL    QLQPSLQTGSEEIRSLYNTIATLYCVHQKIEVKDTKEALDKIEEEQNKSKKKAQQAAADT 120
p24_pMDL   ------------------------------------------------------------

Gag_BAL    GNSGQVSQNFPIVQNLQGQMVHQAISPRTLNAWVKVVEEKAFSPEVIPMFSALSEGATPQ 180
p24_pMDL   ----------PIVQNIQGQMVHQAISPRTLNAWVKVVEEKAFSPEVIPMFSALSEGATPQ 50
                     *****:**********************************

Gag_BAL    DLNTMLNTVGGHQAAMQMLKETINEEAAEWDRLHPVQAGPVAPGQIRDPRGSDIAGTTST 240
p24_pMDL   DLNTMLNTVGGHQAAMQMLKETINEEAAEWDRVHPVHAGPIAPGQMREPRGSDIAGTTST 110
           *******************************:***.***:****:*:************

Gag_BAL    LQEQIGWMTSNPPIPVGEIYKRWIILGLNKIVRMYSPTSILDIRQGPKEPFRDYVDRFYK 300
p24_pMDL   LQEQIGWMTHNPPIPVGEIYKRWIILGLNKIVRMYSPTSILDIRQGPKEPFRDYVDRFYK 170
           ********* **************************************************

Gag_BAL    TLRAEQASQEVKNWMTETLLVQNANPDCKTILKALGPAATLEEMMTACQGVGGPSHKARI 360
p24_pMDL   TLRAEQASQEVKNWMTETLLVQNANPDCKTILKALGPGATLEEMMTACQGVGGPGHKARV 230
           *************************************.***************.****:

Gag_BAL    LAEAMSQVTNSATIMMQKGNFRNQRKIVKCFNCGKEGHIARNCRAPRKRGCWKCGKEGHQ 420
p24_pMDL   X----------------------------------------------------------- 231

Gag_BAL    MKDCTERQANFLGKIWPSHKGRPGNFLQSRPEPTAPPAPPEESFRFGEETTTPSQKQELI 480
p24_pMDL   ------------------------------------------------------------

Gag_BAL    DKELYPLASLRSLFGNDPSSQ 501
p24_pMDL   ---------------------
```

Figure 5(c)

```
CLUSTAL 2.1 multiple sequence alignment p24_pNL4_3      PIVQNLQGQMVHQAISPRTLNAWVKVVEEKAFSPEVIPMFSALSEGATPQDLNTMLNTVG 60
p24_pMDL        PIVQNIQGQMVHQAISPRTLNAWVKVVEEKAFSPEVIPMFSALSEGATPQDLNTMLNTVG 60
                ***:**************************************************** p24_pNL4_3      GHQAAMQMLKETINEEAAEWDRLHPVHAGPIAPGQMREPRGSDIAGTTSTLQEQIGWMTH 120
p24_pMDL        GHQAAMQMLKETINEEAAEWDRVHPVHAGPIAPGQMREPRGSDIAGTTSTLQEQIGWMTH 120
                ********************:*********************************** p24_pNL4_3      NPPIPVGEIYKRWIILGLNKIVRMYSPTSILDIRQGPKEPFRDYVDRFYKTLRAEQASQE 180
p24_pMDL        NPPIPVGEIYKRWIILGLNKIVRMYSPTSILDIRQGPKEPFRDYVDRFYKTLRAEQASQE 180
                ************************************************************ p24_pNL4_3      VKNWMTETLLVQNANPDCKTILKALGPGATLEEMMTACQGVGGPGHKARVX 231
p24_pMDL        VKNWMTETLLVQNANPDCKTILKALGPGATLEEMMTACQGVGGPGHKARVX 231
                ****************************************************
```

Figure 5(d)

```
  1 - CCT ATA GTG CAG AAC ATC CAG GGG CAA ATG GTA CAT CAG GCC ATA TCA CCT AGA ACT TTA  -  60
  1 -  P   I   V   Q   N   I   Q   G   Q   M   V   H   Q   A   I   S   P   R   T   L  -  20

61 - AAT GCA TGG GTA AAA GTA GTA GAA GAG AAG GCT TTC AGC CCA GAA GTG ATA CCC ATG TTT  - 120
 21 -  N   A   W   V   K   V   V   E   E   K   A   F   S   P   E   V   I   P   M   F  -  40

121 - TCA GCA TTA TCA GAA GGA GCC ACC CCA CAA GAT TTA AAC ACC ATG CTA AAC ACA GTG GGG  - 180
 41 -  S   A   L   S   E   G   A   T   P   Q   D   L   N   T   M   L   N   T   V   G  -  60

181 - GGA CAT CAA GCA GCC ATG CAA ATG TTA AAA GAG ACC ATC AAT GAG GAA GCT GCA GAA TGG  - 240
 61 -  G   H   Q   A   A   M   Q   M   L   K   E   T   I   N   E   E   A   A   E   W  -  80

241 - GAT AGA GTG CAT CCA GTG CAT GGA GGG CCT ATT GCA CCA GGC CAG ATG AGA GAA CCA AGG  - 300
 81 -  D   R   V   H   P   V   H   A   G   P   I   A   P   G   Q   M   R   E   P   R  - 100

301 - GGA AGT GAC ATA GCA GGA ACT ACT AGT ACC CTT CAG GAA CAA ATA GGA TGG ATG ACA CAT  - 360
101 -  G   S   D   I   A   G   T   T   S   T   L   Q   E   Q   I   G   W   M   T   H  - 120

361 - AAT CCA CCT ATC CCA GTA GGA GAA ATC TAT AAA AGA TGG ATA ATC CTG GGA TTA AAT AAA  - 420
121 -  N   P   P   I   P   V   G   E   I   Y   K   R   W   I   I   L   G   L   N   K  - 140

421 - ATA GTA AGA ATG TAT AGC CCT ACC AGC ATT CTG GAC ATA AGA CAA GGA CCA AAG GAA CCC  - 480
141 -  I   V   R   M   Y   S   P   T   S   I   L   D   I   R   Q   G   P   K   E   P  - 160

481 - TTT AGA GAC TAT GTA GAC CGA TTC TAT AAA ACT CTA AGA GCC GAG CAA GCT TCA CAA GAG  - 540
161 -  F   R   D   Y   V   D   R   F   Y   K   T   L   R   A   E   Q   A   S   Q   E  - 180

541 - GTA AAA AAT TGG ATG ACA GAA ACC TTG TTG GTC CAA AAT GCG AAC CCA GAT TGT AAG ACT  - 600
181 -  V   K   N   W   M   T   E   T   L   L   V   Q   N   A   N   P   D   C   K   T  - 200

601 - ATT TTA AAA GCA TTG GGA CCA GGA GCG ACA CTA GAA GAA ATG ATG ACA GCA TGT CAG GGA  - 660
201 -  I   L   K   A   L   G   P   G   A   T   L   E   E   M   M   T   A   C   Q   G  - 220

661 - GTG GGG GGA CCC GGC CAT AAA GCA AGA GTT                                          - 690
221 -  V   G   G   P   G   H   K   A   R   V   X                                       - 240
```

Figure 6 ggatccccctgaggggccccatgggctagaggatccggcctcggcctctgcataaataaaaaaattagtcagccatgagcttggcccattgcata
cgttgtatccatatcataatatgtacatttatattggctcatgtccaacattaccgccatgttgacattgattattgactagttattaatagtaatc
aattacgggtcattagttcatagccatatatggagttccgcgttacataacttacggtaaatggcccgcctggctgacccgccaacgaccccgc
ccattgacgtcaataatgacgtatgttcccatagtaacgccaataggggactttccattgacgtcaatgggtggagtatttacggtaaactgccact
tggcagtacatcaagtgtatcatatgccaagtacgccccctattgacgtcaatgacggtaaatggcccgcctggcattatgcccagtacatgacctt
atgggactttcctacttggcagtacatctacgtattagtcatcgctattaccatggtgatgcggttttggcagtacatcaatgggcgtggatagcgg
tttgactcacggggatttccaagtctccaccccattgacgtcaatgggagtttgttttggcaccaaaatcaacgggactttccaaaatgtcgtaaca
actccgccccattgacgcaaatgggcggtaggcgtgtacggtgggaggtctatataagcagagctcgtttagtgaaccgtcagatcgcctggagacg
ccatccacgctgttttgacctccatagaagacaccggaccgatccagctccctcgaagcttacatgtggtaccgagctcggatcctgagaactt
cagggtgagtctatgggaccttgatgtttttcttttcccttcttttctatggttaagttcatgtcataggaaggggagaagtaacagggtacacata
ttgaccaaatcagggtaattttgcatttgtaattttaaaaaatgctttcttcttttaatatacttttttgtttatcttatttctaatacttttcccta
atctcttttctttcagggcaataatgatacaatgtatcatgcctcttgcaccattctaaagaataacagtgataatttctgggttaaggcaatagca
atatttctgcatataaatatttctgcatataaattgtaactgatgtaagaggtttcatattgctaatagcagctacaatccagctaccattctgctt
ttattttatggtgggataaggctggattattctgagtccaagctaggcccttttgctaatcatgttcatacctcttatcttcctcccacagctcct
gggcaacgtgctggtctgtgtgctggccatcactttggcaaagcacgtgagatctgaattcgagatctgccgccgccatgggtgcgagagcgtcag
tattaagcggggggagaattagatcgatgggaaaaaattcggttaaggccaggggggaaagaaaaaatataaattaaaacatatagtatgggcaagcag
ggagctagaacgattcgcagttaatcctggcctgttagaaacatcagaaggctgtagacaaatactgggacagctacaacccatccctccagacagga
tcagaagaacttagatcattatataatacagtagcaaccctctattgtgtgcatcaaaggatagagataaaagacaccaaggaagctttagacaaga
tagaggaagagcaaaacaaaagtaagaaaaaagcacagcaagcagcagctgacacaggacacagcaatcaggtcagccaaaattacCCTATAGTGCA
GAACATCCAGGGGCAAATGGTACATCAGGCCATATCACCTAGAACTTTAAATGCATGGGTAAAAGTAGTAGAAGAGAAGGCTTTCAGCCCAGAAGTG
ATACCCATGTTTTCAGCATTATCAGAAGGAGCCACCCCACAAGATTTAAACACCATGCTAAACACAGTGGGGGGACATCAAGCAGCCATGCAAATGT
TAAAAGAGACCATCAATGAGGAAGCTGCAGAATGGGATAGAGTGCATCCAGTGCATĂCAGGGCCTATTGCACCAGGCCAGATGAGAGAACCAAGGGG
AAGTGACATAGCAGGAACTACTAGTACCCTTCAGGAACAAATAGGATGGATGACACATAATCCACCTATCCCAGTAGGAGAAATCTATAAAAGATGG
ATAATCCTGGGATTAAATAAAATAGTAAGAATGTATAGCCCTACCAGCATTCTGGACATAAGACAAGGACCAAAGGAACCCTTTAGAGACTATGTAG
ACCGATTCTATAAAACTCTAAGAGCCGAGCAAGCTTCACAAGGAGGTAAAAAATTGGATGACAGAAACCTTGTTGGTCCAAAATGCGAACCCAGATTG
TAAGACTATTTTAAAAGCATTGGGACCAGGAGCGACACTAGAAGAAATGATGACAGCATGTCAGGGAGTGGGGGGACCCGGCCATAAAGCAAGAGTT
ttggctgaagcaatgagccaagtaacaaatccagctaccataatgatacagaaaggcaattttaggaaccaaagaaagactgttaagtgtttcaatt
gtggcaaagaagggcacatagccaaaaattgcagggcccctaggaaaaagggctgttggaaatgtgaaaggaaggacaccaaatgaaagattgtac
tgagagacaggctaattttttagggaagatctggccttcccacaggggaaggccaggaattttcttcagagcagaccagagccaacagccccacca
gaagagagcttcaggtttggggaagagacaacaactccctctcagaagcaggagccgatagacaaggaactgtatcctttagcttccctcagatcac
tctttggcagcgacccctcgtcacaataaagatagggggggcaattaaaggaagctctattagatacaggagcagatgatacagtattagaagaaatg
aatttgccaggaagatggaaaccaaaaatgatagggggaattggaggttttatcaaagtaggacagtatgatcagatactcatagaaatctgcggac
ataaagctataggtacagtattagtaggacctacacctgtcaacataattggaagaaatctgttgactcagattggctgcactttaaattttcccat
tagtcctattgagactgtaccagtaaaattaaagccaggaatggatggcccaaaagttaaacaatggccattgacagaagaaaaaataaaagcatta
gtagaaatttgtacagaaatggaaaaggaaggaaaaatttcaaaaattgggcctgaaaatccatacaatactccagtatttgccataaagaaaaag
acagtactaaatggagaaaattagtagatttcagagaacttaataagagaactcaagatttctgggaagttcaattaggaataccacatcctgcagg
gttaaaacagaaaaaatcagtaacagtactggatgtgggcgatgcatatttttcagttcccttagataaagacttcaggaagtatactgcatttacc
atacctagtataaacaatgagacaccagggattagatatcagtacaatgtgcttccacagggatggaaaggatcaccagcaatattccagtgtagca
tgacaaaaatcttagagccttttagaaaacaaaatccagacatagtcatctatcaatacatggatgatttgtatgtaggatctgacttagaaatagg
gcagcatagaacaaaatagaggaactgagacaacatctgttgaggtggggatttaccacaccagacaaaaaacatcagaaagaacctccattcctt
tggatgggttatgaactccatcctgataaatggacagtacagcctatagtgctgccagaaaaggacagctggactgtcaatgacatacagaaattag
tgggaaattgaattgggcaagtcagatttatgcagggattaaagtaaggcaattatgtaaactccttaggggaaccaaagcactaacagaagtagt
accactaacagaagaagcagagctagaactggcagaaaacagggagattctaaaagaaccggtacatggagtgtattatgacccatcaaaagactta
atagcagaaatacagaagcaggggcaaggccaatggacatatcaaatttatcaagagccatttaaaaatctgaaaacaggaaaatatgcaagaatga
agggtgcccacactaatgatgtgaaacaattaacagaggcagtacaaaaaatagccacagaaagcatagtaatatgggggaagactcctaaatttaa
attacccatacaaaaggaaacatgggaagcatggtggacagagtattggcaagccacctggattcctgagtgggagtttgtcaataccccctccctta
gtgaagttatggtaccagttagagaaagaacccataataggagcagaaactttctatgtagatggggcagccaataagggaactaaattaggaaaag
caggatatgtaactgacagaggaagacaaaaagttgtccccctaacggacacaacaaatcagaagactgagttacaagcaattcatctagctttgca
ggattcgggattagaagtaaacatagtgacagactcacaatatgcattgggaatcattcaagcacaaccagataagagtgaatcagagttagtcagt
caaataatagagcagttaataaaaaaggaaaagtctacctggcatgggtaccagcacacaaaggaattggaggaaatgaacaagtagatggttgg
tcagtgctggaatcaggaaagtactatttttagatggaataagtaaggcccaagaagaacatgagaaatatcacagtaattggagagcaatggctagt
tgattttaacctaccacctgtagtagcaaaagaaatagtagccagctgtgataaatgtcagctaaaaggagaagccatgcatggacaagtagactgt
agcccaggaatatggcagctagattgtacacatttagaaggaaaagttatcttggtagcagttcatgtagccagtggatatatagaagcagaagtaa
ttccagcagagacagggcaagaaacagcatacttcctcttaaaattagcaggaagatggccagtaaaaacagtacatacagacaatggcagcaattt
caccagtactacagttaaggccgcctgttggtgggcgggatcaagcaggaatttggcattccctacaatccccaaagtcaaggagtaatagaatct
atgaataaagaattaaagaaaattataggacagtaagagatcaggctgaacatcttaagacagcagtacaaatggcagtattcatccacaatttta
aaagaaaaggggggattggggggtacagtgcagggggaagaatagtagacataatagcaacagacatacaaactaaagaattacaaaaacaaattac
aaaaattcaaaattttcgggtttattacagggacagcagagatccagtttggaaaggaccagcaaagctcctctggaaaggtgaagggcagtagta
atacaagataatagtgacataaaagtagtgccaagaagaaaagcaaagatcatcagggattatggaaaacagatggcaggtgatgattgtgtggca

Figure 7

```
agtagacaggatgaggattaacacatggaattccggagcggccgcaggagctttgttccttgggttcttgggagcagcaggaagcactatgggcgca
gcctcaatgacgctgacggtacaggccagacaattattgtctggtatagtgcagcagcagaacaatttgctgagggctattgaggcgcaacagcatc
tgttgcaactcacagtctgtgggcatcaagcagctccaggcaagaatcctggctgtgggaaagatacctaaaggatcaacagctcctgggatttgggg
ttgctctggaaaactcatttgcaccactgctgtgccttggaatgctagttggagtaataaatctctggaacagatttggaatcacacgacctggatg
gagtgggacagagaaattaacaattacacaagcttccgcggaattcaccccaccagtgcaggctgcctatcagaaagtggtggctggtgtggctaat
gccctggcccacaagtttcactaagctcgcttccttgctgtccaatttctattaaaggttccttggttccctaagtccaactactaaactggggat
attatgaaggccttgagcatctggattctgcctaataaaaaacattttattttcattgcaatgatgtatttaaattatttctgaatatttactaaa
aagggaatgtgggaggtcagtgcatttaaaacataaagaaatgaagagctagttcaaaccttgggaaaatacactatatcttaaactccatgaaaga
aggtgaggctgcaaacagctaatgcacattggcaacagccctgatgcctatgcttattcatccctcagaaaaggattcaagtagaggcttgatttg
gaggttaaagtttggctatgctgtattttacattacttattgttttagctgtcctcatgaatgtcttttcactacccatttgcttatcctgcatctc
tcagccttgactccactcagttctcttgcttagagataccaccttccctgaagtgttccttccatgttttacggcgagatggttctcctcgcct
ggccactcagccttagttgtctctgttgtcttatagaggtctacttgaagaaggaaaaacagggggcatggtttgactgtcctgtgagccttcttc
cctgcctccccactcacagtgacccggaatccctcgacatggcagtctagcactagtgcggcgcagatctgcttcctcgctcactgactcgctgc
gctcggtcgttcggctgcggcgagcggtatcagctcactcaaaggcggtaatacggttatccacagaatcaggggataacgcaggaaagaacatgtg
agcaaaaggccagcaaaaggccaggaaccgtaaaaaggccgcgttgctggcgtttttccataggctccgcccccctgacgagcatcacaaaaatcga
cgctcaagtcagaggtggcgaaacccgacaggactataaagataccaggcgtttccccctggaagctccctcgtgcgctctcctgttccgaccctgc
cgcttaccggatacctgtccgcctttctcccttcgggaagcgtggcgctttctcaatgctcacgctgtaggtatctcagttcggtgtaggtcgttcg
ctccaagctgggctgtgtgcacgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaagtggtggcctaactacggct
acactagaaggacagtatttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatcttttctacggggtctgacgct
cagtggaacgaaaactcacgttaagggattttggtcatgagattatcaaaaaggatcttcacctagatccttttaaattaaaaatgaagttttaaat
caatctaaagtatatatgagtaaacttggtctgacagttaccaatgcttaatcagtgaggcacctatctcagcgatctgtctatttcgttcatccat
agttgcctgactccccgtcgtgtagataactacgatacgggagggcttaccatctggccccagtgctgcaatgataccgcgagacccacgctcaccg
gctccagatttatcagcaataaaccagccagccggaagggccgagcgcagaagtggtcctgcaacttatccgcctccatccagtctattaattgtt
gccgggaagctagagtaagtagttcgccagttaatagtttgcgcaacgttgttgccattgctacaggcatcgtggtgtcacgctcgtcgtttggtat
ggcttcattcagctccggttcccaacgatcaaggcgagttacatgatccccatgttgtgcaaaaaagcggttagctccttcggtcctccgatcgtt
gtcagaagtaagttggccgcagtgttatcactcatggttatggcagcactgcataattctcttactgtcatgccatccgtaagatgcttttctgtga
ctggtgagtactcaaccaagtcattctgagaatagtgtatgcggcgaccgagttgctcttgcccggcgtcaatacgggataataccgcgccacatag
cagaactttaaaagtgctcatcattggaaaacgttcttcggggcgaaaactctcaaggatcttaccgctgttgagatccagttcgatgtaacccact
cgtgcacccaactgatcttcagcatcttttactttcaccagcgtttctgggtgagcaaaaacaggaaggcaaatgccgcaaaaaagggaataaggg
cgacacggaaatgttgaatactcatactcttcctttttcaatattattgaagcatttatcagggttattgtctcatgagcggatacatatttgaatg
tatttagaaaaataaacaaataggggttccgcgcacatttccccgaaaagtgccacctgacgt
```

```
gtagacaggatgaggattaacacatggaattccggagcggccgcaggagctttgttccttgggttcttgggagcagcaggaagcactatgggcgcag
cctcaatgacgctgacggtacaggccagacaattattgtctggtatagtgcagcagcagaacaatttgctgagggctattgaggcgcaacagcatct
gttgcaactcacagtctggggcatcaagcagctccaggcaagaatcctggctgtggaaagatacctaaaggatcaacagctcctggggatttggggt
tgctctggaaaactcatttgcaccactgctgtgccttggaatgctagttggagtaataaatctctggaacagatttggaatcacacgacctggatgg
agtgggacagagaaattaacaattacacaagcttccgcggaattcacccaccagtgcaggctgcctatcagaaagtgctggctggtgtggctaatg
ccctggcccacaagtttcactaagctcgcttccttgctgtccaatttctattaaaggttccttggttccctaagtccaactactaaactggggata
ttatgaagggccttgagcatctggattctgcctaataaaaaacatttattttcattgcaatgatgtatttaaattatttctgaatattttactaaaa
agggaatgtgggaggtcagtgcatttaaaacataaagaaatgaagagctagttcaaaccttgggaaaatacactatatcttaaactccatgaaagaa
ggtgaggctgcaaacagctaatgcacattggcaacagccctgatgcctatgccttattcatccctcagaaaaggattcaagtagaggcttgatttgg
aggttaaagtttggctatgctgtatttacattacttattgttttagctgtcctcatgaatgtcttttcactacccatttgcttatcctgcatctct
cagccttgactccactcagttctcttgcttagagataccaccttcccctgaagtgttccttccatgtttttacggcgagatggtttctcctcgcctg
gccactcagccttagttgtctctgttgtcttatagaggtctacttgaagaaggaaaaacaggggcatggtttgactgtcctgtgagccttcttcc
ctgcctccccactcacagtgaccggaatccctcgacatggcagtctagcactagtgcggccgcagatctgcttcctcgctcactgactcgctgcg
ctcggtcgttcggctgcggcgagcggtatcagctcactcaaaggcggtaatacggttatccacagaatcaggggataacgcaggaagaacatgtga
gcaaaaggccagcaaaaggccaggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgctctcctgttccgaccctgcc
gcttaccggatacctgtccgcctttctcccttcgggaagcgtggcgctttctcaatgctcacgctgtaggtatctcagttcggtgtaggtcgttcgc
tccaagctgggctgtgtgcacgaaccccccgttcagcccgaccgctgcgccttatccggtaactatcgtcttgagtccaacccggtaagacacgact
tatcgccactggcagcagccactggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgatccggcaaacaaaccaccgct
ggtagcggtggtttttttgtttgcaagcagcagattacgcgcagaaaaaaaggatctcaagaagatcctttgatcttttctacggggtctgacgctc
agtggaacgaaaactcacgttaagggattttggtcatgagattatcaaaaaggatcttcacctagatccttttaaattaaaaatgaagttttaaatc
aatctaaagtatatatgagtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgataccgcgagacccacgctcaccgg
ctccagatttatcagcaataaaccagccagccggaagggccgagcgcagaagtggtcctgcaactttatccgcctccatccagtctattaattgttg
ccgggaagctagagtaagtagttcgccagttaatagtttgcgcaacgttgttgccattgctacaggcatcgtggtgtcacgctcgtcgtttggtatg
gcttcattcagctccggttcccaacgatcaaggcgagttacatgatccccatgttgtgcaaaaaagcggttagctccttcggtcctccgatcgttg
tcagaagtaagttggccgcagtgttatcactcatggttatggcagcactgcataattctcttactgtcatgccatccgtaagatgcttttctgtgac
tggtgagtactcaaccaagtcattctgagaatagtgtatgcggcgaccgagttgctcttgcccggcgtcaatacgggataataccgcgccacatagc
agaactttaaaagtgctcatcattggaaaacgttcttcggggcgaaaactctcaaggatcttaccgctgttgagatccagttcgatgtaacccactc
gtgcacccaactgatcttcagcatcttttactttcaccagcgtttctgggtgagcaaaaacaggaaggcaaaatgccgcaaaaaagggaataagggc
gacacggaaatgttgaatactcatactcttcctttttcaatattattgaagcatttatcagggttattgtctcatgagcggatacatatttgaatgt
atttagaaaaataaacaaataggggttccgcgcacatttccccgaaaagtgccacctgacgt
```

```
gtagacaggatgaggattaacacatggaattccggagcggccgcaggagctttgttccttgggttcttgggagcagcaggaagcactatgggcgcag
cctcaatgacgctgacggtacaggccagacaattattgtctggtatagtgcagcagcagaacaatttgctgagggctattgaggcgcaacagcatct
gttgcaactcacagtctgggcatcaagcagctccaggcaagaatcctggctgtggaaagatacctaaaggatcaacagctcctgggatttggggt
tgctctggaaaactcatttgcaccactgctgtgccttggaatgctagtttggagtaataaatctctggaacagatttggaatcacacgacctggatgg
agtgggacagagaaattaacaattacacaagcttccgcggaattcaccccaccagtgcaggctgcctatcagaaagtggtggctggtgtggctaatg
ccctggcccacaagtttcactaagctcgcttccttgctgtccaatttctattaaaggttccttggttccctaagtccaactactaaactgggggata
ttatgaagggccttgagcatctggattctgcctaataaaaaacatttattttcattgcaatgatgtatttaaattatttctgaatattttactaaaa
agggaatgtgggaggtcagtgcatttaaaacataaagaaatgaagagctagttcaaaccttgggaaaatacactatatcttaaactccatgaaagaa
ggtgaggctgcaaacagctaatgcacattggcaacagccctgatgcctatgccttattcatccctcagaaaaggattcaagtagaggcttgatttgg
aggttaaagtttggctatgctgtattttacattacttattgttttagctgtcctcatgaatgtcttttcactaccatttgcttatcctgcatctct
cagccttgactccactcagttctcttgcttagagataccacctttcccctgaagtgttcttccatgtttacgcgagatggtttctcctcgcctg
gccactcagccttagttgtctctgttgtcttatagaggtctacttgaagaaggaaaaacaggggggcatggtttgactgtcctgtgagccccttcttcc
ctgcctcccccactcacagtgaccggaatccctcgacatggcagtctagcactagtgcggccgcagatctgcttcctcgctcactgactcgctgcg
ctcggtcgttcggctgcggcgagcggtatcagctcactcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgctctcctgttccgaccctgcc
gcttaccggatacctgtccgcctttctcccttcgggaagcgtggcgctttctcaatgctcacgctgtaggtatctcagttcggtgtaggtcgttcgc
tccaagctgggctgtgtgcacgaaccccccgttcagcccgaccgctgcgccttatccggtaactatcgtcttgagtccaacccggtaagacacgact
tatcgccactggcagcagccactggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgatccggcaaacaaaccaccgct
ggtagcggtggtttttttgtttgcaagcagcagattacgcgcagaaaaaaaggatctcaagaagatcctttgatcttttctacggggtctgacgctc
agtggaacgaaaactcacgttaagggattttggtcatgagattatcaaaaaggatcttcacctagatcctttttaaattaaaaatgaagttttaaatc
aatctaaagtatatatgagtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgataccgcgagacccacgctcaccgg
ctccagatttatcagcaataaaccagccagccggaagggccgagcgcagaagtggtcctgcaactttatccgcctccatccagtctattaattgttg
ccgggaagctagagtaagtagttcgccagttaatagtttgcgcaacgttgttgccattgctacaggcatcgtggtgtcacgctcgtcgtttggtatg
gcttcattcagctccggttcccaacgatcaaggcgagttacatgatccccatgttgtgcaaaaaagcggttagctccttcggtcctccgatcgttg
tcagaagtaagttggccgcagtgttatcactcatggttatggcagcactgcataattctcttactgtcatgccatccgtaagatgcttttctgtgac
tggtgagtactcaaccaagtcattctgagaatagtgtatgcggcgaccgagttgctcttgcccggcgtcaatacgggataataccgcgccacatagc
agaactttaaaagtgctcatcattggaaaacgttcttcggggcgaaaactctcaaggatcttaccgctgttgagatccagttcgatgtaacccactc
gtgcacccaactgatcttcagcatcttttactttcaccagcgtttctgggtgagcaaaaacaggaaggcaaaatgccgcaaaaaagggaataagggc
gacacggaaatgttgaatactcatactcttcctttttcaatattattgaagcatttatcagggttattgtctcatgagcggatacatatttgaatgt
atttagaaaaataaacaaataggggttccgcgcacatttccccgaaaagtgccacctgacgt
```

Figure 9 (cont.)

A.
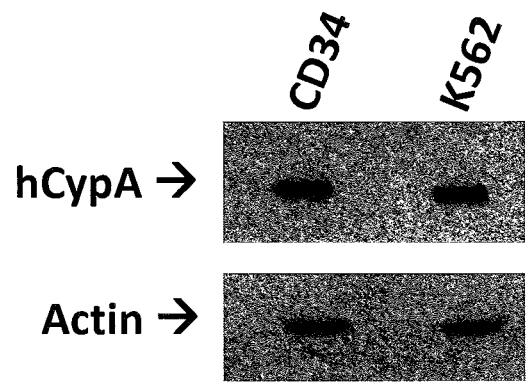
hCypA →
Actin →
B.
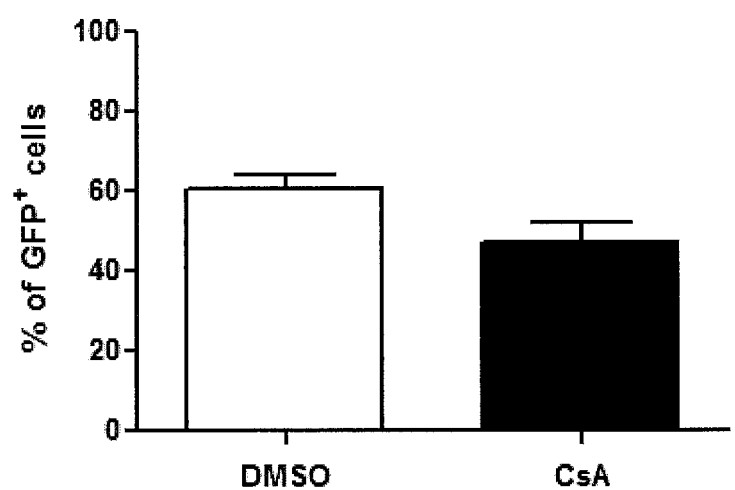
Figure 13

A.
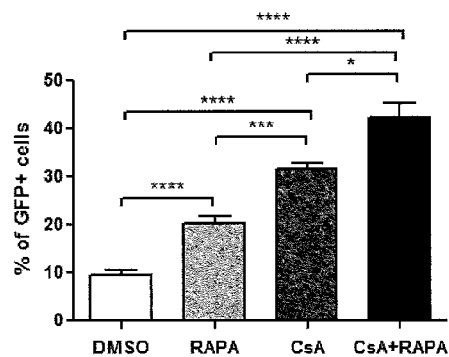
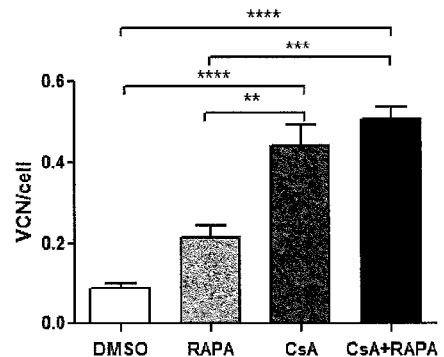
B.
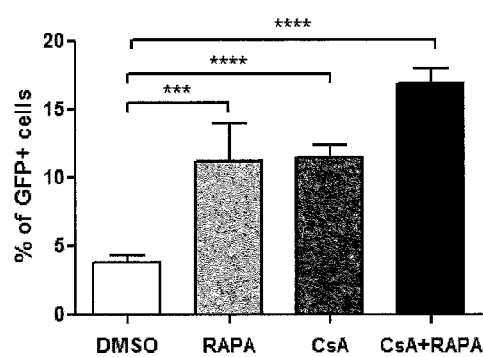
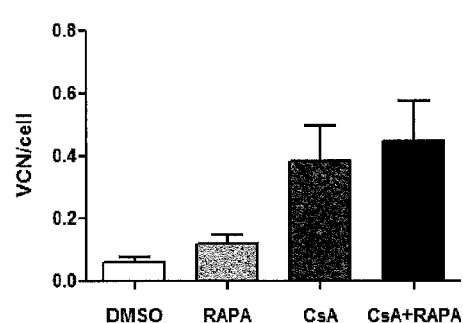
C.
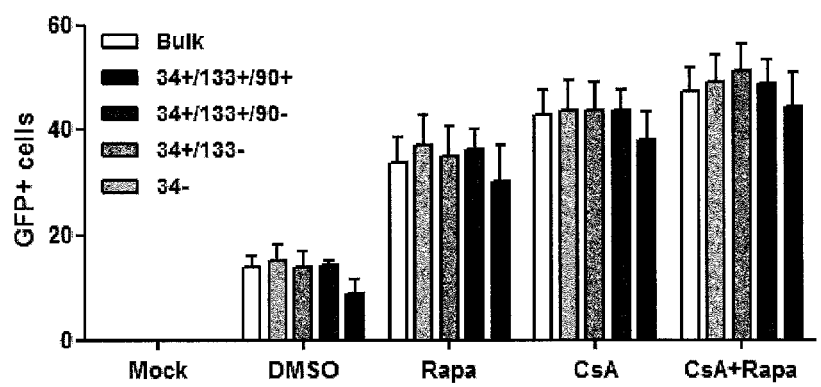
Figure 15

A.
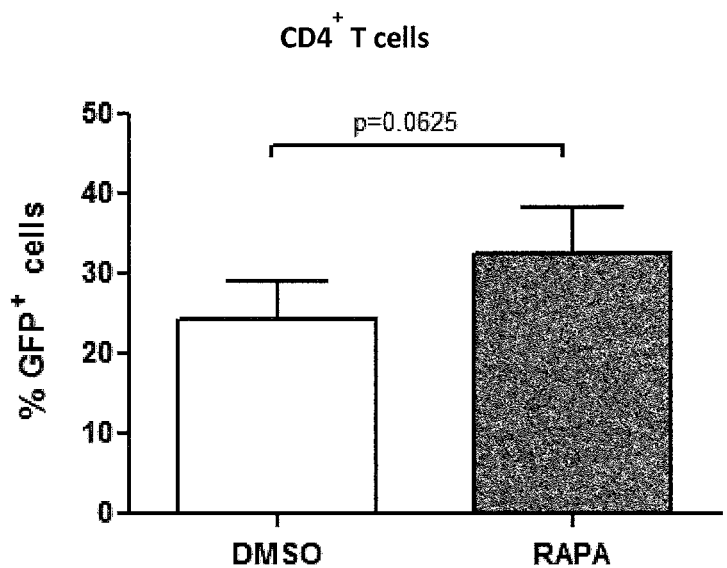
B.
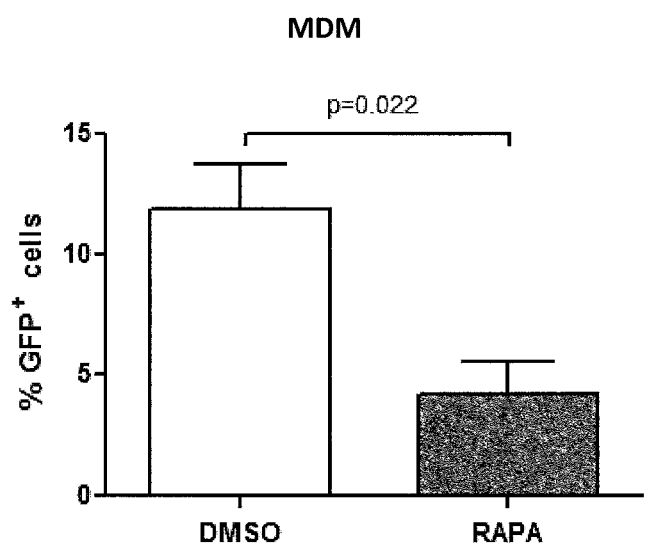
Figure 16

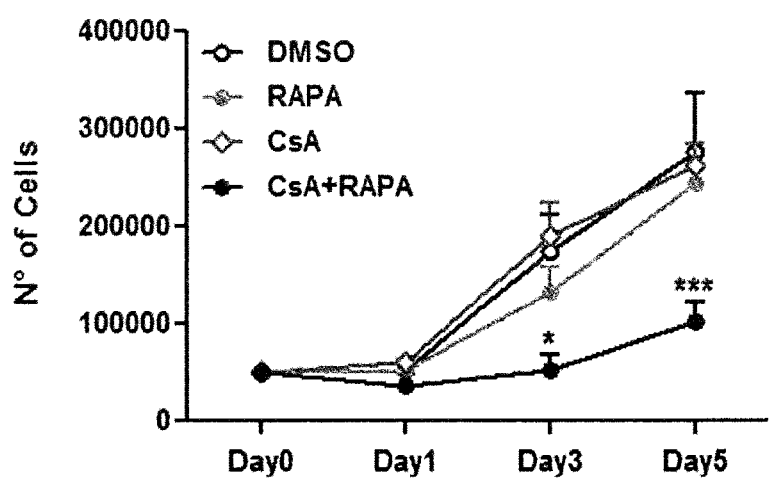
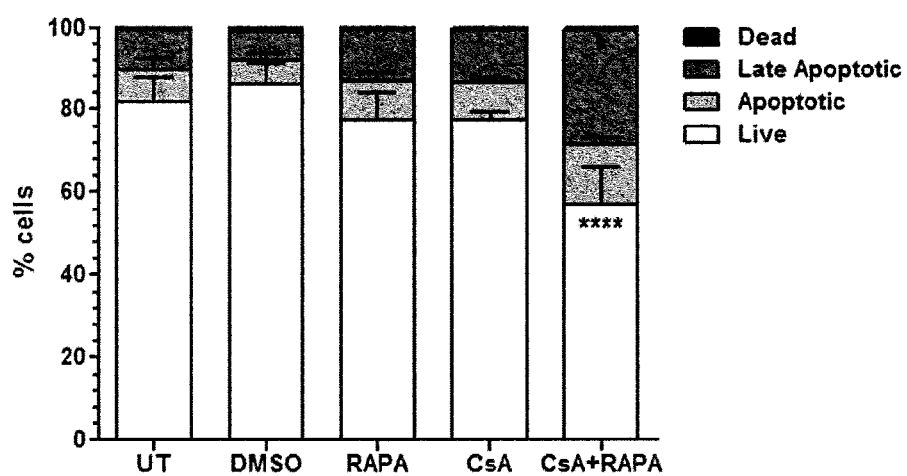
Figure 18

A.
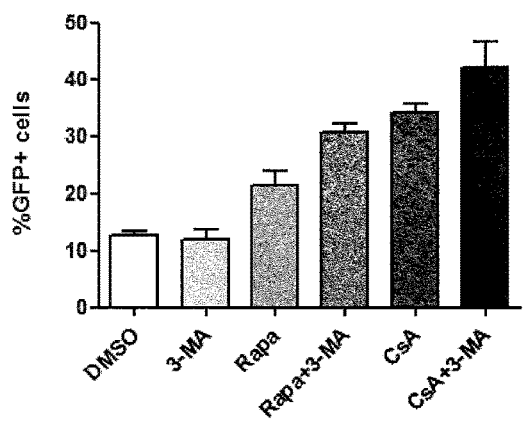 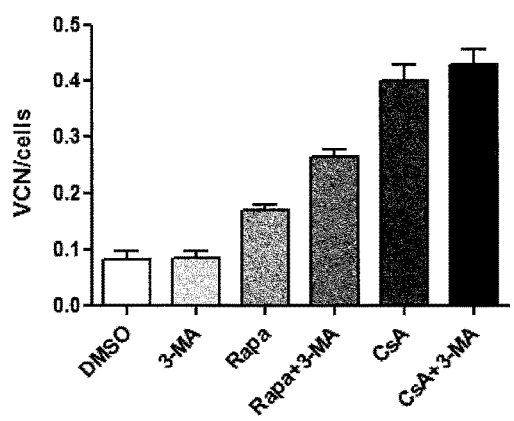
B.
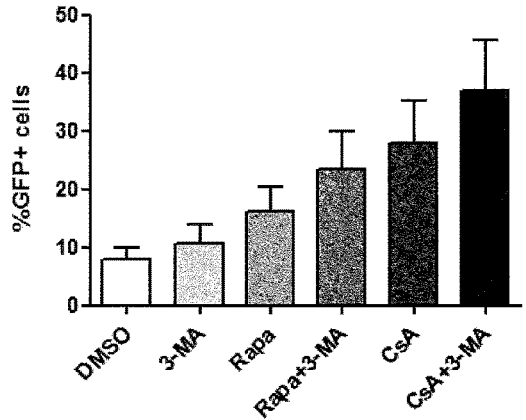 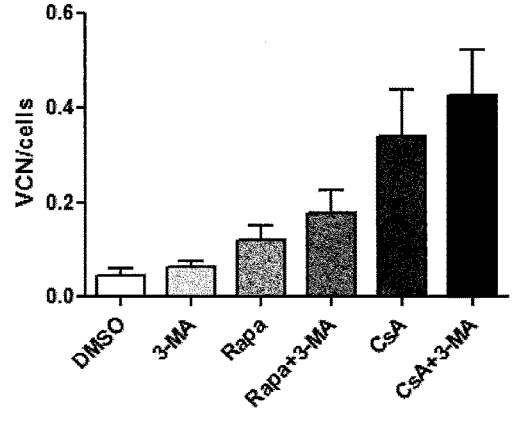
Figure 19

A. CB
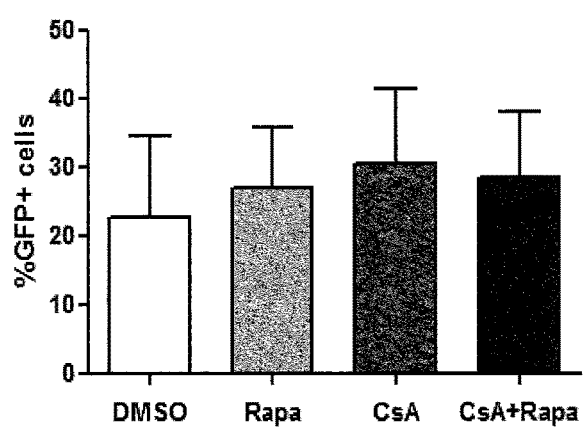
B. BM
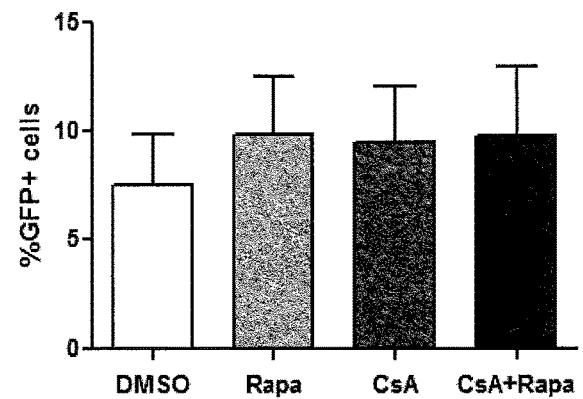
Figure 24

A. CB
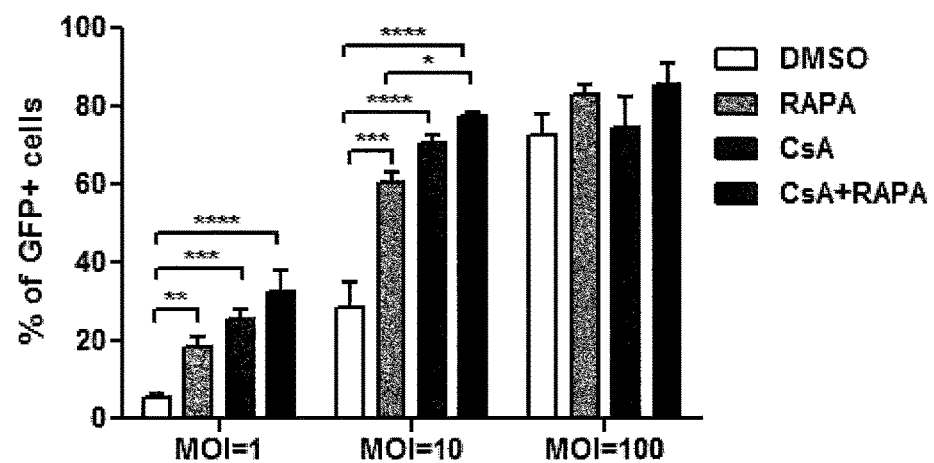
B.
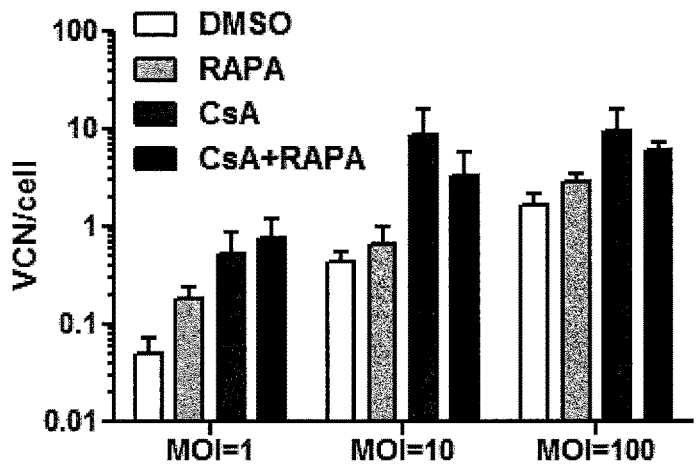
Figure 25

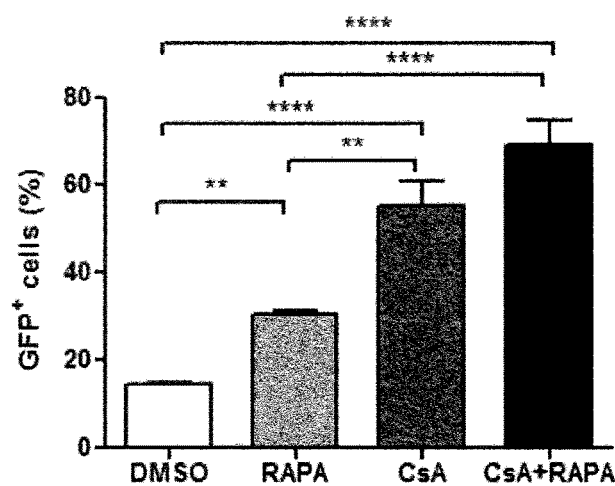
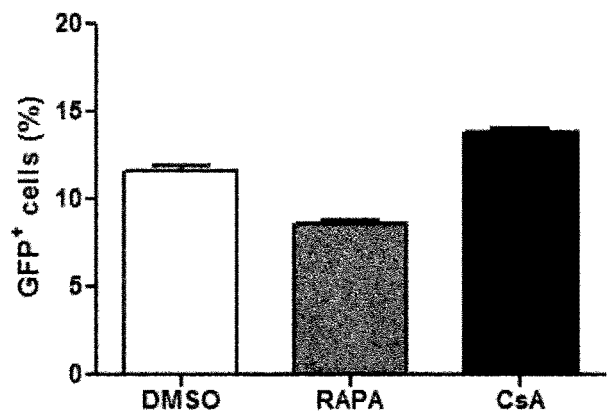
Figure 29

GENE THERAPY

FIELD OF THE INVENTION

The present invention relates to the genetic modification of haematopoietic stem and progenitor cells. More specifically, the present invention relates to the use of compounds to improve the transduction of haematopoietic stem and progenitor cells by lentiviral vectors.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage. HSCs have the ability to replenish the entire haematopoietic system.

Haematopoietic cell transplantation (HCT) is a curative therapy for several inherited and acquired disorders. However, allogeneic HCT is limited by the poor availability of matched donors, the mortality associated with the allogeneic procedure which is mostly related to graft-versus-host disease (GvHD), and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This ensures a continuous supply of corrected cells for the rest of the patient's lifetime. HSCs are particularly attractive targets for gene therapy since their genetic modification will be passed to all the blood cell lineages as they differentiate. Furthermore, HSCs can be easily and safely obtained, for example from bone marrow, mobilised peripheral blood and umbilical cord blood.

Efficient long-term gene modification of HSCs and their progeny requires a technology which permits stable integration of the corrective DNA into the genome, without affecting HSC function. Accordingly, the use of integrating recombinant viral systems such as γ-retroviruses, lentiviruses and spumaviruses has dominated this field (Chang, A. H. et al. (2007) *Mol. Ther.* 15: 445-56). Therapeutic benefits have already been achieved in γ-retrovirus-based clinical trials for Adenosine Deaminase Severe Combined Immunodeficiency (ADA-SCID; Aiuti, A. et al. (2009) *N. Engl. J. Med.* 360: 447-58), X-linked Severe Combined Immunodeficiency (SCID-X1; Hacein-Bey-Abina, S. et al. (2010) *N. Engl. J. Med.* 363: 355-64) and Wiskott-Aldrich syndrome (WAS; Bortug, K. et al. (2010) *N. Engl. J. Med.* 363: 1918-27). In addition, lentiviruses have been employed as delivery vehicles in the treatment of X-linked adrenoleukodystrophy (ALD; Cartier, N. et al. (2009) *Science* 326: 818-23), and very recently for metachromatic leukodystrophy (MLD; Biffi, A. et al. (2013) *Science* 341: 1233158) and WAS (Aiuti, A. et al. (2013) *Science* 341: 1233151).

Nevertheless, although lentiviruses are among the best available platforms for stem cell transduction, significant difficulties remain with the methods employed for the genetic modification of haematopoietic stem and progenitor cells.

In particular, the existing methods exhibit suboptimal target cell permissivity as high vector doses, prolonged transduction times and ex vivo culture are still required to reach clinically relevant transduction levels. This remains a significant hurdle for the field as it implies cumbersome, costly and not always sustainable large-scale vector productions and compromised cell quality due to prolonged ex vivo transduction protocols.

The prior art indicates that cyclosporin A (CsA) has a detrimental effect on the transduction of human $CD34^+$ cells. For example, Santoni de Sio, F. R. et al. (2008) *Stem Cells* 26: 2142-52; Kahl, C. A. et al. (2008) *Gene Therapy* 15: 1079-89; and Uchida, N. et al. (2013) *Exp. Hematol.* 41: 779-88 e771 all teach that CsA decreases the transduction efficiency of HIV-1-derived vectors in human $CD34^+$ cells.

SUMMARY OF THE INVENTION

Contrary to the perceived understanding in the art, we have shown that cyclosporin A (CsA) increases the efficiency of transduction of haematopoietic stem and/or progenitor cells by lentiviral vectors. We have also shown that this effect may be further increased by using combinations of CsA and rapamycin and/or 3-methyladenine (3-MA).

In addition, we have identified two amino acid positions in the lentiviral capsid which have an impact on the efficiency of transduction of haematopoietic stem and/or progenitor cells by lentiviral vectors. In particular, we have discovered that if specific amino acids are present at these positions, the efficiency of transduction is increased.

In one aspect, the present invention provides a use of cyclosporin A (CsA) or a derivative thereof for increasing the efficiency of transduction of an isolated population of human haematopoietic stem and/or progenitor cells by a vector derived from HIV-1, HIV-2, FIV, BIV, EIAV, CAEV or visna lentivirus.

In one embodiment, the percentage of haematopoietic stem and/or progenitor cells transduced by the vector is increased. In another embodiment, the vector copy number per cell is increased. Both the percentage of haematopoietic stem and/or progenitor cells transduced by the vector and the vector copy number per cell may be increased at the same time.

In one embodiment, the vector is derived from HIV-1. The HIV-1-derived vector may be, for example, derived from any of the HIV-1 strains NL4-3, IIIB_LAI or HXB2_LAI (X4-tropic), or BAL (R5-tropic), or a chimaera thereof. The HIV-1-derived vector may be derived from the pMDLg/pRRE Gag-Pol-expressing packaging construct.

In one embodiment, the vector may be an integration-defective lentiviral vector (IDLV), for example an integration-defective vector derived from HIV-1.

The vector may be a wild-type vector.

In a preferred embodiment, the vector derived from HIV-1 excludes a vector which comprises a capsid protein or a gene encoding for a capsid protein which comprises proline at position 86, glutamine at position 87, valine at position 91 and isoleucine at position 96.

Vectors derived from SIV are not included in the present invention. The present invention does not encompass vectors comprising SIV-derived capsid proteins.

In one embodiment, the vector is "matched" to the host cell. By "matched" it is to be understood that the vector capsid is derived from a virus which naturally infects a certain type of host (for example, HIV capsids are "matched" to humans). Therefore, in one embodiment, a vector for use in human haematopoietic stem and/or progenitor cells does not comprise capsid proteins other than those derived from a human immunodeficiency virus.

In one embodiment, the vector, for example an HIV-1-derived vector, comprises a capsid comprising glutamic acid at position 92. In another embodiment, the vector may comprise a capsid comprising threonine at position 88. In another embodiment, the vector may comprise a capsid comprising both glutamic acid at position 92 and threonine at position 88. For example, the vector may be derived from the pMDLg/pRRE Gag-Pol-expressing packaging construct. Such a vector may harbour an A88T mutation, an A92E mutation or an A88T/A92E double mutation in its capsid protein.

In one embodiment, the CsA or a derivative thereof may be used at a concentration of about 5-50 µM and more preferably about 10-50 µM. In one embodiment, the concentration of CsA or a derivative thereof is about 5-40 µM. In a preferred embodiment, the concentration of CsA or a derivative thereof is about 10-40 µM. In a more preferred embodiment, the concentration of CsA or a derivative thereof is about 10-25 µM. In a particularly preferred embodiment, the concentration of CsA or a derivative thereof is about 10-15 µM.

For example the concentration of CsA may be about 5, 6, 7, 8, 9, 10, 11, 12, 13, 14, 15, 20, 25, 30, 35, 40, 45 or 50 µM. In a preferred embodiment, the concentration of CsA or a derivative thereof is about 10, 11, 12, 13, 14 or 15 µM. In a particularly preferred embodiment, the concentration of CsA or a derivative thereof is about 10 µM.

In one embodiment, the cyclosporin A (CsA) or a derivative thereof may be used in combination with rapamycin. In another embodiment, the cyclosporin A (CsA) or a derivative thereof may be used in combination with 3-methyladenine (3-MA). The cyclosporin A (CsA) or a derivative thereof may also be in combination with both rapamycin and 3-methyladenine (3-MA).

In another aspect, the present invention provides a method of transducing a population of human haematopoietic stem and/or progenitor cells comprising the steps of:
 a) contacting the population of cells with cyclosporin A (CsA) or a derivative thereof; and
 b) transducing the population of cells with a vector derived from HIV-1, HIV-2, FIV, BIV, EIAV, CAEV or visna lentivirus.

In one embodiment, steps (a) and (b) of the method are carried out ex vivo or in vitro.

In one embodiment, the percentage of haematopoietic stem and/or progenitor cells transduced by the vector is increased. In another embodiment, the vector copy number per cell is increased. Both the percentage of haematopoietic stem and/or progenitor cells transduced by the vector and the vector copy number per cell may be increased at the same time.

In one embodiment, the vector is derived from HIV-1. The HIV-1-derived vector may be, for example, derived from any of the HIV-1 strains NL4-3, IIIB_LAI or HXB2_LAI (X4-tropic), or BAL (R5-tropic), or a chimaera thereof. The HIV-1-derived vector may be derived from the pMDLg/pRRE Gag-Pol-expressing packaging construct.

In one embodiment, the vector may be an integration-defective lentiviral vector (IDLV), for example an integration-defective vector derived from HIV-1.

The vector may be a wild-type vector.

In one embodiment, the vector is "matched" to the host cell. Therefore, in one embodiment, a vector for use in human haematopoietic stem and/or progenitor cells does not comprise capsid proteins other than those derived from a human immunodeficiency virus.

In one embodiment, the vector, for example an HIV-1-derived vector, comprises a capsid comprising glutamic acid at position 92. In another embodiment, the vector may comprise a capsid comprising threonine at position 88. In another embodiment, the vector may comprise a capsid comprising both glutamic acid at position 92 and threonine at position 88. For example, the vector may be derived from the pMDLg/pRRE Gag-Pol-expressing packaging construct. Such a vector may harbour an A88T mutation, an A92E mutation or an A88T/A92E double mutation in its capsid protein.

In one embodiment, the concentration of CsA or a derivative thereof applied to the population of haematopoietic stem and/or progenitor cells may be about 5-50 µM and more preferably about 10-50 µM. In one embodiment, the concentration of CsA or a derivative thereof is about 5-40 µM. In a preferred embodiment, the concentration of CsA or a derivative thereof is about 10-40 µM. In a more preferred embodiment, the concentration of CsA or a derivative thereof is about 10-25 µM. In a particularly preferred embodiment, the concentration of CsA or a derivative thereof is about 10-15 µM.

For example the concentration of CsA may be about 5, 6, 7, 8, 9, 10, 11, 12, 13, 14, 15, 20, 25, 30, 35, 40, 45 or 50 µM. In a preferred embodiment, the concentration of CsA or a derivative thereof is about 10, 11, 12, 13, 14 or 15 µM. In a particularly preferred embodiment, the concentration of CsA or a derivative thereof is about 10 µM.

In one embodiment, the population of cells may be contacted with cyclosporin A (CsA) or a derivative thereof in combination with rapamycin. In another embodiment, the population of cells is contacted with cyclosporin A (CsA) or a derivative thereof in combination with 3-methyladenine (3-MA). The population of cells may be contacted with cyclosporin A (CsA) or a derivative thereof in combination with both rapamycin and 3-methyladenine (3-MA).

In one embodiment, the population of haematopoietic stem and/or progenitor cells may be obtained from mobilised peripheral blood, bone marrow or umbilical cord blood.

The method may include a further step of enriching the population for haematopoietic stem and/or progenitor cells. The step of enriching the population for haematopoietic stem and/or progenitor cells may be carried out before contacting the population of cells with cyclosporin A (CsA) or a derivative thereof. Alternatively, or additionally, the step of enriching the population for haematopoietic stem and/or progenitor cells may be carried out after transducing the population of cells with a vector.

The method may also include wash steps. The wash step may be used to substantially remove the cyclosporin A (CsA) or derivative thereof from the medium. The wash step may be carried out after transducing the population of cells with a vector. Alternatively, or additionally, the wash step may be carried out before transducing the cells.

In another aspect, the present invention provides a method of gene therapy comprising the steps of:
 a) transducing a population of human haematopoietic stem and/or progenitor cells according to a method of the invention; and
 b) administering the transduced cells to a subject.

The transduced cells may be administered to a subject as part of an autologous stem cell transplant procedure or an allogeneic stem cell transplant procedure.

In another aspect, the present invention provides a population of human haematopoietic stem and/or progenitor cells prepared according to a method of the invention.

In another aspect, the present invention provides a pharmaceutical composition comprising a population of haematopoietic stem and/or progenitor cells of the invention.

In another aspect, the present invention provides a population of haematopoietic stem and/or progenitor cells for use in therapy.

The population of haematopoietic stem and/or progenitor cells for use in therapy may be administered as part of an autologous stem cell transplant procedure or an allogeneic stem cell transplant procedure.

In another aspect, the present invention provides cyclosporin A (CsA) or a derivative thereof for use in haematopoietic stem and/or progenitor cell gene therapy.

In another aspect, the present invention provides a method of transducing a population of haematopoietic stem and/or progenitor cells with a vector derived from HIV-1, HIV-2, FIV, BIV, EIAV, CAEV or visna lentivirus, wherein the vector comprises a capsid comprising glutamic acid at position 92 and/or threonine at position 88.

The transduction may carried out ex vivo or in vitro. The haematopoietic stem and/or progenitor cells may be human.

In one embodiment, the vector is derived from HIV-1. The HIV-1-derived vector may be derived from any of the HIV-1 strains NL4-3, IIIB_LAI or HXB2_LAI (X4-tropic), or BAL (R5-tropic), or a chimaera thereof. The HIV-1-derived vector may be derived from the pMDLg/pRRE Gag-Pol-expressing packaging construct.

For example, the vector may be derived from the pMDLg/pRRE Gag-Pol-expressing packaging construct. Such a vector may harbour an A88T mutation, an A92E mutation or an A88T/A92E double mutation in its capsid protein.

In one embodiment, the vector may be an integration-defective lentiviral vector (IDLV), for example an integration-defective vector derived from HIV-1.

In another aspect, the present invention provides a use of an HIV-1, HIV-2, FIV, BIV, EIAV, CAEV or visna lentivirus-derived capsid mutant for increasing the efficiency of transduction of an isolated population of haematopoietic stem and/or progenitor cells by a vector derived from HIV-1, HIV-2, FIV, BIV, EIAV, CAEV or visna lentivirus in comparison to a vector lacking said mutation, wherein the capsid mutant comprises glutamic acid at position 92 and/or threonine at position 88.

DESCRIPTION OF THE DRAWINGS

FIG. 1 pMDLg/pRRE complete vector sequence. The Gag ORF is highlighted in grey. The "wild-type (WT)" capsid (CA or p24) CDS is highlighted in bold with underlining.

FIG. 2

Figure 10:
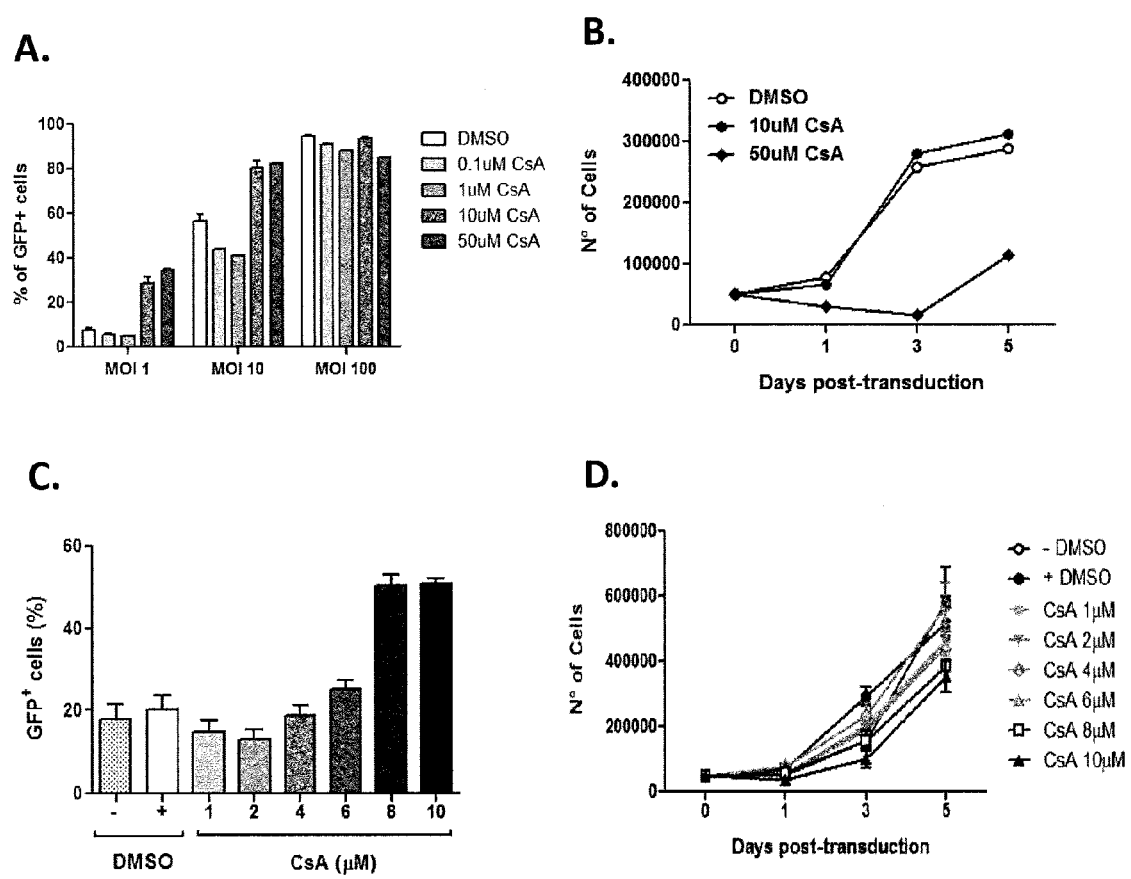

Gag ORF from pMDLg/pRRE. The capsid (CA or p24) CDS is highlighted in grey.

FIG. 3

Capsid (CA or p24) CDS from pMDLg/pRRE.

FIG. 4

Capsid (CA or p24) protein sequence encoded by pMDLg/pRRE.

FIG. 5

Sequence alignments of the p24 amino acid sequences of the WT packaging construct (pMDL) with the clade B HIV-1 laboratory strains: (a) IIIB_LAI (X4-tropic); (b) HXB2_LAI (X4-tropic); (c) BAL (R5-tropic); and (d) the infectious molecular clone pNL4.3.

FIG. 6

Capsid (CA or p24) protein sequence encoded by pMDLg/pRRE. The position of amino acid residues 92 and 88 is highlighted in grey.

FIG. 7 pMDLg/pRRE Gag-Pol-expressing packaging construct incorporating an example mutation corresponding to a capsid A88T mutant.

FIG. 8 pMDLg/pRRE Gag-Pol-expressing packaging construct incorporating an example mutation corresponding to a capsid A92E mutant.

FIG. 9 pMDLg/pRRE Gag-Pol-expressing packaging construct incorporating an example mutation corresponding to a capsid A88T/A92E double mutant.

FIG. 10

Optimal conditions for CsA effect in human HSPC. Cord blood (CB)-derived CD34$^+$ cells were exposed to SINLV-GFP at increasing multiplicities of infection (MOI) in the presence or absence of increasing concentrations of CsA. The percentage of GFP+ cells was measured by FACS 5 days post-transduction (A, C). The number of cells was assessed by crude cell count over time (B, D). Data represent the mean±SEM of two independent experiments.

FIG. 11

CsA increases lentiviral (LV) transduction efficiency specifically in human HSPC. CB and bone marrow (BM)-derived CD34$^+$ cells (A, B), CD4$^+$ T cells (C) and monocyte-derived macrophages (MDM) (D) were exposed to the SINLV-GFP at a MOI of 1, in the presence or absence of 10 μM CsA. A, C, D. The percentage of GFP+ cells was evaluated by flow cytometry (FACS) 5 days after transduction. B. Vector copy numbers (VCN) were assessed by qPCR 14 days post-transduction in CB (left panel) and BM-derived CD34$^+$ cells (right panel). Data represent the mean±SEM of at least six independent experiments. p values are for paired Student's t-test. E. CypA protein levels in CB-derived CD34$^+$ and CD4$^+$ T cells were analysed by Western blot, actin was used as normaliser. F. CypA mRNA was detected from total RNA by qPCR. Data are represented as fold differences v. one of the two CB-CD34$^+$ donors.

FIG. 12

The effect of CsA does not depend on calcineurin-mediated immunosuppression. CB and BM-derived CD34$^+$ cells (A, B), CD4$^+$ T cells (C) and monocyte-derived macrophages (MDM) (D) were exposed to the SINLV-GFP at a MOI of 1, in the presence or absence of 10 μM CsA or 20 μm FK506. A, B (left panel), C, D. The percentage of GFP+ cells was evaluated by FACS five days after transduction. A, B (right panel). VCN were assessed 14 days post-transduction in CB and BM respectively. Data represent the mean±SEM of at least three independent experiments. p values are for One way Anova with Bonferroni multiple comparison.

FIG. 13

Impact of CsA on LV transduction in K562. A. CypA protein levels in K562 and CB-derived CD34$^+$ cells were detected by WB, actin was used as normaliser. B. K562 cells were exposed to SINLV-GFP at a MOI of 1, in the presence or absence of 10 μM CsA. The percentage of GFP+ cells was evaluated by FACS five days after transduction. Data represent the mean±SEM of six independent experiments.

FIG. 14

Impact of CA mutations on CsA/rapamycin (Rapa)-mediated effects on LV transduction. CD4+ T (A) and CB-derived CD34+ cells (B) were transduced with SINLVs harbouring single CA point mutations at a MOI of 1 in the presence or absence of 10 μM CsA. The percentage of GFP+ cells was evaluated by FACS 5 days post-transduction. Data represent the mean±SEM of at least three independent experiments. P values are for one-way ANOVA with Bonferroni's multiple comparison versus WT.

FIG. 15

Impact of CsA, rapamycin (Rapa) and their combination on HSPC transduction. CB (A, C) and BM-derived (B) CD34+ cells were exposed to the SINLV-GFP at a MOI of 1, in the presence or absence of 10 μM CsA or 10 μg/mL rapamycin or their combination. A, B (left panel). The percentage of GFP+ cells was evaluated by FACS five days after transduction. A, B (right panel). VCN were assessed 14 days post-transduction in CB and BM, respectively. Data represent the mean±SEM of at least three independent experiments. p value are for One way ANOVA with Bonferonni's multiple comparison. C. In CB-derived cells the percentage of GFP+ cells within the different subpopulation was evaluated by FACS three days after transduction. Data represent the mean±SEM of five independent experiments.

FIG. 16

Impact of Rapa on LV transduction in CD4+ T cells and MDM. CD4+ T cells (A) and MDM (B) were exposed to the SINLV-GFP at a MOI of 1, in the presence or absence of 10 μg/mL rapamycin. The percentage of GFP+ cells was evaluated by FACS five days after transduction. Data represent the mean±SEM of five independent experiments. p values are for Student's t-test.

FIG. 17

Impact of CsA and Rapa on HSPC subpopulation composition. CB-derived CD34+ cells were exposed to the SINLV-GFP at a MOI of 1, in the presence or absence of 10 μM CsA or 10 μg/mL rapamycin or their combination. The percentages of the different subpopulations were assessed, using the gating strategy shown in A, by FACS three days after transduction (B). Data represent the mean±SEM of five independent experiments.

FIG. 18

The combination of CsA and Rapa leads to some toxicity in HSPC. CB-derived CD34+ cells were exposed to the SINLV-GFP at a MOI of 1, in the presence or absence of 10 μM CsA or 10 μg/mL rapamycin or their combination. A. Cell count over time was performed and data are the mean±SEM of four independent experiments. p values are for Two-way ANOVA with Bonferonni's multiple comparison v. DMSO. B. Annexin staining for apoptotic cells was performed two days after transduction by FACS. Data represent the mean±SEM of three independent experiments. p values are for Two way Anova.

FIG. 19

Inhibition of autophagy enhances both CsA and Rapa-mediated improvement of transduction. CB (A) and BM-derived (B) CD34+ cells were exposed to the SINLV-GFP at a MOI of 1, in the presence or absence of 10 μM CsA or 10 μg/mL rapamycin or 5 mM 3-MA or their combination. Left panels, The percentage of GFP+ cells was evaluated by FACS five days after transduction. Right panels, VCN were assessed 14 days post-transduction. Data represent the mean±SEM of three independent experiments.

FIG. 20

Impact of CsA and Rapa on haematopoietic cell subsets BM and Spleen at 20 weeks post-transplant. A, C. Percentages of the indicated haematopoietic populations within human CD45+ cells in BM (A) and spleen (C). B, D. Frequency of GFP expression in the indicated haematopoietic subpopulations in BM (B) and spleen (D). All values are expressed as mean±SD.

FIG. 21

Impact of CsA and Rapa on colony-forming capacity of human HSPCs. CB-derived CD34+ cells were exposed to the SINLV-GFP at a MOI of 10, in the presence or absence of 10 μM CsA or 10 μg/mL rapamycin or their combination, followed by plating of vital cells the day after in semi-solid methylcellulose. A. CFU count was performed 14 days after plating. B, C. The percentage of myeloid (CD33) and erythroid (CD235) progenitors was measured by FACS after 15 days of culture together with the percentage of GFP+ cells within the different progenitors. Data represent the mean±SEM of four independent experiments. No significant differences were observed with One way Anova analysis. D. Increased transduction efficiency was confirmed by measurement of VCN per cell on bulk colonies isolated after 14 days of culture.

FIG. 22

Impact of CsA and Rapa on transduction efficiency and engraftment capacity of HPSCs in vivo. A-C. Blood analyses in NSG mice at 11 weeks post-transplant: A) engraftment levels evaluated as percent of human CD45+ cells over the total of blood mononuclear cells (y-axis) in mice from different treatment groups (indicated in x-axis), B) percentages of human B, T and myeloid cell lineages (hCD19+, hCD3+ and hCD33+, respectively) within human CD45+ cells and, C) frequency of GFP+ cells (y-axis) within the indicated haematopoietic lineages (x-axis). D-F. Analyses of the BM of NSG mice at 20 weeks post-transplant: D) engraftment levels of human CD45+ cells, E) VCN and F) percentages of the indicated haematopoietic populations within human CD45+ cells. G-H) Analyses of the Spleen of NSG mice 20 weeks post-transplant: G) engraftment levels of human CD45+ cells, and H) frequency of GFP+ cells within hCD45+ cells. All values are expressed as mean±SEM.

FIG. 23

In vitro transduction efficiency of transplanted HSPCs in NSG-mice. A. The percentage of GFP+ cells was evaluated by FACS five days after transduction. B. VCN were assessed 14 days post-transduction. Data are representative of two independent experiments.

FIG. 24

Effects of CsA and Rapa are lentivirus specific. CB (A) and BM-derived (B) CD34+ cells were exposed to the SINRV-GFP at a MOI of 10, in the presence or absence of 10 μM CsA or 10 μg/mL rapamycin or their combination. A, B. The percentage of GFP+ cells was evaluated by FACS five days after transduction. Data represent the mean±SEM of four independent experiments.

FIG. 25

Impact of CsA and Rapa on transduction of human HSPCs with a clinical grade vector. CB-derived CD34+ cells were exposed to a clinical grade SINLV-GFP at a MOI of 10, in the presence or absence of 10 μM CsA or 10 μg/mL rapamycin or their combination. A. The percentage of GFP+ cells was evaluated by FACS five days after transduction. B. VCN were assessed 14 days post-transduction. Data represent the mean±SEM of four independent experiments. p values are for One way Anova with Bonferroni multiple comparison.

FIG. 26

IFNα levels in supernatants from HSPC transduced in the presence of the agents. Supernatants from CB-derived CD34+ cells were harvested 24 hours post-transduction with SINRV-GFP at a MOI of 10, in the presence or absence of 10 μM CsA or 10 μg/mL rapamycin or their combination. IFNα concentration was assessed using the VeriKine™ Human IFN Alpha ELISA Kit. HUVEC-10 cells were used as a positive control and the medium in which the cells were cultured as the negative control. Data represent the mean±SEM of three independent experiments.

FIG. 27

CsA and rapamycin act on distinct steps on the LV life cycle. Cord blood (CB)-derived CD34+ cells were transduced with WT or A92E SINLVGFP at an MOI of 10 (A-C) or an IDLV harboring WT CA at an MOI of 50 (D), in presence or absence of 10 μmol/l CsA or 10 μg/ml rapamycin. The LV genome fate was tracked by measuring late-RT product (A) and 2LTR circles (B) 24 hours after transduction and integrated proviral copies 2 weeks after transduction (C). Data represent the mean±SEM of four independent experiments expressed as fold versus DMSO WT (A,B) or as absolute copies/cell (C). D. IDLV transduction efficiency was measured 3 days after transduction by FACS and by measuring the retrotranscribed LV DNA products by PCR. Data are the mean±SEM of three independent experiments. P values are for one-way with Bonferonni's multiple comparison. *P<0.05, P<0.01, **P<0.0001.

FIG. 28

Titration of Rapa in CD34+ cells. CB-derived CD34+ cells were transduced with SINLV-GFP at a MOI of 1 in presence or absence of increasing concentrations of Rapa. The percentage of GFP+ cells was measured by FACS 5 days post-transduction. Data are the mean±SEM of two independent experiments. p values are for one-way ANOVA with Bonferroni's multiple comparison.

FIG. 29

Impact of CsA and Rapa on murine HSPC and CD4+ T cells. Murine Lin⁻ HSPC (A) and activated CD4+ T cells (B) were transduced with SINLV-GFP at an MOI of 1, in presence or absence of 10 μM CsA or 10 μg/ml Rapamycin or their combination. The percentage of GFP+ cells was evaluated by FACS 5 days post-transduction. Data are the mean±SEM of three independent experiments for HSPC and three independent transductions for CD4+ T cells. p values are for One way ANOVA with Bonferroni's multiple comparison.

FIG. 30

Impact of rapamycin and CsA on LDL-R surface expression in HSPC. CB-derived CD34+ cells were exposed to 10 μM CsA or 10 μg/ml rapamycin for 6 h and LDL-R surface expression was measured by FACS. Data are representative of two independent experiments.

FIG. 31

A88T yields more integrated proviral copies that WT LV in presence of CsA. CB-derived CD34+ cells were transduced with SINLV-GFP harboring either the WT or the A88T capsid at a MOI of 1, in presence or absence of 10 μM CsA. VCN/cell were determined by Taqman assay 14 days post-transduction. Data represent the mean±SEM of four independent experiments. p values are for One way ANOVA with Bonferroni's multiple comparison.

FIG. 32

CsA and rapamycin act on distinct steps on the LV life cycle. Cord blood (CB)-derived CD34+ cells were transduced with WT or A88T SINLVGFP at an MOI of 10 (A-C) or an IDLV harboring WT CA at an MOI of 50 (D), in presence or absence of 10 μmol/l CsA or 10 μg/ml rapamycin. The LV genome fate was tracked by measuring late-RT product (A) and 2LTR circles (B) 24 hours after transduction and integrated proviral copies 2 weeks after transduction (C). Data represent the mean±SEM of four independent experiments expressed as fold versus DMSO WT (A,B) or as absolute copies/cell (C). D. IDLV transduction efficiency was measured 3 days after transduction by FACS (left panel) and by measuring the retrotranscribed LV DNA products by PCR (right panel). Data are the mean±SEM of three independent experiments. P values are for one-way with Bonferonni's multiple comparison. *P<0.05, P<0.01, **P<0.0001.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F., and Maniatis, T. (1989) *Molecular Cloning: A Laboratory Manual,* 2nd Edition, Cold Spring Harbor Laboratory Press; Ausubel, F. M. et al. (1995 and periodic supplements) *Current Protocols in Molecular Biology,* Ch. 9, 13 and 16, John Wiley & Sons; Roe, B., Crabtree, J., and Kahn, A. (1996) *DNA Isolation and Sequencing: Essential Techniques,* John Wiley & Sons; Polak, J. M., and McGee, J. O'D. (1990) *In Situ Hybridization: Principles and Practice,* Oxford University Press; Gait, M. J. (1984) *Oligonucleotide Synthesis: A Practical Approach,* IRL Press; and Lilley, D. M., and Dahlberg, J. E. (1992) *Methods in Enzymology: DNA Structures Part A: Synthesis and Physical Analysis of DNA,* Academic Press. Each of these general texts is herein incorporated by reference.

In one aspect, the present invention provides the use of cyclosporin A (CsA) or a derivative thereof for increasing the efficiency of transduction of an isolated population of human haematopoietic stem and/or progenitor cells by a vector derived from HIV-1, HIV-2, FIV, BIV, EIAV, CAEV or visna lentivirus.

Increasing the efficiency of transduction refers to an increase in the transduction of haematopoietic stem and/or progenitor cells in the presence of an agent (e.g. CsA or a derivative thereof), in comparison to the transduction achieved in the absence of the agent but under otherwise substantially identical conditions. An increased efficiency of transduction may therefore allow the multiplicity of infection (MOI) and/or the transduction time required to achieve effective transduction to be reduced.

In one embodiment, the percentage of haematopoietic stem and/or progenitor cells transduced by the vector is increased. In another embodiment, the vector copy number per cell is increased. Preferably both are achieved at the same time.

Methods for determining the percentage of cells transduced by a vector are known in the art. Suitable methods include flow cytometry, fluorescence-activated cell sorting (FACS) and fluorescence microscopy. The technique employed is preferably one which is amenable to automation and/or high throughput screening.

For example, a population of cells may be transduced with a vector which harbours a reporter gene. The vector may be constructed such that the reporter gene is expressed when the vector transduces a cell. Suitable reporter genes include genes encoding fluorescent proteins, for example green, yellow, cherry, cyan or orange fluorescent proteins. Once the population of cells has been transduced by the vector, both the number of cells expressing and not-expressing the reporter gene may be quantified using a suitable technique, such as FACS. The percentage of cells transduced by the vector may then be calculated.

Alternatively, quantitative PCR (qPCR) may be used to determine the percentage of cells transduced by a vector that does not harbour a reporter gene. For example, single colonies of $CD34^+$ cells may be picked from a semi-solid culture and qPCR may be performed on each colony separately to determine the percentage of vector-positive colonies among those analysed.

Methods for determining vector copy number are also known in the art. The technique employed is preferably one which is amenable to automation and/or high throughput screening. Suitable techniques include quantitative PCR (qPCR) and Southern blot-based approaches.

Cyclosporin A

Cyclosporin A (CsA, CAS No. 59865-13-3) is a poly-N-methylated cyclic undecapeptide having the following structure:

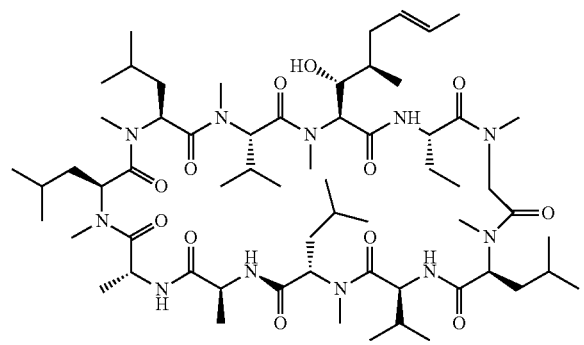

CsA is an approved immunosuppressive agent for use in prevention of allograft rejection. CsA mediates immunosuppression as a complex with the host peptidyl-prolyl isomerase cyclophilin A (CypA). This inhibits the $Ca^{2+}$-dependent phosphatase calcineurin and consequent activation of pro-inflammatory cytokines such as IL-2 (Sokolskaja, E. et al. (2006) Curr. Opin. Microbiol. 9: 404-8). At higher concentrations CsA also exerts anti-tumour activity toward several types of tumour cells, including malignant gliomas resistant to many traditional chemotherapeutics.

Solutions of CsA for use in the present invention may be prepared using routine methods known in the art. In addition, suitable clinical-grade solutions of CsA are known in the art (e.g. Sandimmune).

The concentration at which CsA or a derivative thereof is applied to a population of haematopoietic stem and/or progenitor cells may be adjusted for different vector systems to optimise transduction efficiency. Methods for determining transduction efficiency have been described above.

CsA may be toxic to haematopoietic stem and/or progenitor cells if it is applied at too high a concentration. The toxicity of CsA or a derivative thereof on haematopoietic stem and/or progenitor cells may be determined by quantifying the number of viable cells remaining after exposure to CsA for a certain time. Methods for quantifying the number of viable cells are known in the art.

A skilled person may therefore select a suitable concentration of CsA or a derivative thereof to maximise increase in transduction efficiency while minimising the effect of toxicity using the approaches described herein.

The present invention encompasses the use of CsA and derivatives of CsA. The CsA derivatives of the present invention are those which increase the efficiency of transduction of an isolated population of haematopoietic stem and/or progenitor cells by a vector derived from HIV-1, HIV-2, FIV, BIV, EIAV, CAEV or visna lentivirus.

CsA derivatives of the present invention may have been developed for increased solubility, increased stability and/or reduced toxicity. A number of derivatives of CsA are known in the art.

CsA derivatives of the invention are preferably of low toxicity for mammals, in particular humans. Preferably, CsA derivatives of the invention are of low toxicity for haematopoietic stem and/or progenitor cells.

Suitable CsA derivatives may be identified using methods known in the art for determining transduction efficiency. For example, methods for determining the percentage of haematopoietic stem and/or progenitor cells that are transduced by a vector, or methods for determining the vector copy number per cell may be employed. Such methods have been described above. The method employed is preferably one which is amenable to automation and/or high throughput screening of candidate CsA derivatives. The candidate CsA derivatives may form part of a library of CsA derivatives.

Rapamycin

Rapamycin (CAS No. 53123-88-9, also known as Sirolimus) is a macrolide produced by Streptomyces hygroscopicus. Rapamycin has the following structure:

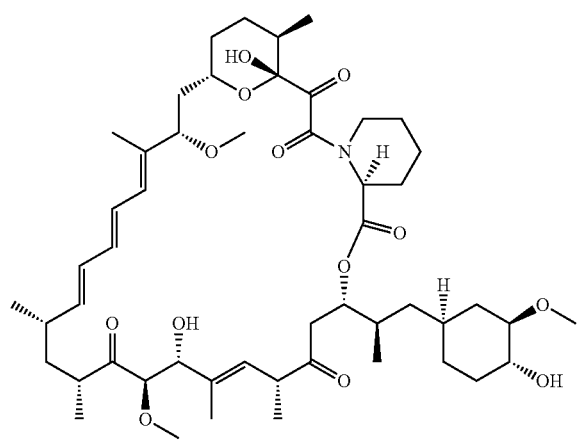

Rapamycin is also an approved immunosuppressive agent for use in prevention of allograft rejection. Similarly to CsA, rapamycin exerts its immunosuppressive effect through binding and inhibition of a host peptidyl-prolyl isomerase, although in this case FKBP12 (Harding, M. W. et al. (1989) Nature 341: 758-60; Siekierka, J. J. et al. (1989) Nature 341: 755-7).

3-methyladenine 3-methyladenine (3-MA, CAS No. 5142-23-4) has the following structure:

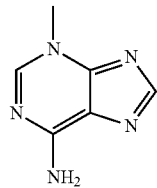

3-MA is a widely used inhibitor of autophagy (Kondo, Y. et al (2005) *Nat. Rev. Cancer* 5: 726-34).

Haematopoietic Stem and Progenitor Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

The haematopoietic stem and progenitor cells of the invention comprise the CD34 cell surface marker (denoted as CD34$^+$).

HSPC Source

A population of haematopoietic stem and/or progenitor cells may be obtained from a tissue sample.

For example, a population of haematopoietic stem and/or progenitor cells may be obtained from peripheral blood (e.g. adult and foetal peripheral blood), umbilical cord blood, bone marrow, liver or spleen. Preferably, these cells are obtained from peripheral blood or bone marrow. They may be obtained after mobilisation of the cells in vivo by means of growth factor treatment.

Mobilisation may be carried out using, for example, G-CSF, plerixaphor or combinations thereof. Other agents, such as NSAIDs and dipeptidyl peptidase inhibitors, may also be useful as mobilising agents.

With the availability of the stem cell growth factors GM-CSF and G-CSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, HSPCs may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By "negative marker" it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By "positive marker" it is to be understood that human HSCs express these markers.

Differentiated Cells

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T-cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T) and CD56 (NK).

Isolation and Enrichment of Populations of Cells

By "isolated population" of cells it is to be understood that the population of cells has been previously removed from the body. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD34) may be purified from a starting population of cells. Alternatively, or in addition, a population of cells that does not express another marker (such as CD38) may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD34 or CD38) may be achieved by using an agent that binds to that marker, preferably substantially specifically to that marker.

An agent that binds to a cellular marker may be an antibody, for example an anti-CD34 or anti-CD38 antibody. The term "antibody" refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead, or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for HSCs.

Vectors

A vector is a tool that allows or facilitates the transfer of an entity from one environment to another. The vectors used to transduce haematopoietic stem and/or progenitor cells in the present invention are viral vectors. The viral vectors are derived from HIV-1, HIV-2, FIV, BIV, EIAV, CAEV or visna lentivirus. These viruses are all lentiviruses.

By "vector derived from" a certain type of virus, it is to be understood that the vector comprises at least one component part derivable from that type of virus.

Vectors derived from SIV are not included in the present invention. The present invention does not encompass vectors comprising SIV-derived capsid proteins.

Retroviral and Lentiviral Vectors

A retroviral vector may be derived from or may be derivable from any suitable retrovirus. A large number of different retroviruses have been identified. Examples include murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) *Retroviruses*, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) *Retroviruses*, Cold Spring Harbour Laboratory Press, 758-63.

The basic structure of retrovirus and lentivirus genomes share many common features such as a 5' LTR and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) *Retroviruses*, Cold Spring Harbour Laboratory Press, 758-63. In brief, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (SIV). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) *EMBO J.* 11: 3053-8; Lewis, P. F. et al. (1994) *J. Virol.* 68: 510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans).

Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) *Science* 272: 263-7; Naldini, L. et al. (1996) *Proc. Natl. Acad. Sci. USA* 93: 11382-8; Leavitt, A. D. et al. (1996) *J.*

*Virol.* 70: 721-8) or by modifying or deleting essential att sequences from the vector LTR (Nightingale, S. J. et al. (2006) *Mol. Ther.* 13: 1121-32), or by a combination of the above.

HIV-Derived Vectors

HIV-derived vectors for use in the present invention are not particularly limited in terms of HIV strain. Numerous examples of sequences of HIV strains may be found at the HIV Sequence Database (http://www.hiv.lanl.gov/content/index).

In a preferred embodiment, the vector derived from HIV-1 excludes a vector which comprises a capsid protein or a gene encoding for a capsid protein which comprises proline at position 86, glutamine at position 87, valine at position 91 and isoleucine at position 96.

In addition, vectors derived from SIV (i.e. including SIV component parts) are not included in the present invention.

Figure 1:
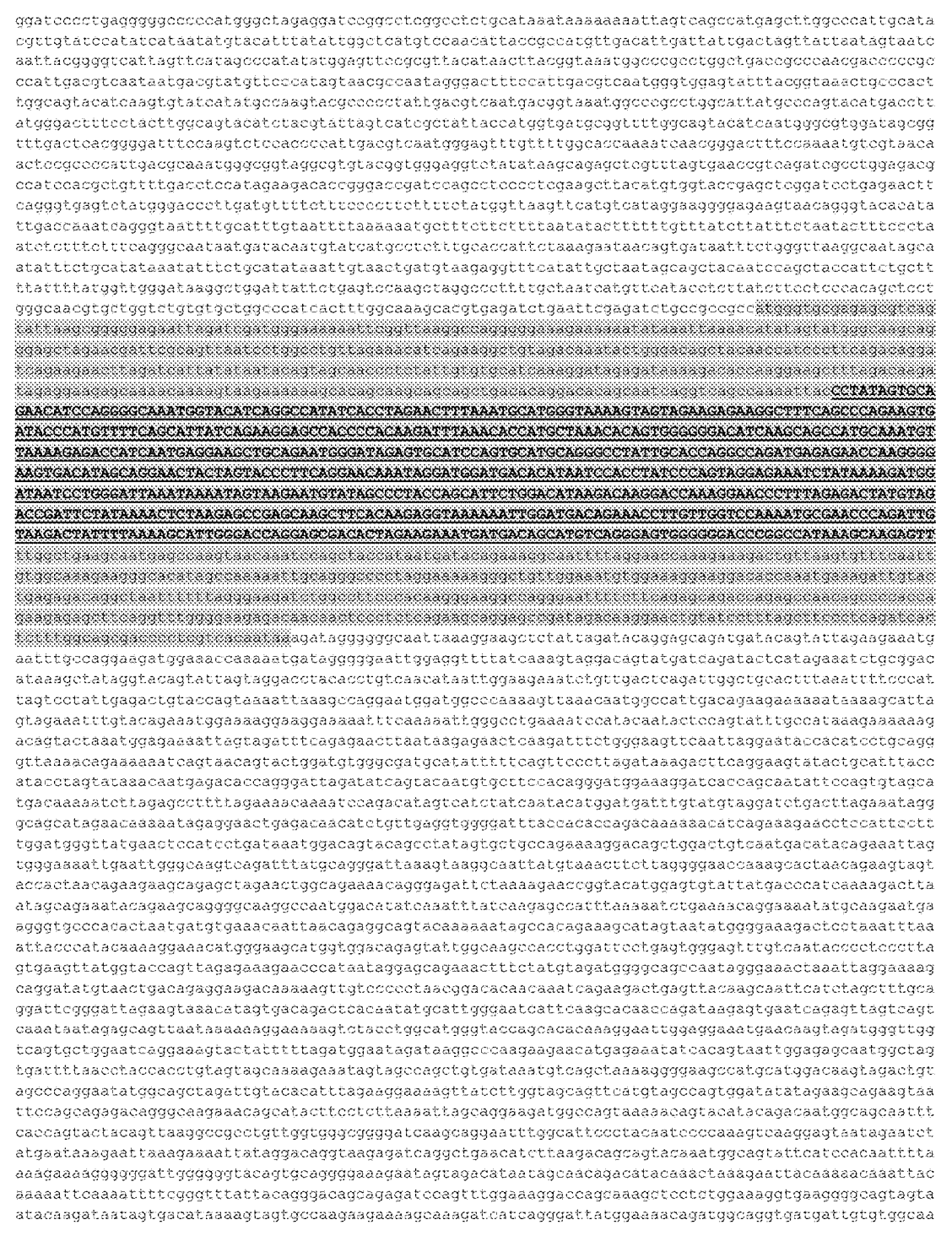

For example, a HIV-1-derived vector may be derived from any of the HIV-1 strains NL4-3, IIIB_LAI or HXB2_LAI (X4-tropic), or BAL (R5-tropic), or a chimaera thereof. Preferably, HIV-1-derived vectors are derived from the pMDLg/pRRE Gag-Pol-expressing packaging construct (FIGS. 1-4; U.S. Pat. Nos. 7,629,153; 8,652,837; Naldini, L. et al. (1996) *Science* 272: 263-7; Follenzi, A. et al. (2002) *Methods Enzymol.* 346: 454-65).

A HIV-2-derived vector may be derived, for example, from the HIV-2 strain ROD.

Capsid Proteins

In a lentiviral particle, the genetic material is contained within a capsid shell and the capsid is in turn contained within a viral envelope. The capsid itself is comprised of a lattice of individual capsid proteins.

The capsid (CA or p24) protein is encoded by the viral gag gene and is comprised within the Gag polyprotein. Mature capsid is generated by processing of the precursor Gag.

Herein, amino acid residues within capsid are numbered following a convention whereby the N-terminal proline of the mature capsid derived from the pMDLg/pRRE system is assigned to be residue 1. The amino acid sequence of the mature capsid derived from the pMDLg/pRRE is:

(SEQ ID NO: 1)
PIVQNIQGQMVHQAISPRTLNAWVKVVEEKAFSPEVIPMFSALSEGATP

QDLNTMLNTVGGHQAAMQMLKETINEEAAEWDRVHPVHAGPIAPGQMRE

PRGSDIAGTTSTLQEQIGWMTHNPPIPVGEIYKRWIILGLNKIVRMYSP

TSILDIRQGPKEPFRDYVDRFYKTLRAEQASQEVKNWMTETLLVQNANP

DCKTILKALGPGATLEEMMTACQGVGGPGHKARV

Identities of individual residues and positions of mutations are described herein with reference to this numbering convention. A skilled person would readily be able to determine analogous positions in homologous proteins by performing a sequence alignment to this capsid protein. For example, sequence alignments comparing capsid proteins of a number of HIV-1-derived vectors are shown in FIG. 5.

Incorporating glutamic acid at position 92 and/or threonine at position 88 of the capsid protein gives rise to improved transduction efficiency in the presence of CsA.

Accordingly, in one embodiment of the present invention, the vector comprises a capsid comprising glutamic acid at position 92.

In another particularly preferred embodiment, the vector comprises a capsid comprising threonine at position 88.

The vector of the invention may comprise both glutamic acid at position 92 and threonine at position 88.

In addition, another aspect of the present invention provides the use of an HIV-1, HIV-2, FIV, BIV, EIAV, CAEV or visna lentivirus-derived capsid mutant for increasing the efficiency of transduction of an isolated population of haematopoietic stem and/or progenitor cells by a vector derived from HIV-1, HIV-2, FIV, BIV, EIAV, CAEV or visna lentivirus in comparison to a vector lacking said mutation, wherein the capsid mutant comprises glutamic acid at position 92 and/or threonine at position 88.

Positions 92 and 88 are indicated in FIG. 6 on the capsid protein from pMDLg/pRRE as an example. In this example, an A88T mutation may be generated by altering the codon corresponding to amino acid position 88 from G$\underline{C}$A to $\underline{A}$CA. Alternatively or in addition, in this example an A92E mutation may be generated by altering the codon corresponding to amino acid position 92 from GC$\underline{A}$ to GA$\underline{A}$.

Figure 8:
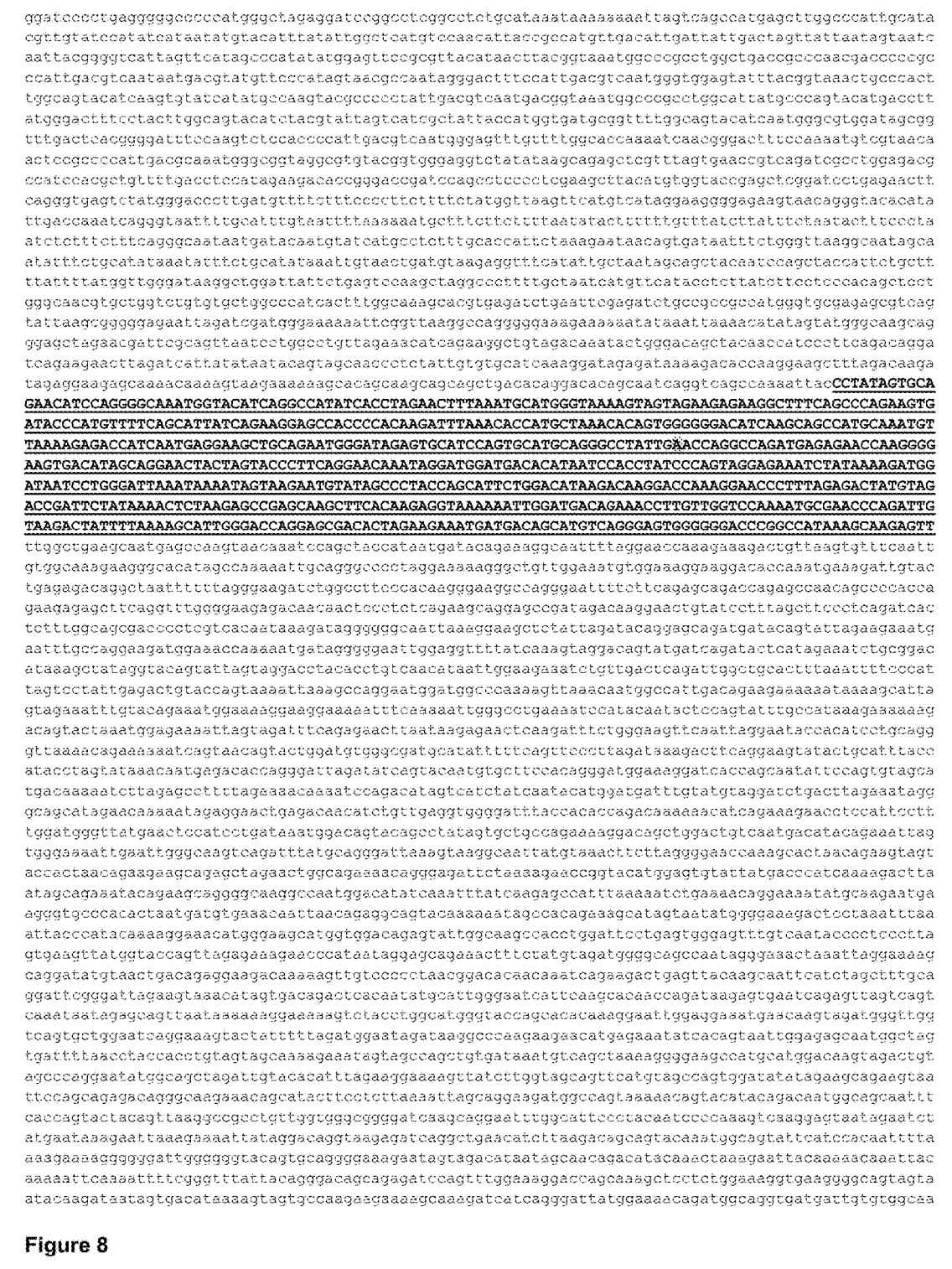
Figure 9:
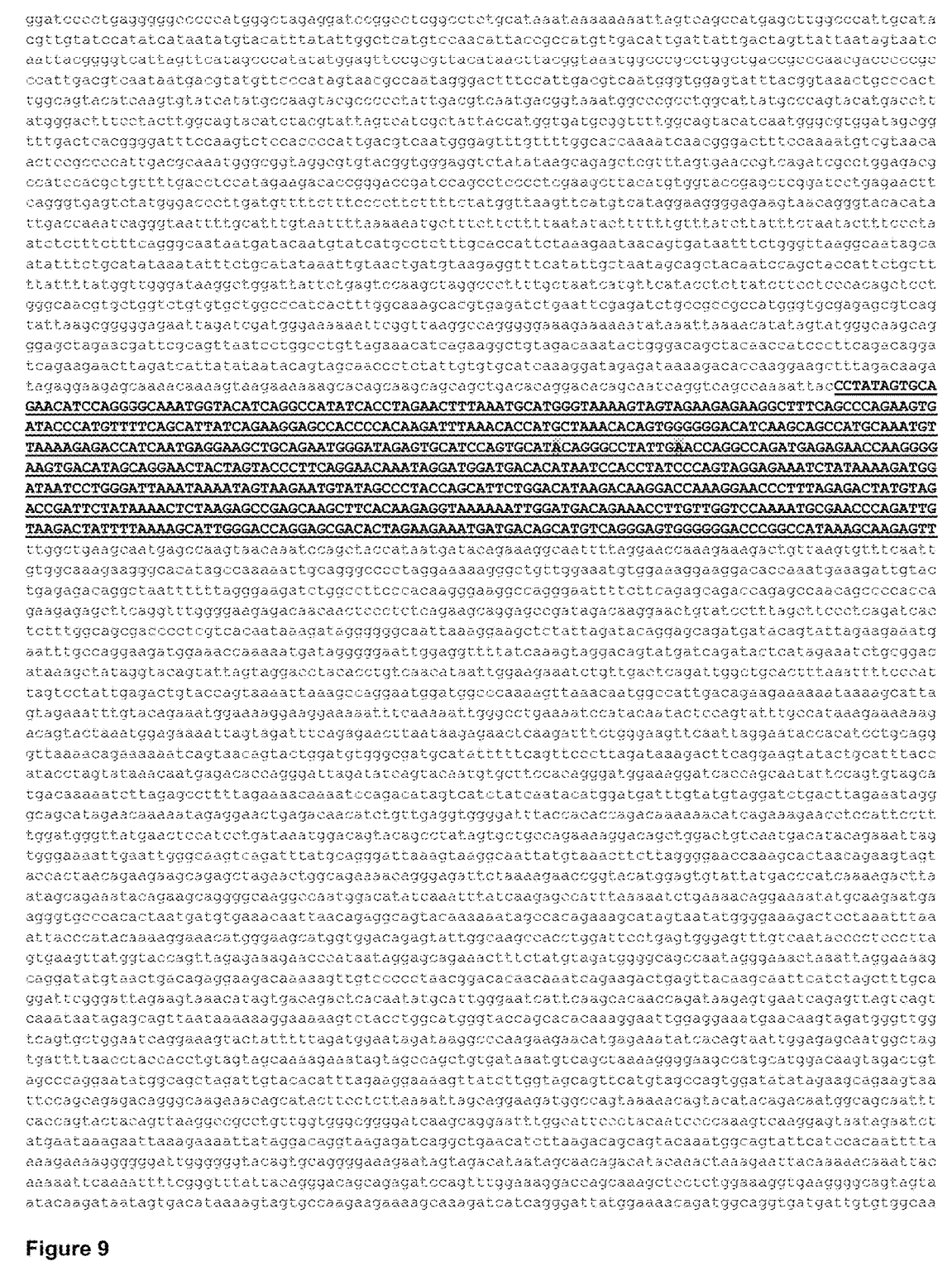

For example, FIGS. 7-9 show the pMDLg/pRRE Gag-Pol-expressing packaging construct incorporating the A88T, A92E mutations, and the A88T/A92E double mutation, respectively.

It should be understood, however, that the skilled person would readily be able to generate alternative polynucleotide sequences that give rise to the same amino acid sequences due to the degeneracy of the genetic code.

Nucleotide of Interest

The vector used in the present invention preferably comprises a nucleotide of interest.

Preferably the nucleotide of interest gives rise to a therapeutic effect.

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

An example of a NOI is the beta-globin chain which may be used for gene therapy of thalassemia/sickle cell disease.

NOIs also include those useful for the treatment of other diseases requiring non-urgent/elective gene correction in the myeloid lineage such as: chronic granulomatous disease (CGD, e.g. the gp91phox transgene), leukocyte adhesion defects, other phagocyte disorders in patients without ongoing severe infections and inherited bone marrow failure syndromes (e.g. Fanconi anaemia), as well as primary immunodeficiencies (SCIDs).

NOIs also include those useful in the treatment of lysosomal storage disorders and immunodeficiencies.

Pharmaceutical Composition

The cells of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy product is preferably performed in compliance with FACT-JACIE International Standards for cellular therapy.

Haematopoietic Stem and/or Progenitor Cell Transplantation

The present invention provides a population of haematopoietic stem and/or progenitor cells prepared according to a method of the invention for use in therapy, for example for use in gene therapy.

The use may be as part of a haematopoietic stem and/or progenitor cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment, a population of haematopoietic stem and/or progenitor cells prepared according to a method of the invention is administered as part of an autologous stem cell transplant procedure.

In another embodiment, a population of haematopoietic stem and/or progenitor cells prepared according to a method of the invention is administered as part of an allogeneic stem cell transplant procedure.

By "autologous stem cell transplant procedure" it is to be understood that the starting population of cells (which are then transduced according to a method of the invention) is obtained from the same subject as that to which the transduced cell population is administered. Autologous transplant procedures are advantageous as they avoid problems associated with immunological incompatibility and are available to subjects irrespective of the availability of a genetically matched donor.

By "allogeneic stem cell transplant procedure" it is to be understood that the starting population of cells (which are then transduced according to a method of the invention) is obtained from a different subject as that to which the transduced cell population is administered. Preferably, the donor will be genetically matched to the subject to which the cells are administered to minimise the risk of immunological incompatibility.

Suitable doses of transduced cell populations are such as to be therapeutically and/or prophylactically effective. The dose to be administered may depend on the subject and condition to be treated, and may be readily determined by a skilled person.

Haematopoietic progenitor cells provide short term engraftment. Accordingly, gene therapy by administering transduced haematopoietic progenitor cells would provide a non-permanent effect in the subject. For example, the effect may be limited to 1-6 months following administration of the transduced haematopoietic progenitor cells. An advantage of this approach would be better safety and tolerability, due to the self-limited nature of the therapeutic intervention.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

The methods, cell populations and/or CsA of the present invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the methods, cell populations and/or CsA of the present invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the methods, cell populations and/or CsA of the present invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Hunting-ton's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

In addition, or in the alternative, the methods, cell populations and/or CsA of the present invention may be useful in the treatment of β-thalassemia, chronic granulomatous disease, metachromatic leukodystrophy, mucopolysaccharidoses disorders and other lysosomal storage disorders.

Kit

In another aspect, the present invention provides a kit comprising CsA and/or cell populations of the invention.

The CsA and/or cell populations may be provided in suitable containers. The kit may also include instructions for use.

Method of Treatment

It is to be appreciated that all references herein to treatment include curative, palliative and prophylactic treatment; although in the context of the present invention references to preventing are more commonly associated with prophylactic treatment. The treatment of mammals, particularly humans, is preferred. Both human and veterinary treatments are within the scope of the present invention.

EXAMPLES

Example 1

Materials and Methods
Vectors
Third generation lentivirus (LV) stocks were prepared, concentrated and titred as previously described (Dull, T. et al. (1998) *J. Virol.* 72: 8463-71; Follenzi, A. et al. (2000) *Nat. Genetics* 25: 217-22). Briefly, self-inactivating (SIN) LV vectors were produced using the transfer vector pCCLsin.cPPT.hPGK.eGFP.Wpre, the packaging plasmid pMDLg/pRRE, Rev-expressing pCMV-Rev and the VSV-g envelope-encoding pMD2.VSV-G plasmids. Bald vector, a normal LV produced by omitting the Env-encoding plasmid during vector production, was produced as a negative control. During vector production, the Env construct was substituted by pcDNA3.1 (Invitrogen Inc.). For SINLV capsid mutants, vectors were produced as described above, except that the wild-type pMDLg/pRRE was replaced with a packaging plasmid harbouring a specific point-mutation in the p24 coding region as follows: pMDLg/pRRE-N74D; pMDLg/pRRE-P90A; pMDLg/pRRE-A105T; pMDLg/pRRE-V86M; pMDLg/pRRE-A92E; pMDLg/pRRE-A88T. All modified packaging plasmids were purchased from GenScript Inc. The SIN-retroviral vector (SIN-RV) was produced as previously described (Montini, E. et al. (2006) *Nat. Biotechnol.* 24: 687-96) using as transfer vector RVrkat43.2MLV_GFP, the packaging plasmid pCM-gag-pol and the VSV-g envelope-encoding pMD2.VSV-G plasmid.

Cells
Cell Lines
The human embryonic kidney 293T cells (HEK293T) as well as the human K562 myelogenous leukaemia cell lines were maintained in Iscove's modified Dulbecco's medium (IMDM; Sigma) supplemented with 10% foetal bovine serum (FBS; Gibco), penicillin (100 IU/mL), streptomycin (100 μg/mL) and 2% glutamine.

Primary Cells
Human CD34$^+$ HSPC, CD4$^+$ T cells and CD14$^+$ monocytes were isolated through positive magnetic bead selection according to the manufacturer's instructions (Miltenyi) from umbilical cord blood collected upon informed consent from healthy volunteers according to the Institutional Ethical Committee approved protocol (TIGET01). Otherwise, cord blood (CB) and bone marrow (BM)-derived CD34$^+$ cells were purchased from Lonza.

CD4$^+$ T cells were activated in RPMI, supplemented with 10% FBS, penicillin (100 IU/mL), streptomycin (100 μg/mL), 2% glutamine, phytohaemagglutanin (PHA) (2

µg/mL, Roche) and IL-2 (300 IU/mL, Novartis) for three days and maintained in RPMI supplemented with 10% FBS, penicillin (100 IU/mL), streptomycin (100 µg/mL), 2% glutamine and IL-2 (300 UI/mL). Monocyte-derived macrophages (MDM) were differentiated from isolated CD14+ monocytes in DMEM supplemented with 10% FBS, penicillin (100 IU/mL), streptomycin (100 µg/mL), 2% glutamine and 5% human serum AB (Lonza) for seven days.

All cells were maintained in a 5% $CO_2$ humidified atmosphere at 37° C.

Transduction

Human CB and BM-derived haematopoietic stem/progenitor cells (HSPC) were cultured in serum-free StemSpan medium (StemCell Technologies) supplemented with 100 ng/mL recombinant human stem cell factor (rhSCF), 20 ng/mL recombinant human thrombopoietin (rhTPO), 100 ng/mL recombinant human Flt3 ligand (rhFlt3) and 20 ng/mL recombinant human IL6 (rhIL6) (all from Peprotech) 16 to 24 hours prior to transduction. HSPC were then transduced at a concentration of $1\times10^6$ cells per mL with vesicular stomatitis virus glycoprotein (VSV-G)-pseudotyped SINLV for 20 hours at the indicated multiplicity of infection (MOI) in the same medium. After transduction, cells were washed and maintained serum-free StemSpan supplemented with cytokines as above until the reading of GFP-positive (GFP+) cells by FACS. After FACS they were maintained in Roswell Park Memorial Institute medium (RPMI, Lonza) supplemented with 10% FBS, 25 ng/mL rhSCF, 5 ng/mL rhIL6, 25 ng/mL rhFlt3 and 5 ng/mL rhTPO for another seven days before analysis of vector copy numbers. MDM were transduced 7 days after differentiation. T lymphocytes were transduced at a concentration of $10^6$ cells per mL, after 3 days of stimulation. All the cells were exposed to the vector for 16-20 hours.

Compounds

Cyclosporin A, FK506, rapamycin and 3-MA (all from Sigma-Aldrich) were resuspended and stored according to the manufacturer's instructions. They were added to the transduction medium at the indicated concentration and washed out with the vector 16-20 hours later.

Transplantation of Human HSPC in NSG Mice

NOD-SCID-IL2Rg−/− (NSG) mice were purchased from Jackson laboratory. All animal procedures were performed according to protocols approved by the Animal Care and Use Committee of the Ospedale San Raffaele (IACUC 661) and communicated to the Ministry of Health and local authorities according to Italian law. Human cord blood-derived CD34+ cells (purchased from Lonza, 2C-101) were pre-stimulated and transduced as described previously with SINLV-GFP at a MOI of 10 in presence of DMSO/CsA/Rapa or their combination as indicated. After transduction, $1.3\times10^5$ cells were infused into the tail vein of sublethally irradiated 10-week-old NSG mice (radiation dose: 200 cGy for mice weighing 18-25 g and 220 cGy for mice above 25 g of weight). Transduced and untransduced cells were also cultured in vitro for 14 days for further analysis. In vitro cultured cells and BM cells isolated from transplanted mice at the time of sacrifice were then used to quantify the VCN by qPCR.

Colony-Forming Cell Assay

Colony-forming cell assays were performed by plating $8\times10^2$ human cord blood-derived CD34+ cells transduced with SINLV-GFP at a MOI of 10 in presence of the different compounds in a methylcellulose-based medium (Methocult GF4434, Stem Cell Technologies). 15 days later, colonies were scored by light microscopy for colony numbers and morphology. CFU-E and BFU-E were scored as erythroid colonies, while CFU-G, CFU-M, CFU-GM and CFU-GEMM as myeloid colonies.

Flow Cytometry

All cytometric analyses were performed using a FACSCanto III instrument and LSRFortessa instruments (BD Biosciences), and analysed with FACS Express software (De Novo Software).

Transduced Cells

GFP expression in transduced cells was measured 5-7 days post-transduction. Adherent MDM were detached by scraping in 5 mM PBS-EDTA, washed and resuspended in PBS containing 2% FBS. Cells grown in suspension were washed and resuspended in PBS containing 2% FBS. To exclude dead cells from the analysis, 10 ng/mL 7-aminoactinomycin D (7-AAD) was added.

Human Colonies

Human differentiated cells from CFC were harvested from a single plate (pool of colonies) and mixed into a single cell suspension. Cells were then washed and resuspended in PBS containing 2% FBS. For immunostaining, cells were incubated with anti-human receptor blocking antibodies for 15 min at 4° C. and then stained for 20 min at 4° C. with anti-human CD235a and CD33 antibodies (for antibodies, see Table 1). To exclude dead cells from the analysis, cells were washed and resuspended in PBS containing 10 ng/mL 7-aminoactinomycin D (7-AAD).

TABLE 1

| Antibody | Fluorochrome | Dilution | Clone | Company | Code |
|---|---|---|---|---|---|
| hCD235a | APC | 1:25 | GA-R2 | BD Biosciences | 551336 |
| hCD33 | BV421 | 1:25 | WM53 | BD Biosciences | 562854 |
| Anti human FCR Blocking | | 1:50 | | Miltenyi Biotec | 120-000-442 |
| hCD45 | APCh7 | 1:25 | 2D1 | BD Biosciences | 641417 |
| hCD19 | PE | 1:25 | SJ25C1 | BD Biosciences | 345789 |
| hCD33 | PeCy7 | 1:25 | P67.6 | BD Biosciences | 333952 |
| hCD3 | APC | 1:25 | UCHT1 | BD Biosciences | 555335 |
| hCD13 | BV | 1:25 | WM15 | BD Biosciences | 562596 |
| hCD34 | PeCy7 | 1:25 | 8G12 | BD Biosciences | 348811 |
| hCD38 | V450 | 1:25 | HB7 | BD Biosciences | 646851 |
| hCD90 | APC | 1:25 | 5E10 | BD Biosciences | 559869 |
| Hcd133/2 | PE | 1:25 | 293C3 | Miltenyi Biotec | 130-090-853 |

Peripheral Blood From Mice

For each mouse, 250 µL of peripheral blood were added to 15 µL of PBS containing 45 mg/mL EDTA. For immunostaining, a known volume of whole blood (100 µL) was first incubated with anti-human FcγIII/II receptor (Cd16/Cd32) blocking antibodies for 15 min at 4° C. and then incubated in the presence of monoclonal antibodies (for antibodies, see Table 1) for 20 min at 4° C. Erythrocytes were removed by lysis with the TQ-Prep workstation (Beckman-Coulter) in the presence of an equal volume of FBS (100 µL) to protect white blood cells.

Bone Marrow

BM cells were obtained by flushing the femurs in PBS 2% FBS solution. Cells ($1\times10^6$ cells) were washed, resuspended in 100 µL of PBS containing 2% FBS, and incubated with anti-human receptor (Cd16/Cd32) blocking antibodies for 15 min at 4° C. Staining was then performed with monoclonal antibodies (for antibodies, see Table 1) for 20 min at 4° C. Cells were washed and finally resuspended in PBS containing 2% FBS.

Spleen

Spleens were first smashed and the resulting cell suspension was passed through 40 µm nylon filter and washed in cold phosphate buffered saline (PBS) containing 2 mM EDTA and 0.5% bovine serum albumin (BSA). Cells were incubated with anti-human receptor (Cd16/Cd32) blocking antibodies for 15 min at 4° C. and then stained with anti-human monoclonal antibodies (for antibodies, see Table 1) for 20 min at 4° C. Cells were finally washed and resuspended in PBS containing 2% FBS.

RNA Extraction, qPCR and Gene Expression Analysis

RNA extraction from cells was performed using the RNeasy Plus Mini Kit (Qiagen). Briefly, cells were lysed in Buffer RLT plus, supplemented with β-mercaptoethanol. RNA was then extracted according to manufacturer's instructions. The extracted mRNAs were retrotranscribed using the SuperScript Vilo kit (11754250, Invitrogen). qPCR analyses were done using TaqMan probes from Applied Biosystems (see below). qPCR was run for 40 cycles using the Viia 7 instrument while the Viia 7 software was then used to extract the raw data (Ct). To determine gene expression, the difference (ΔCt) between the threshold cycle (Ct) of each gene and that of the reference gene was calculated by applying an equal threshold. Relative quantification values were calculated as the fold-change expression of the gene of interest over its expression in the reference sample, by the formula 2-ΔΔCt. The expression of the human CypA gene was assessed in K562 cell line, CD4+ primary T cells, MDM and CB-derived CD34+ cells. The expression was normalised using the housekeeping gene HPRT1. The following Taqman probes from Applied Biosystems were used: PPIA (Hs99999904_m1) and HPRT1 (Hs01003267_m1).

Replication Intermediates

CB-derived CD34+ cells were transduced at a MOI of 100, in the presence or absence of CsA or rapamycin. To analyse viral replication intermediates, transduced cells were washed and resuspended in Monini lysis buffer (0.1% polyoxyethylene 10 lauryl ether (Sigma), 0.1 mg/mL proteinase K (Promega)) (25 µL per 1×10$^5$ cells), incubated at 65° C. for 2 h and heat inactivated at 94° C. for 15 min (Monini, P. et al. (1999) Blood 93: 4044-58). Lysis of the cells to retrieve late-RT and 2LTR intermediates was performed at 24 hours post-transduction. Late-RT and 2LTR circles were measured by semi-quantitative Taqman assay with primers described below and normalised using the human TERT gene. Results are expressed as fold versus the DMSO control, as described above.

The primers to detect late-RT products are:

```
LATE RT (5NC2rev):
5'-GAGTCCTGCGTCGAGAGAG-3'
(Naldini, L. et al. (1996) Science 272: 263-7)

LATE RT fw DU3 sense:
5'-TCACTCCCAACGAAGACAAGATC-3'
(Matrai, J. et al. (2011) Hepatology 53: 1696-707)
```

The primers to detect 2LTR products are, according to (De laco A, Luban J. Inhibition of HIV-1 infection by TNPO3 depletion is determined by capsid and detectable after viral cDNA enters the nucleus. Retrovirology. 2011; 8: 98; FIG. 32B):

```
2junct:
5'-CAGTGTGGAAAATCTCTAGCAGTAC-3'

J2 rev:
5'-GCCGTGCGCGCTTCAGCAAGC-3'
```

Other primers to detect 2LTR products are (FIG. 27C):

```
2LTR fw:
5'-AACTAGGGAACCCACTGCTTAAG-3'

2LTR rv:
5'-GATCTTGTCTTCGTTGGGAGTGA-3'

2LTR probe:
5'-FAM-ACACTACTTGAAGCACTCAAGGCAAGCTT-TAMRA-3'
```

The primers to detect TELO are:

```
hTelo fw:
5'-GGCACACGTGGCTTTTCG-3'
(Follenzi, A. et al. (2002) Methods Enzymol.
346: 454-65)

hTelo rev:
5'-GGTGAACCTCGTAAGTTTATGCAA-3' hTelo probe:
VIC-5' TCAGGACGTCGAGTGGACACGGTG-3'-TAMRA
```

Genomic DNA Extraction and qPCR

DNA from cell cultures was extracted using a Maxwell 16 instrument (Promega) or Blood & Cell Culture DNA Micro Kit (Qiagen). To amplify the vector sequence, primers and probes complementary to the vector Rev responsive element sequence were used. Vector copy numbers and replication intermediates were normalised to genomic DNA content, which was assessed using the human TERT gene. Quantitative polymerase chain reaction (qPCR) primers and probe sequences and conditions were previously described (Santoni de Sio, F. R. et al (2006) Blood 107: 4257-65).

ELISA

To assess the secretion of human IFNα upon transduction of CB-derived HSPCs in the presence of the different compounds, supernatants from transduced cells were harvested 24 hours post-transduction and the IFNα concentration was assessed using the VeriKine™ Human IFN Alpha ELISA Kit (PBL interferon source, #41100) according to manufacturer's instructions.

Western Blot

Whole cell extracts were prepared from K562, HSPC, CD4+ T cells and MDM as previously described (Kajaste-Rudnitski, A. et al. (2011) J. Virol. 85: 5183-96; Kajaste-Rudnitski, A. et al. (2006) J. Biol. Chem. 281: 4624-37). Samples were subjected to SDS-PAGE, transferred to PVDF membrane by electroblotting, and blotted with a mouse polyclonal antibody (Ab) raised against CypA (Santa-Cruz Biotechnology). An anti-actin Ab (Sigma-Aldrich) was used as a normaliser.

Statistical Analysis

In all studies, values are expressed as mean±standard error of the mean (SEM). Statistical analyses were performed by unpaired Student's t test or ANOVA for multiple comparisons, as indicated. Percentages were converted into Log ODDs for statistical analysis. Differences were considered statistically significant at $p<0.05$.

Results

Cyclosporin A (CsA) increases lentiviral transduction specifically in human haematopoietic stem and progenitor cells.

In order to test how exposure of human CD34+ haematopoietic stem and progenitor cells (HSPCs) to the immunosuppressive drug cyclosporine (CsA) would impact on LV transduction, cytokine-stimulated cord-blood (CB)-derived CD34+ cells were first exposed to a VSV-g pseudotyped HIV-1-derived self-inactivating (SIN) lentiviral vector expressing GFP under the control of the PGK promoter (SINLV-GFP) at increasing multiplicities of infection (MOI), in the presence or absence of increasing concentrations of CsA. Interestingly, although the two lowest concentrations of CsA did not improve LV transduction, both 10 µM and 50 µM CsA lead to a significant increase in the percentage of GFP+ cells measured by FACS 5 days post-exposure (FIG. 10A). The 50 µM concentration of CsA was less well tolerated by the cells, as observed by crude cell counts over time (FIG. 10B). To further investigate the concentration range at which CsA improves transduction, we titred the compound in the 1-10 µM range. Improved transduction was observed at the highest two doses without significant differences in cell growth between them (FIGS. 10C and 10D). The 10 µM concentration was chosen to further study the impact of CsA on LV transduction in HSPCs.

Figure 11:
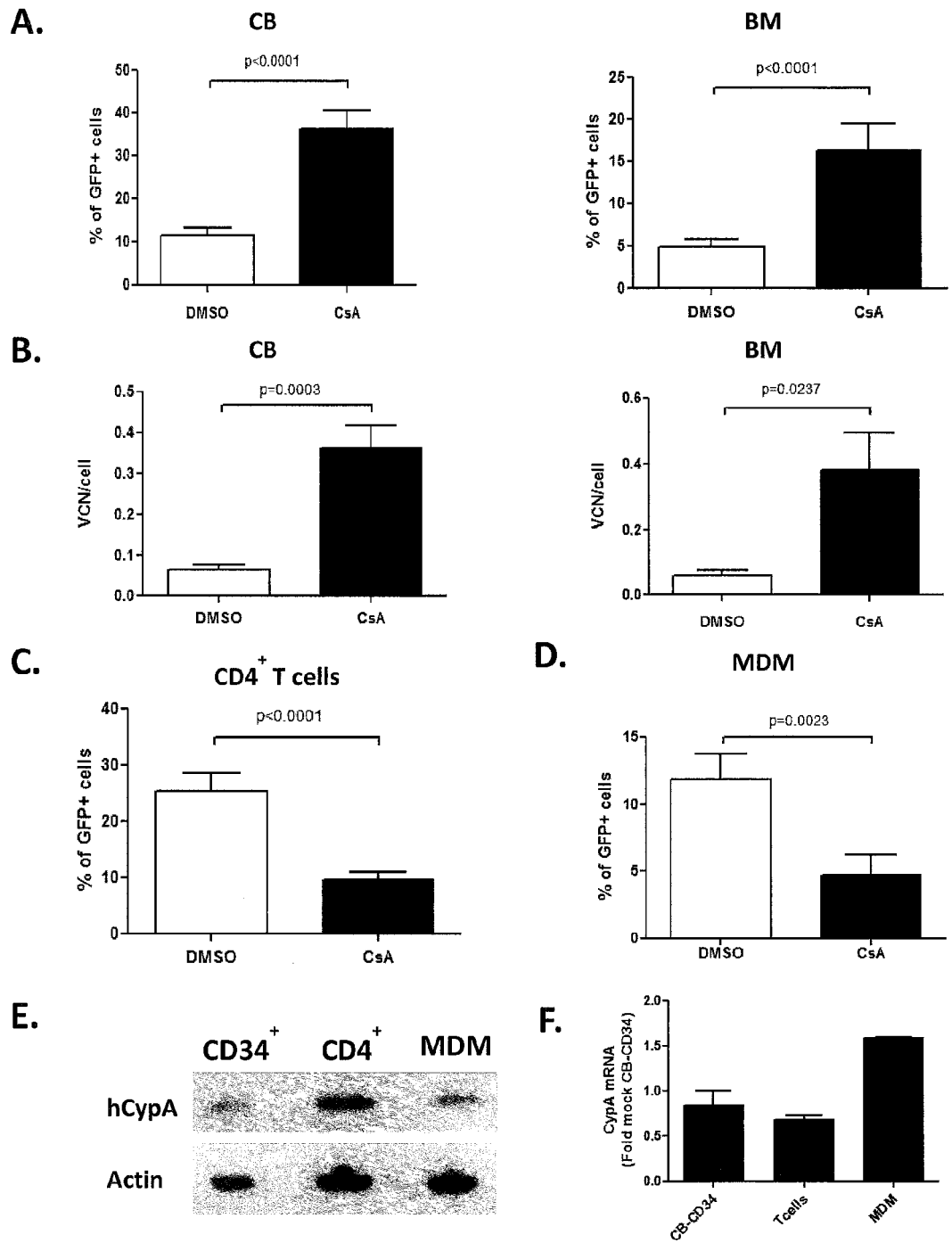

CB and bone marrow (BM)-derived CD34+ cells were stimulated with a growth-promoting cocktail of cytokines for 24 hours prior to transduction. Cells were then exposed to the SINLV-GFP at a MOI of 1, in the presence or absence of 10 µM CsA. Transduction efficiency was measured 5 days post-exposure by FACS, and vector copy numbers (VCN) were assessed at 14 days post-transduction. CsA treatment consistently led to a 3-fold increase in the percentage of GFP+ cells, both in CB and BM-derived HSPC (FIG. 11A, left and right panels respectively). Remarkably, the CsA treatment increased the integrated vector copies by 5.4-fold and 6.2-fold in average in CB and BM-derived HSPC, respectively (FIG. 11B, left and right panels, respectively). This effect was specific to HSPC, as transduction in the presence of CsA lead to a 2.6-fold and 2.5-fold decrease in GFP+ cells in CD4+ T cells and monocyte-derived macrophages (MDM), respectively (FIGS. 11C and 11D).

Figure 12:
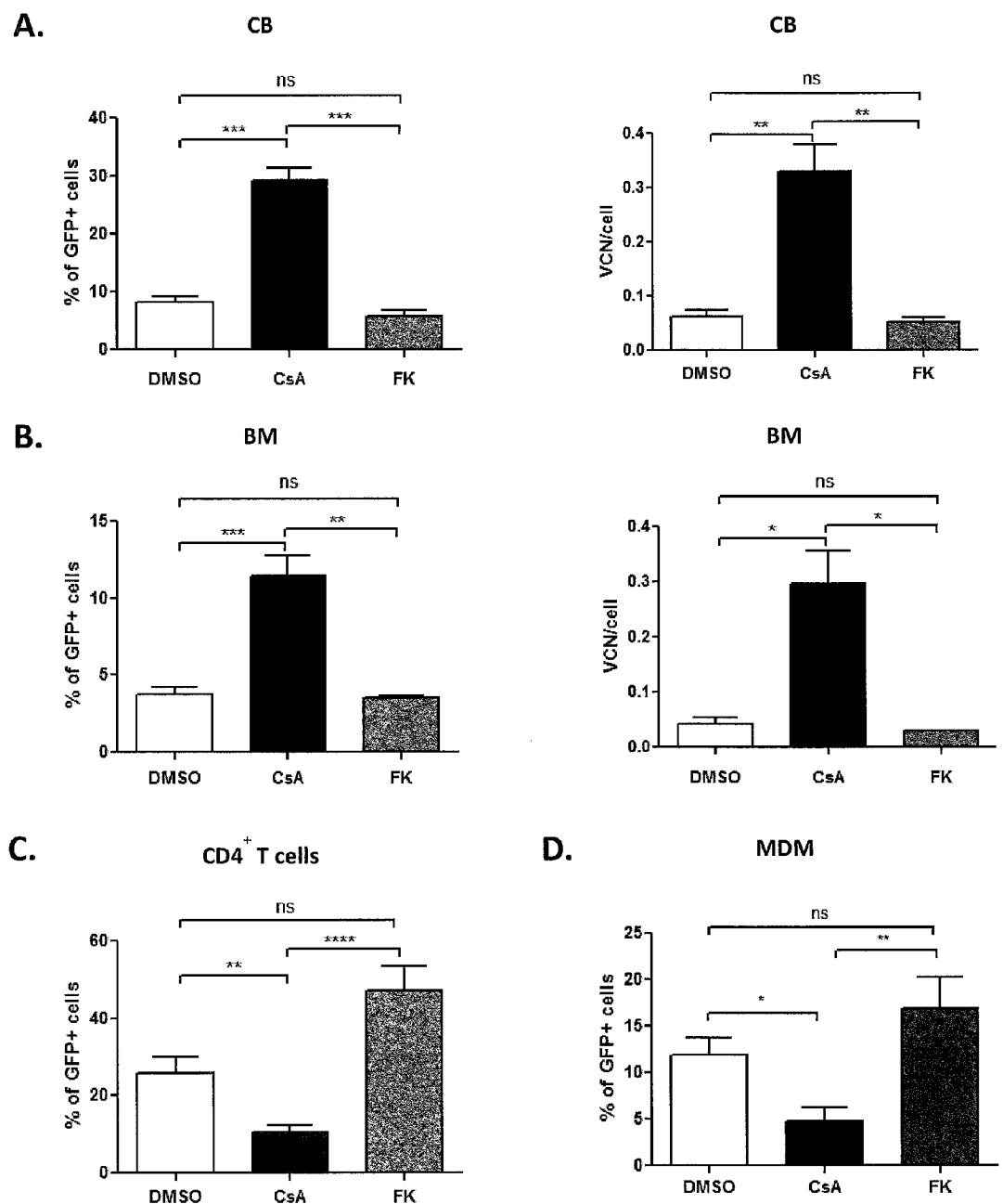

CsA, as a complex with the host immunophilin cyclophilin A (CypA), is a potent inhibitor of the $Ca^{2+}$-dependent phosphatase calcineurin (Colgan, J. et al. (2005) *J. Immunol.* 174: 6030-8). To understand whether the effect of CsA on LV transduction was dependent on the inhibition of calcineurin, we transduced CB and BM-derived CD34+ cells in presence of FK-506, a compound which blocks calcineurin similarly to CsA but independently of CypA (Schreiber, S. L. et al. (1992) *Immunology Today* 13: 136-42). FK-506 had no impact on LV transduction efficiencies in HSPCs, nor in differentiated CD4+ T cells and MDM, ruling out involvement of calcineurin-mediated immunosuppression in the CsA impact on transduction (FIG. 12). To understand whether the discrepancy in the effects of CsA on LV transduction between differentiated haematopoietic cells and the more primitive HSPC could be explained by lack of CypA expression in the latter, CypA mRNA and protein levels were assessed in all three cell types (FIG. 11E). Interestingly, human CD34+ HSPC expressed similar levels of CypA protein as the MDM and CD4+ T cells in which CsA had a negative impact on LV transduction (FIG. 11D). Indeed, the level of CypA expression could not explain the positive effect of CsA in HSPC, as similar expression levels were found also in the human K562 myelogenous leukaemia cell line in which CsA had little or no impact on LV transduction efficiency (FIG. 13). Overall, these results indicate that CsA significantly increases LV transduction efficiency specifically in the CD34+ HSPC compartment, independently of calcineurin-mediated immunosuppression and CypA expression levels.

CsA Improves LV Transduction Alone and in Addition to LV Harbouring Mutant Viral Capsids (CA) in HSPC Besides acting as an immunomodulator, CsA is also known to disrupt the interaction between the host CypA and the HIV-1 capsid (CA or p24), thereby compromising efficient infection (Towers, G. J. et al. (2003) *Nat. Medicine* 9: 1138-43), as observed for CD4+ T cells and MDM (FIGS. 11C and 11D). Several point mutations have been described to alter interactions of the viral CA with cellular partners (Fassati, A. (2012) *Virus Research* 170: 15-24; Gruffer, M. G. et al. (2012) *Curr. Opin. Virol.* 2: 142-50). In order to address whether the LV CA-CypA interaction could be involved in CsA-mediated improvement of transduction in HSPCs, we generated SINLVs harbouring individual CA mutants with the specific features described in Table 2.

TABLE 2

| CA Mutants | Phenotypes | References |
|---|---|---|
| P90A | CypA and Nup153-independent | (Rasaiyaah, J. et al. (2013) *Nature* 503: 402-5) |
| N74D | TNPO3 and Nup153-independent, CPSF6-358 escape mutant, affects CypA interaction | (Zhou, L. et al. (2011) *PLoS Pathog.* 7: e1002194; Price, A. J. et al. (2012) *PLoS Pathog.* 8: e1002896) |
| V86M | Alters CypA-CA interaction relieving hT5α restricted mutants | (Veillette, M. et al. (2013) *Retrovirology* 10: 25) |
| A105T | Relieves CypA-mediated restriction of CsA-dependent CA mutants | (Qi, M. et al. (2008) *J. Virol.* 82: 12001-8) |
| A92E | CypA-independent, CsA-dependent in some cell lines, still interacts with CypA | (De Iaco, A. et al. (2014) *Retrovirology* 11: 11; Song, C. et al. (2007) *J. Virol.* 81: 11946-56; Ylinen, L. M. et al. (2009) *J. Virol.* 83: 2044-7) |
| A88T | M x B escape mutant, no longer binds CypA | (Liu, Z. et al. (2013) *Cell Host Microbe* 14: 398-410) |

Figure 14:
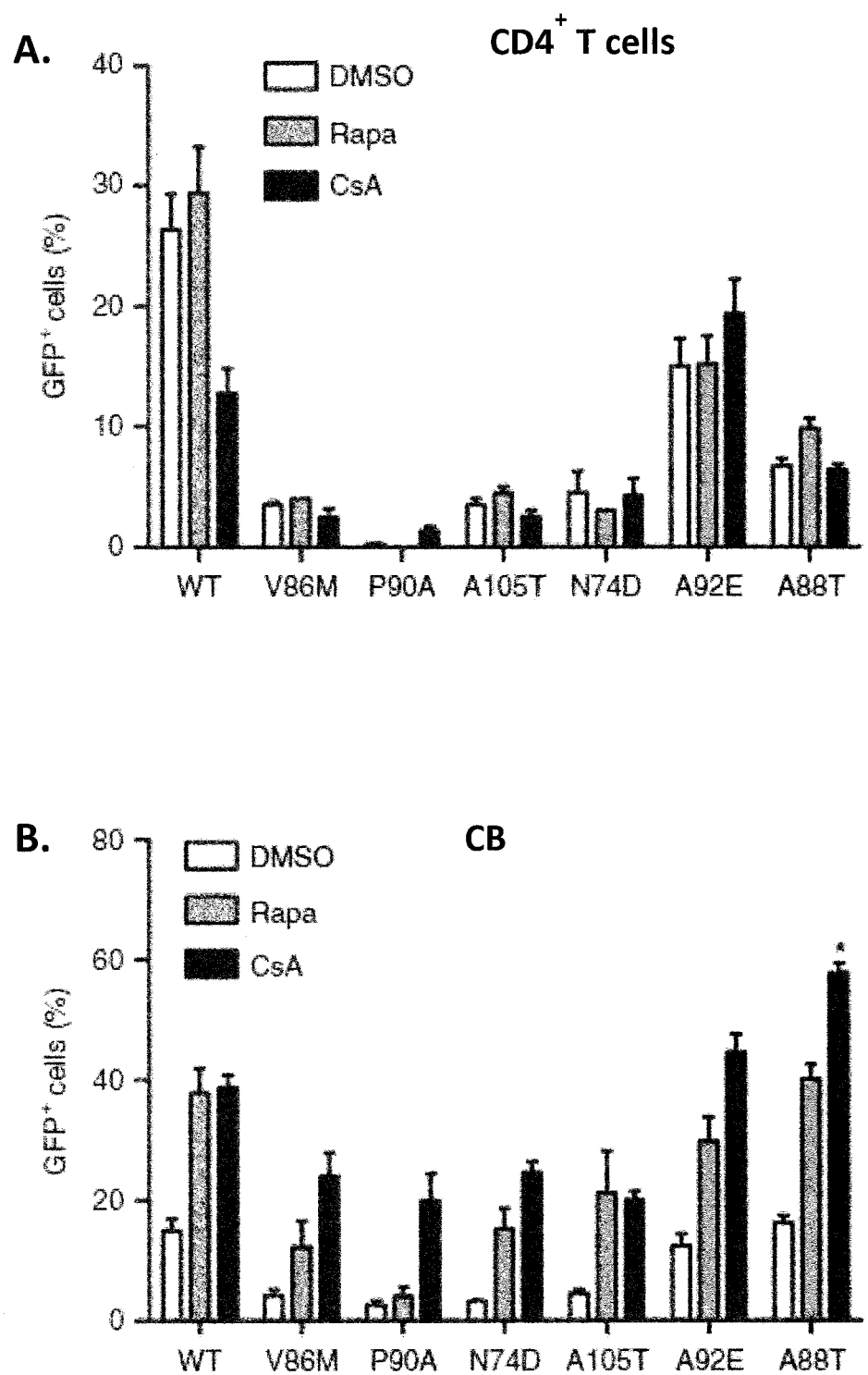
Figure 31:
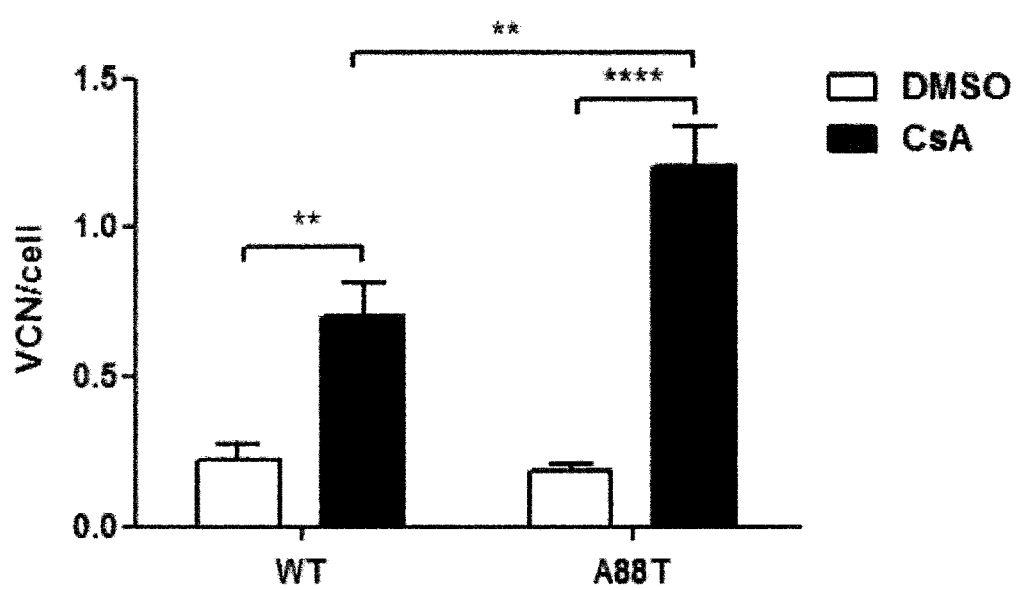

All CA mutants showed impaired transduction efficiencies in CD4+ T cells, in which CypA is an LV promoting factor, despite similar infectivity as the wild-type (WT) vector in 293T cells (FIG. 14A, white bars, mutants versus WT, P<0.0001 for all except A92E which did not reach statistical significance). The impact of Rapa did not vary among the different CA mutants, while CsA inhibited WT LV transduction by around twofold (FIG. 14A, DMSO versus CsA, P<0.01) but did not affect the V86M, A105T, N74D, and A88T mutants. The P90A and A92E mutants tended to benefit from CsA in CD4+ T cells (FIG. 14A). In CD34+ cells, all CA mutants, except A92E and A88T, performed less well than the WT vector in control conditions (FIG. 14B, white bars, mutants versus WT, P<0.0001 for all except A92E and A88T). However, CsA improved transduction efficiency of all vectors (FIG. 14B, DMSO versus CsA, P<0.0001 for all). Interestingly, higher transduction efficiency was observed for A88T as compared to the WT vector in presence of CsA (FIG. 14B, A88T versus WT with CsA, P<0.05). Such additive effects were not observed with rapamycin despite increased efficiency for all CA mutants. Importantly, the A88T CA mutant also yielded a higher VCN/cell as compared to WT vector in the presence of CsA (FIG. 31).

Taken together, our results suggest that CsA-mediates both CA-independent and dependent increase in LV transduction and provides an additive benefit in combination with A92E and A88T mutant CA.

Figure 28:
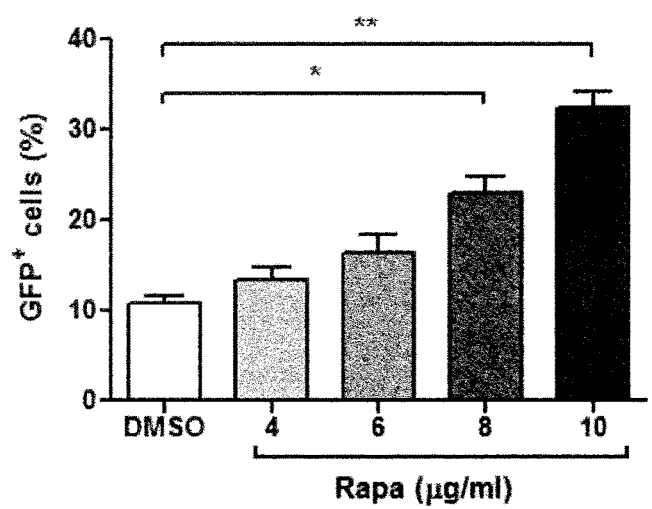

Combination of CsA with Rapamycin Provides a Further Increase in LV Transduction in HSPC We compared the impact of CsA on LV transduction to that of rapamycin alone or in combination with CsA in both CB and BM-derived HSPC. We chose the 10 µg/ml concentration of rapamycin for our experiments as it was associated with improved transduction efficiency over lower doses (FIG. 28). Although rapamycin led to a statistically significant 2-fold increase in the percentage of GFP+ cells in both CB and BM-derived HSPC (FIG. 15A, left panel, rapamycin v. DMSO, p<0.0001; FIG. 15B, left panel, rapamycin v. DMSO, p<0.001), CsA alone performed better, yielding a 3-fold increase in the percentage of GFP+ cells in both CB and BM-derived HSPC (FIG. 15A, left panel, CsA v. DMSO, p<0.0001; FIG. 15B, left panel, CsA v. DMSO, p<0.0001). Furthermore, this increase was significantly higher than that obtained with rapamycin alone in CB-derived HSPC (FIG. 15A, left panel, CsA v. rapamycin, p<0.001). As opposed to CsA, the effect of rapamycin on LV transduction efficiencies was not specific to the HSPC compartment as a similar trend was observed in CD4+ T cells, while it significantly decreased transduction by 2.8-fold in MDM (FIG. 16). Combining the two immunosuppressive compounds together during LV transduction led to a further increase in terms of transduction efficiency in both CB and BM-derived HSPC, in which a 4.5-fold increase was observed in average (FIGS. 15A and 15B, left panels, DMSO vs. CsA+rapamycin, p<0.0001). Observed increases in transduction efficiencies in terms of percentages of GFP+ cells were mirrored by a comparable, if not even greater, increase in terms of VCN measured per cell after two weeks of culture (FIGS. 15A and 15B, right panels). In particular, CsA treatment alone led to a 5- and 7-fold increase in VCN per cell in CB and BM-derived HSPC, respectively.

Similarly to human HSPC, both CsA and rapamycin, as well as their combination, significantly improved transduction also in murine Lin⁻ HSPC (FIG. 29A). No major differences in the transduction levels between the different conditions were observed in murine CD4+ T cells (FIG. 29B).

Figure 17:
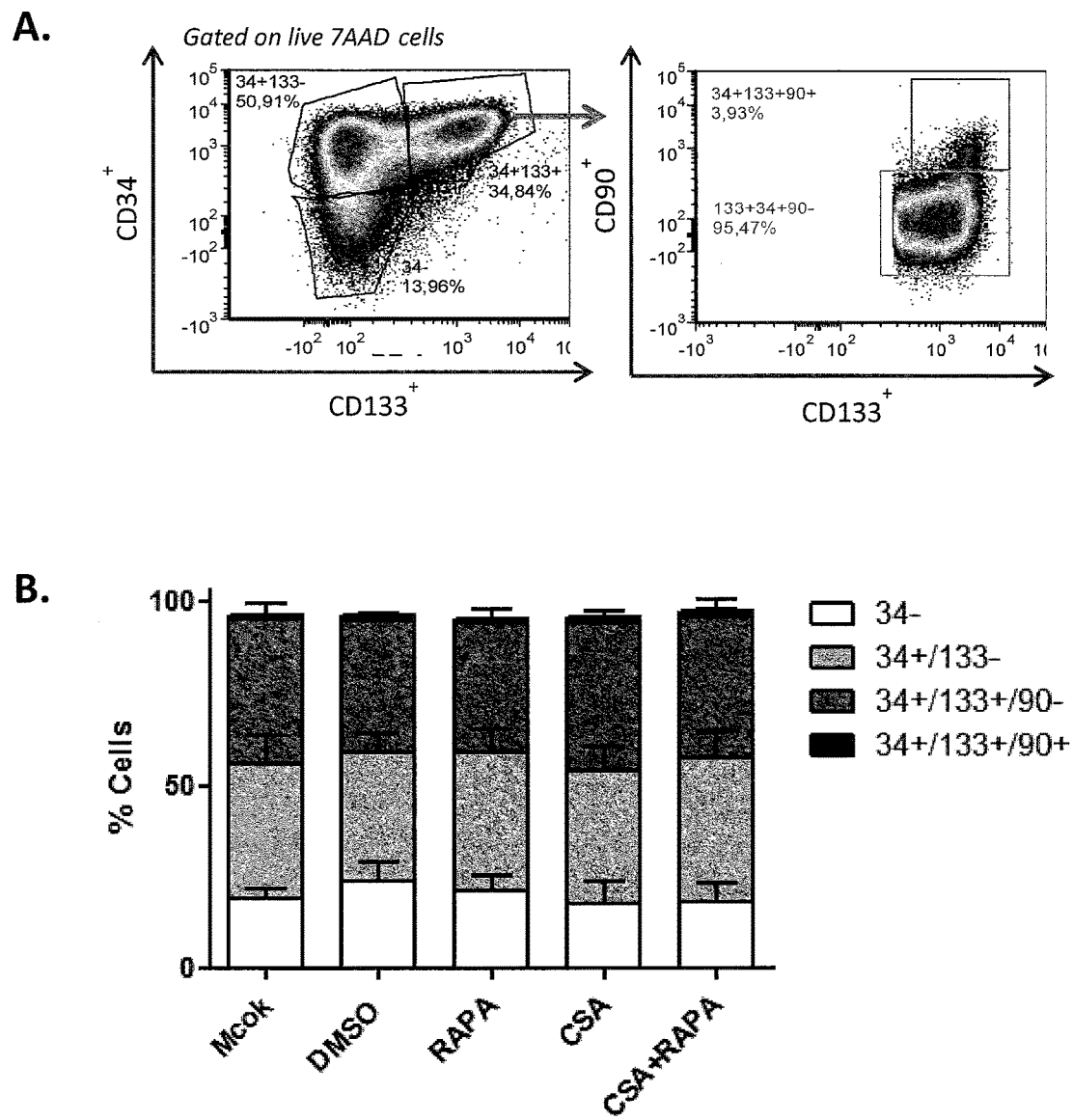
Figure 26:
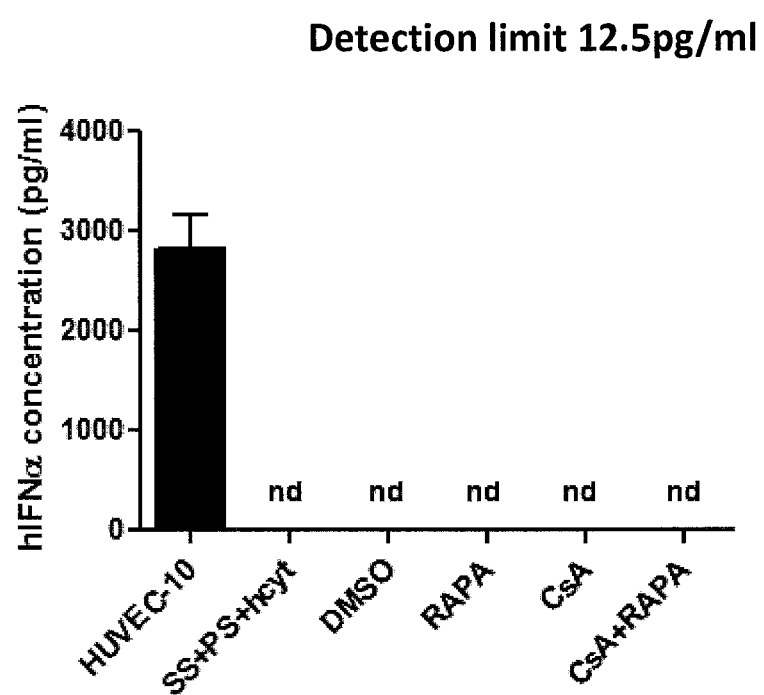

Importantly, we observed that both CsA and rapamycin, as well as their combination, yielded equally improved transduction levels in all HSPC subpopulations ranging from the more committed CD34⁻ progenitors to the most primitive CD34+CD133+CD90+ cells (FIG. 15C), suggesting that both compounds overcome restriction blocks common to all HSPC rather than specific subpopulations. Noteworthy, no significant alterations in the relative percentages of the different subpopulations were observed among the treatments (FIG. 17). Furthermore, based on recent reports suggesting that altering interactions of the HIV-1 core with host factors during the early phases of transduction can lead to aberrant IFN production in MDM (Rasaiyaah, J. et al. (2013) Nature 503: 402-5), we measured IFNα secretion in CB-derived HSPC 24 hours after exposure to CsA/rapamycin (FIG. 26). However, in the context of HSPC, no detectable levels of IFNα could be seen in any of the conditions. Nevertheless, although the combination of CsA and rapamycin gave impressive improvements in terms of transduction efficiencies both in CB and BM-derived HSPCs, some toxicity of this treatment was observed. This was confirmed by reduced cell counts over time and increased staining for apoptotic cells two days post-exposure in CB-derived HSPCs (FIG. 18). Both CsA and rapamycin are reported to induce autophagy (Kondo, Y. et al. (2005) Nature Rev. Cancer 5: 726-34; Werneck, M. B. et al. (2012) Cell Cycle 11: 3997-4008). To investigate whether autophagy could be the common denominator behind the beneficial effect both compounds have on LV transduction, we transduced the CD34+ HSPC in presence or absence of 3-methyladenine (3-MA), an inhibitor of autophagy (Kondo, Y. et al. (2005) Nature Rev. Cancer 5: 726-34). Interestingly, although 3-MA alone had little or no effect on transduction, its combination with both CsA and rapamycin led to a further improvement of transduction both in terms of percentages of GFP+ cells as well as VCN per cell (FIG. 19). Taken together, these results indicate that the combination of CsA and rapamycin seems to improve LV transduction in an additive and autophagy-independent manner both in CB and BM-derived HSPC, suggesting that the two compounds act on distinct pathways hampering LV gene transfer in CD34+ cells.

Figure 30:
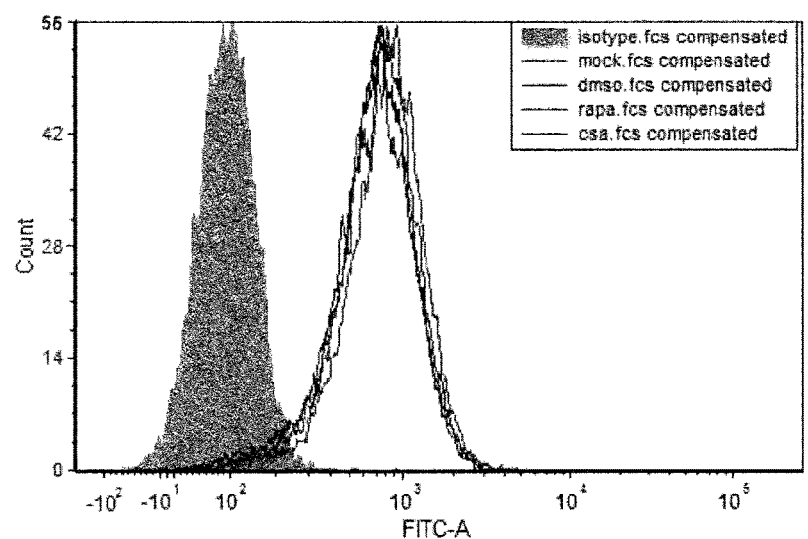

A recent report suggests that quiescent HSPC are poorly permissive to VSV-g-pseudotyped LV transduction because of low levels of expression of its receptor, the low-density lipid receptor (LDL-R). Increased permissivity to transduction upon cytokine-stimulation was shown to correlate with increased LDL-R expression. We examined whether CsA and Rapa could further increase LDL-R levels in cytokine-stimulated human HSPC. No major differences in LDL-R surface expression were observed between the different groups at 6 hours after exposure (FIG. 30).

CsA and Rapamycin do not Alter Colony-Forming Capacity of Vital HSPC in Semi-Solid Culture while Maintaining Efficient Transduction.

Figure 21:
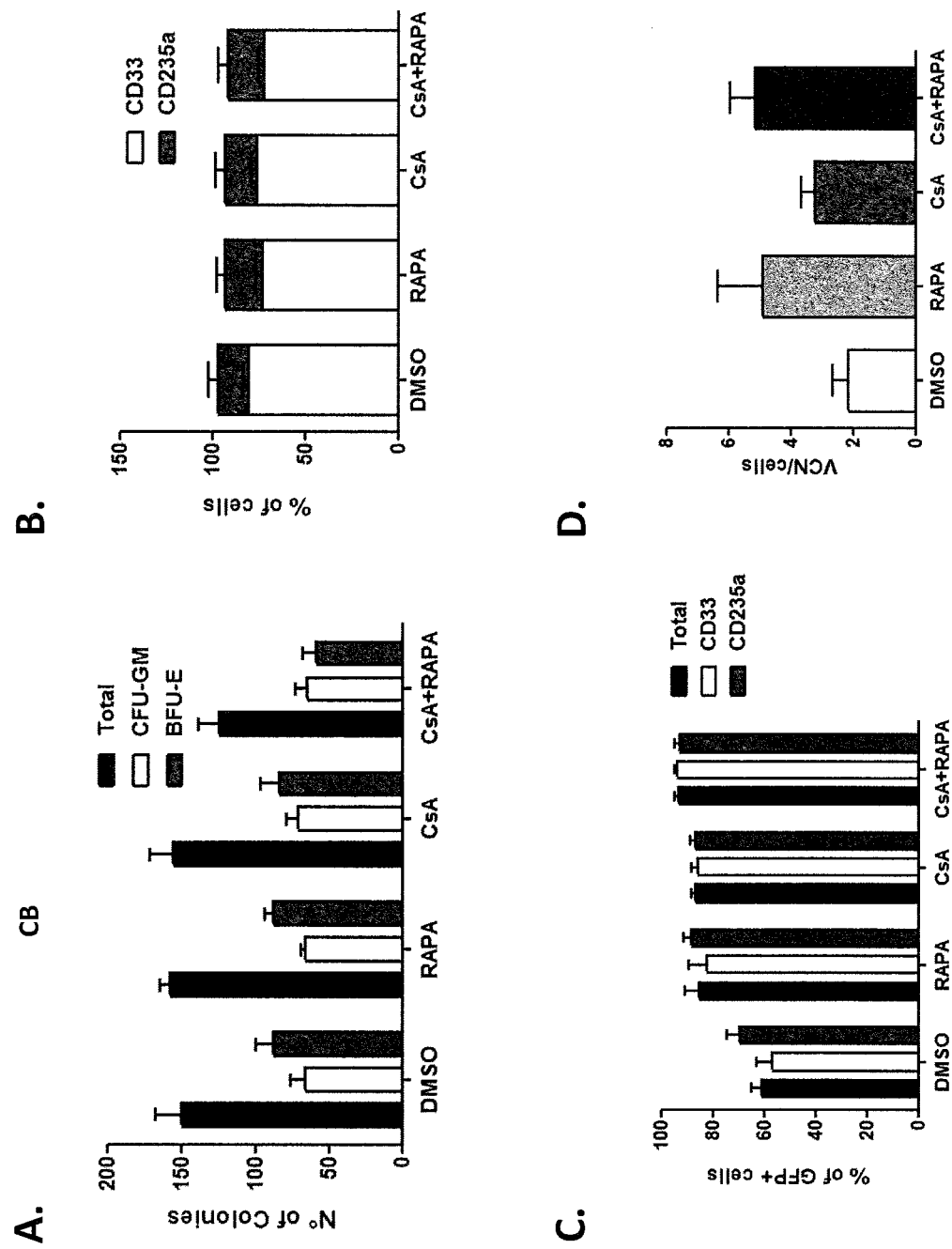

With the perspective of improving LV transduction efficiencies in a clinical setting, we addressed whether CsA and rapamycin are able to improve LV transduction in clonogenic progenitors without hampering their colony-forming capacity. For this purpose, CB-derived CD34+ HSPC were transduced with the GFP-expressing LV at a MOI of 10, in the presence or absence of CsA/rapamycin, followed by plating of vital cells the day after in semi-solid methylcellulose. No significant differences were observed between the different treatments in the number of total, colony-forming unit-granulocyte/macrophage (CFU-GM) (myeloid) and burst-forming unit erythroid (BFU-E) (erythroid) colonies deriving from CB CD34+ cells, although a trend towards lower CFU counts was seen for the combination CsA+rapannycin (FIG. 21A). Similarly, the percentages of myeloid and erythroid progenitors measured by FACS after two weeks of culture did not vary among the different treatments (FIG. 21B). Importantly, the percentage of GFP+ cells was significantly increased within both total as well as myeloid erythroid clonogenic progenitors, reaching 88%±1.62 in all treatment groups as compared to an average of 62%±3.03 with DMSO, (FIG. 21C). Increased transduction efficiency was confirmed by measurement of VCN per cell on bulk colonies isolated after 14 days of culture (FIG. 21D). These results indicate that improved LV transduction efficiencies provided by both CsA as well as rapamycin are maintained also in vital clonogenic progenitors without affecting their colony-forming capacity.

Figure 22:
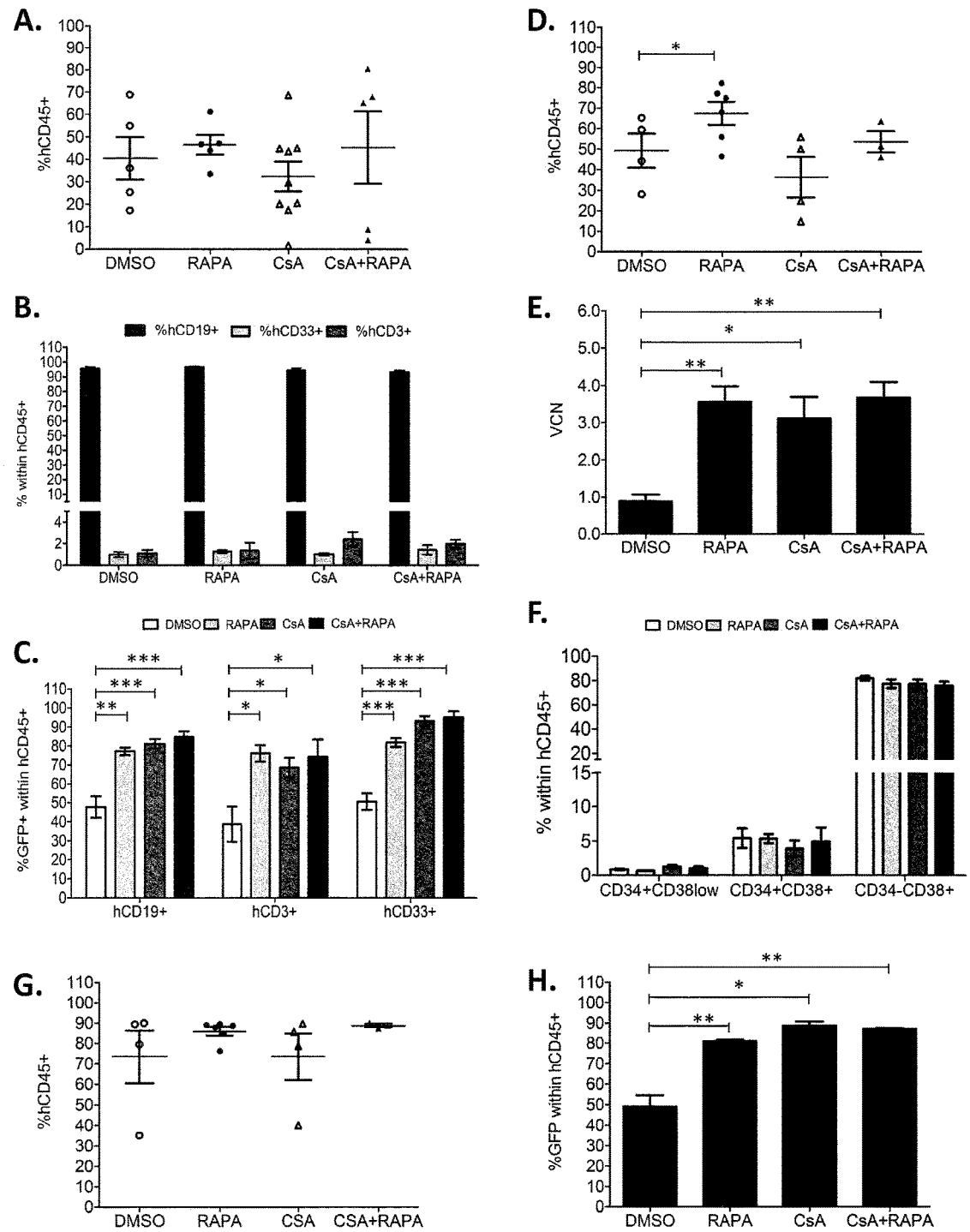

CsA and Rapamycin Improve Transduction Efficiency of Long-Term Repopulating HSPC without Affecting their Engraftment and Repopulation Capacity In order to assess the impact of the two immunosuppressive compounds on LV transduction, engraftment and repopulation capacity of long-term repopulating HSPC, CB-derived CD34+ cells were transduced in the presence or absence of CsA/rapamycin and transplanted the day after in 10 week-old NSG mice (130,000 cells per mouse). FACS analysis of the peripheral blood of mice at 11 weeks after transplant showed similar engraftment levels of human CD45+ cells (~40%) in all treatment groups (FIG. 22A) and no significant differences were observed in the percentages of human B (hCD19+), T (hCD3+) and myeloid cells (hCD33+) within the human CD45+ population (FIG. 22B). Mice transplanted with CsA–, rapamycin– as well as CsA+rapamycin-treated human HSPC showed comparable high levels of transduction (around 80% of GFP+/hCD45+ cells) in all the different human haematopoietic lineages (FIG. 22C) that were significantly higher with respect to the DMSO-treated control group (CsA 81±3, rapamycin 78±2 or CsA+rapamycin 85±3 v. DMSO 48±6, p=0.0001).

Figure 23:
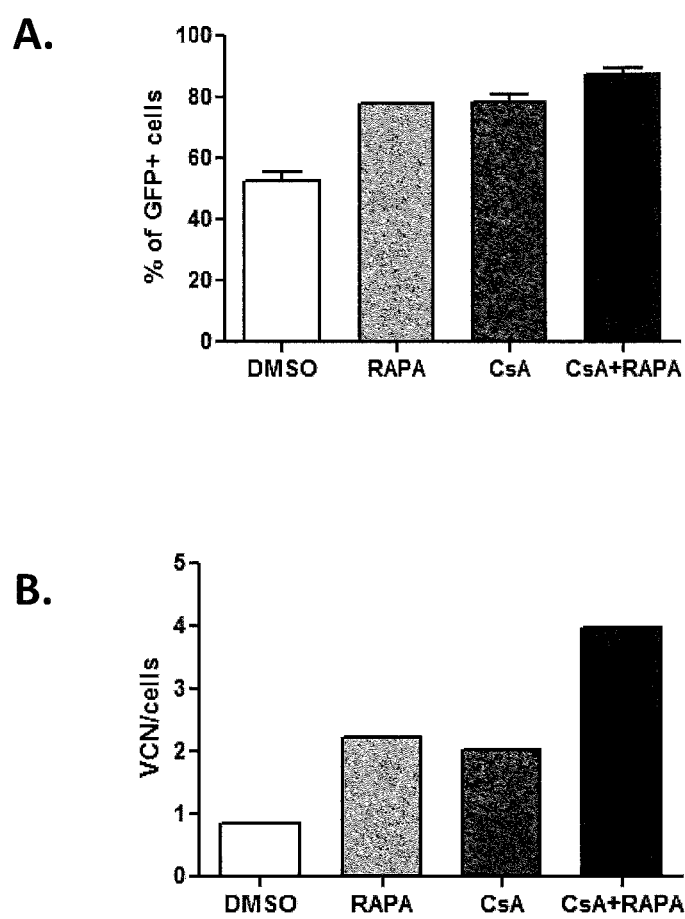

The engraftment levels of human CD45+ cells in the BM of mice at 20 weeks post-transplant were comparable among the DMSO–, CsA–, and CsA+rapamycin-treatment groups (46±5%), while the rapamycin-treatment group showed a statistically significant increase in the levels of engraftment with respect to controls (p<0.047 v. DMSO) (FIG. 22D). Moreover, the VCN in the BM cells of mice transplanted with CsA, rapamycin and CsA+rapamycin-treated HSPC was significantly higher with respect to the VCN found in BM cells of the mice of the DMSO treatment group (FIG. 22F, CsA 3.1±0.6, rapamycin 3.6±0.4 or CsA+rapamycin 3.5±0.4 v. DMSO 0.9±0.2, p<0.002, FIG. 23B). Finally, among all treatment groups, we did not detect any significant difference in the amount of phenotypically identified cell subsets enriched for HSCs (CD34+CD38$^{low}$), progenitors (CD34+CD38+) and differentiated cells (CD34−CD38+) that on average accounted for 1.0±0.2, 4.9±0.8 and 78.0±3.1, respectively (FIGS. 22E and 23A).

Figure 20:
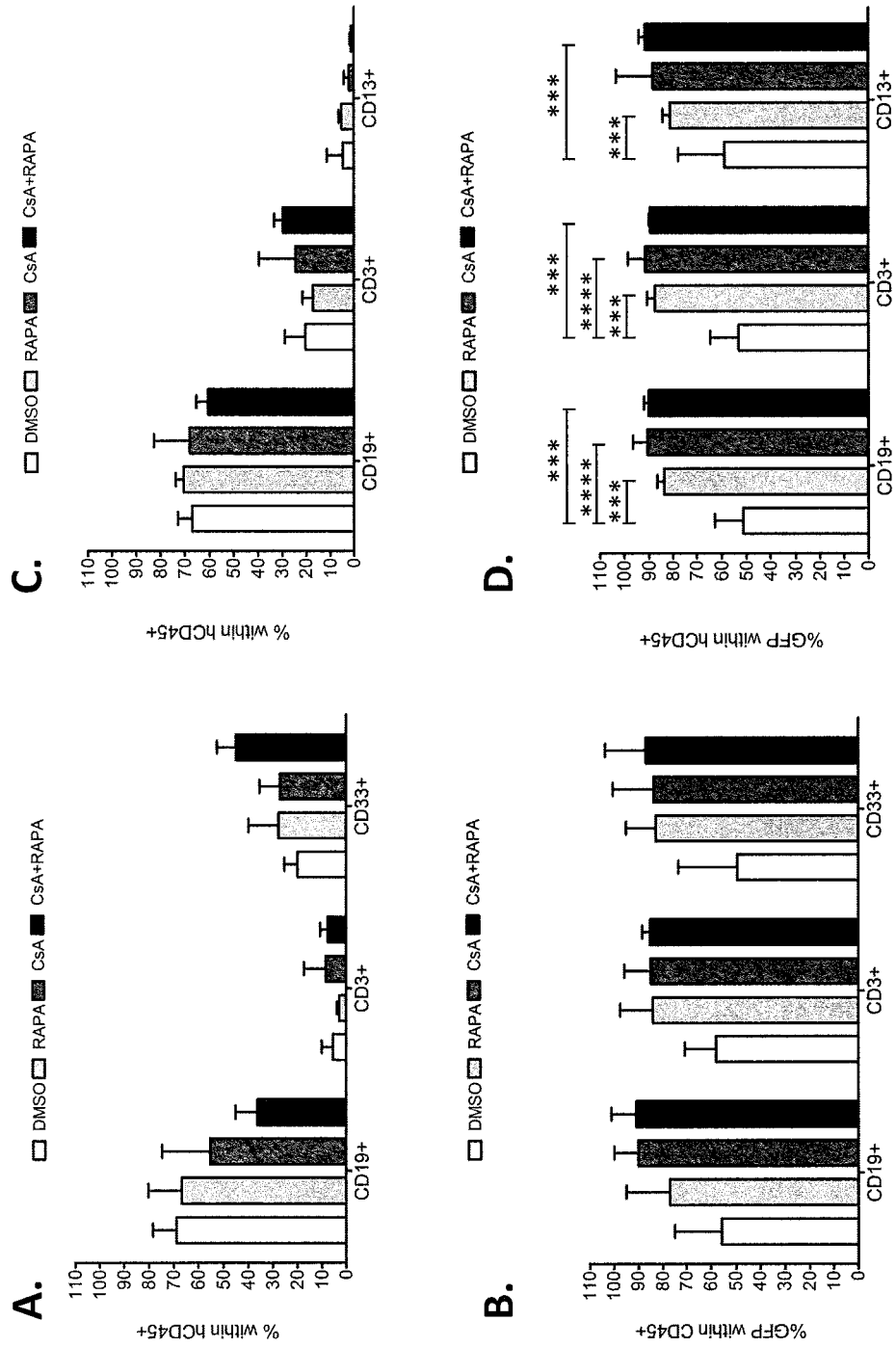

In the spleen of the transplanted mice, the levels of total human CD45+ cells and of the different haematopoietic lineages (B, T and myeloid cells) were comparable among the different groups (FIGS. 22G and 20C). Moreover, also in the spleen of transplanted mice, we detected a significant increase in the overall percentage of GFP+ cells in the CsA, rapamycin and CsA+rapamycin treatment groups with respect to DMSO treatment and this was maintained among the different lineages (FIG. 22H, CsA 88.7±2, rapamycin 80.8±1 or CsA+rapamycin 87.0±0.6 v. DMSO 49.0±5, p<0.0001 FIG. 20D). The transduction efficiencies observed in vivo in terms of percentages of GFP+ cells and VCN were comparable to those observed in liquid culture seeded in parallel with the transplanted cells for CsA, rapamycin and their combination (FIG. 24A).

Overall, these results indicate that both CsA and rapamycin treatments improve LV-mediated gene transfer in CB-derived CD34+ without altering their short-term and long-term repopulating ability.

Both CsA and Rapamycin Improve Transduction Efficiency of Clinical Grade LV

We also tested the capacity of both CsA and rapamycin to improve transduction efficiency of a clinical grade SINLV. For this purpose, cytokine-stimulated CB-derived CD34+ cells were transduced with increasing MOIs of a PGK-GFP SINLV produced by Molmed SpA utilising the same large-scale setting and downstream processing that has been applied in the context of recent clinical trials conducted at our institute using SINLVs as delivery vehicles of the therapeutic gene (Biffi, A. et al. (2013) Science 341: 1233158; Aiuti, A. et al. (2013) Science 341: 1233151). These procedures efficiently remove as much of the contaminant by-products, such as plasmid DNA and cell debris, as possible but render the vector preparations less infectious than the standard laboratory-grade stocks (Merten, O. W. et al. (2011) Human Gene Ther. 22: 343-56). Importantly, we observed that both CsA and rapamycin yielded increased transduction efficiencies also in this context reaching up to 60% of GFP+ cells in rapamycin-treated, 70% of GFP+ cells in CsA-treated and 78% of GFP+ cells in CsA+rapamycin treated HSPC at a MOI of 10 (FIG. 25A, p<0.01). This increase was accompanied by an almost 10-fold increase in VCN per cell for both CsA and CsA+rapamycin-treated cells at an MOI of 10 (FIG. 25B).

Figure 27:
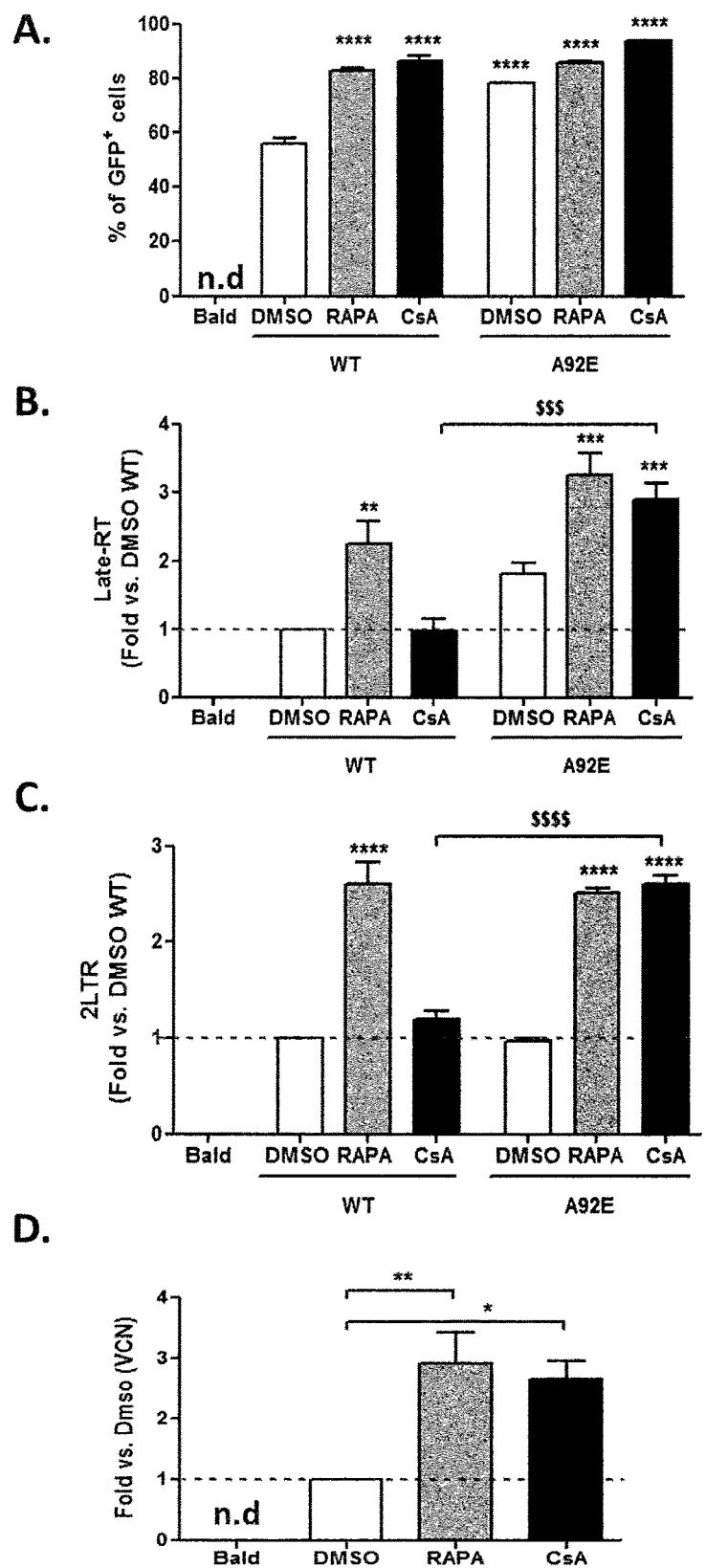
Figure 32:
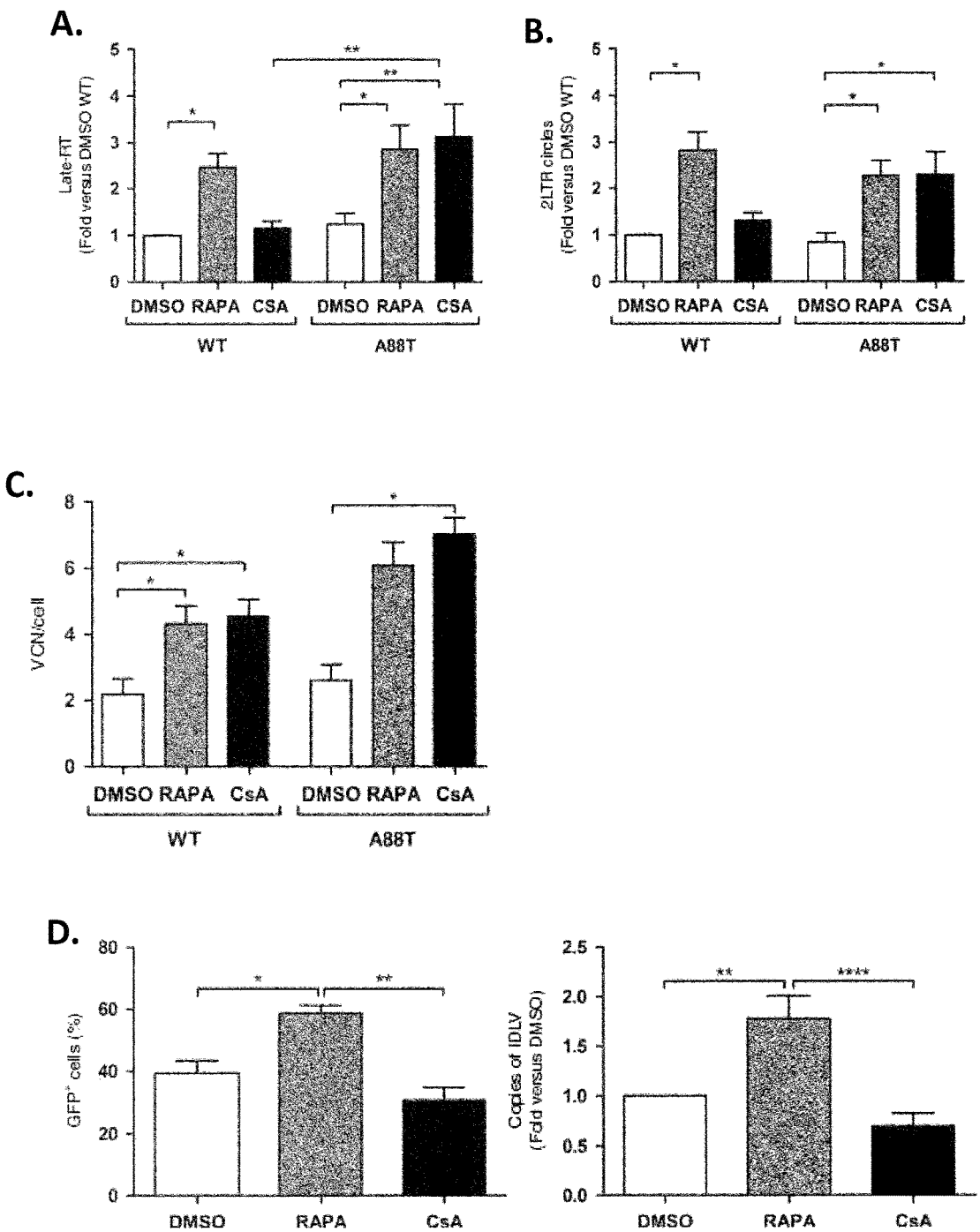

The Effects of CsA and Rapamycin are LV-Specific and Impact on Separate Steps of the Viral Life Cycle In order to better understand the host and viral partners potentially involved in CsA/rapamycin-mediated improvement of transduction in HSPC, we first tested whether these compounds could also increase γ-retroviral gene transfer in HSPC. For this purpose both CB and BM-derived CD34+ cells were transduced with a GFP-expressing γ-retroviral SIN vector (SINRV) at a MOI of 10, in the presence or absence of CsA/rapamycin. Interestingly, neither compound was able to significantly increase the percentage of GFP+ cells in either CB or BM-derived HSPC (FIG. 24), suggesting that LV-specific pathways or viral components are involved in the beneficial effects observed for SINLV. Finally, to further dissect the mechanisms through which CsA and Rapa increase LV transduction in HSPC, we tracked the LV genome fate by measuring viral DNA replication intermediates at an early time post-transduction in rapamycin, CsA and control treated CB-derived CD34+ cells transduced with LV harboring either WT, A88T (FIG. 32) or A92E (FIG. 27) viral CA. Rapamycin led to a two to threefold increase in late-RT products independently of the CA (FIGS. 27B and 32A, rapamycin vs. DMSO, p<0.05), followed by a consequent increase in both 2-long-terminal-repeat (2LTR) circles (FIGS. 27C and 32B, rapamycin vs. DMSO, p<0.01 for WT, p<0.05 for A88T), surrogate of nuclear entry of HIV-1 DNA (De Iaco A, Luban J. Inhibition of HIV-1 infection by TNPO3 depletion is determined by capsid and detectable after viral cDNA enters the nucleus. Retrovirology. 2011; 8: 98.), as well as in integrated vector copies (FIGS. 27D and 32C, rapamycin vs. DMSO). Interestingly, CsA did not alter late-RT nor 2LTR circle formation for the WT LV (FIGS. 32A,B) while a 2 to 3-fold increase in both products was observed for the A88T LV (FIGS. 32A,B, CsA vs. DMSO, p<0.01 and p<0.05, respectively) and A92E LV (FIGS. 27B and C). CsA lead to a significant increase in the amount of integrated proviral copies for all vectors (FIGS. 27D and 32C, CsA vs. DMSO, p<0.05) and the A88T CA mutant LV yielded a higher VCN/cell as compared to WT vector in presence of CsA (FIGS. 31 and 32C, CsA WT vs. CsA A88T, p<0.01).

These results suggest that rapamycin improves LV transduction during the early phases of the viral life cycle while CsA seems to act only after nuclear entry of the pre-integration complex.

Discussion

Two immunosuppressive compounds, cyclosporin A (CsA) and rapamycin (Rapa), significantly improve LV transduction efficiency in human HSPC, acting on distinct steps of the LV life cycle. Interestingly, the effects of CsA were HSPC-specific and opposite to that occurring in differentiated haematopoietic cell lines and primary cells.

CsA has revolutionised human organ transplantation due to its ability to block the activation of lymphocytes and other immune cells. Besides its immunomodulatory capacity, CsA is also well known in the field of HIV-1 research as a compound interfering with the early steps of the lentiviral life cycle in human cells due to its capacity to disrupt the interaction between the host chaperone cyclophilin A (CypA) and the viral capsid (CA) (Sokolskaja, E. et al. (2006) Curr. Opin. Microbiol. 9: 404-8; Towers, G. J. (2007) Retrovirology 4: 40).

Interestingly, we observed that CsA is able to improve LV transduction at concentrations above 1 µM, in a range required to disrupt CypA-CA interaction (Luban, J. et al. (1993) Cell 73: 1067-78) rather than to act as an immunosuppressor (Colgan, J. et al. (2005) J. Immunol. 174: 6030-8). Indeed, the calcineurin-mediated immunomodulatory signal transduction is unlikely to be involved in the effects of CsA on LV transduction in HSPC, as FK506, another compound inhibiting the same pathway, did not affect LV gene transfer in these cells.

The disruption of the CypA-CA interaction by CsA is thought to lead to premature uncoating of the viral core and inhibition of infection, as we also observed in differentiated CD4+ T cells and MDM, although the exact mechanisms remain unclear. Remarkably, we have observed exactly the opposite effect of CsA in the HSPC compartment in which, instead of abrogating transduction, CsA leads to a consistent 3-fold increase in the efficiency of LV gene transfer. Interestingly, this type of CsA-mediated benefit is usually observed in the context of cross-species infection due to disruption of the interaction of the lentiviral core with the host restriction factor TRIM5α (Strebel, K. et al. (2009) BMC Medicine 7: 48). However, human TRIM5α notoriously has very poor HIV-1 restrictive capacity (Towers, G. J. (2007) Retrovirology 4: 40), although a very recent report suggests that variable levels of TRIM5α expression in human HSPCs could correlate with donor-dependent variability in permissivity to LV transduction (Evans, M. E. et al. (2013) TRIM5alpha Variations Influence Transduction Efficiency With Lentiviral Vectors in Both Human and Rhesus CD34 Cells In Vitro and In Vivo, Molecular therapy: The Journal of the American Society of Gene Therapy). In this regard, we should point out that the CB-derived HSPC tested for CsA and rapamycin-mediated effects on transduction were donor-matched with the CD4+ T cells and MDM, in which the two compounds had very opposite effects, rendering it difficult to reconcile our observations with a donor-dependent TRIM5α restriction block in HSPC.

To investigate potential involvement of the LV capsid in CsA-mediated effects, we generated a series of packaging constructs each harbouring a specific CA point-mutation with known properties regarding its capacity to bind to CypA, interact with the nuclear pore complex, depend on CsA (Schaller, T. et al. (2011) PLoS Pathog. 7: e1002439) or escape TRIM5α-mediated restriction (Veillette, M. et al. (2013) Retrovirology 10: 25). The chosen point-mutants had never been tested in HSPC to the best of our knowledge, although efforts to manipulate the LV core with the aim of improving transduction have been reported in the past (Kahl, C. A. et al. (2008) Gene Therapy 15: 1079-89; Uchida, N. et al. (2013) Exp. Hematol. 41: 779-88 e771). Although cell-type dependent effects of CsA have been reported (De Iaco, A. et al. (2014) Retrovirology 11: 11; Sokolskaja, E. et al. (2004) J. Virol. 78: 12800-8; Song, C. et al. (2007) J. Virol. 81: 11946-56; Takeuchi, H. et al. (2012) Retrovirology 9: 3) the only settings in which CsA-treatment has been previously shown to promote HIV-1 replication or transduction have regarded either SIV infection in the context of human cells (Hatziioannou, T. et al. (2004) Proc. Natl. Acad. Sci. USA 101: 10774-9; Ylinen, L. M. et al. (2005) J. Virol. 79: 11580-7), HIV infection in the context of simian cells (Stremlau, M. et al. (2004) Nature 427: 848-53) or specific HIV-1 CA mutants in human cell lines (De Iaco, A. et al. (2014) Retrovirology 11: 11; Song, C. et al. (2007) J. Virol. 81: 11946-56), as we observed for the P90A and A92E CA mutant in CsA-exposed CD4+ T cells. In CD34+ cells, all tested CA mutants remained sensitive to CsA-mediated effects, suggesting that CsA mediates CA independent relief of LV restriction in human HSPCs. In agreement with this observation, a previous study has shown that proteasomal inhibition increases LV transduction efficiencies in human and murine HSPCs independently of the CypA-CA interaction as the CypA-independent G89V CA mutant (Keckesova, Z. et al. (2006) J. Virol. 80: 4683-90) remains sensitive to proteasomal inhibition-mediated improvement of transduction (Santoni de Sio, F. R. et al. (2008) Stem Cells 26: 2142-52). Interestingly however, we observed that mutating the CypA binding pocket of the LV CA did alter the impact of CsA on the viral replication intermediates in human HSPC and the A88T capsid mutant performed better than the WT vector in presence of CsA. These data suggest that also the CA-CypA interaction may be involved in LV restriction in HSPC.

Nevertheless, two point mutations within the CypA binding pocket of the LV CA provided a two-fold advantage compared to WT LV alone and in addition to CsA in HSPC. This increase in transduction is likely due to escape from an early block as A92E LV showed increased late-RT products as compared to WT LV. Lack of increase in 2LTR circles despite increased VCN could be due to more efficient integration kinetics. Unlike for WT LV, CsA increased both late-RT products as well as nuclear import for A92E.

Although several forms of experimental evidence suggest that CypA protects HIV-1 from an unknown antiviral activity in human cells (Sokolskaja, E. et al. (2006) Curr. Opin. Microbiol. 9: 404-8; Li, Y. et al. (2009) J. Virol. 83: 10951-62), it is tempting to speculate based on our observations that in the context of human HSPC, CypA could actually mediate restriction towards LV or that human CD34+ cells express a yet unidentified restriction factor binding the viral CA. Nevertheless, the specific involvement of CypA remains to be addressed as also do other host immunophilins which have been shown to bind to CsA (Luban, J. et al. (1993) Cell 73: 1067-78; Frausto, S. D. et al. (2013) Viruses 5: 1684-701; Nagy, P. D. et al. (2011) Virology 411: 374-82). Noteworthy, previous efforts to improve LV transduction efficiency in human HSPC through modulation of the viral CA-CypA interaction have shown a negative impact of CsA on transduction efficiencies on these cells (Kahl, C. A. et al. (2008) Gene Therapy 15: 1079-89;

Uchida, N. et al. (2013) *Exp. Hematol.* 41: 779-88 e771). Interestingly, the effects of CsA were HSPC-specific and opposite to what occurs in differentiated hematopoietic cells. We observed that CsA was able to improve LV transduction only at high concentrations required to disrupt CypA-CA interaction (Luban, J. et al. (1993) *Cell* 73: 1067-78) but not in its nanomolar immunosuppressive range (Colgan, J. et al, (2005) *J. Immunol.* 174: 6030-8). This concentration-dependent impact of CsA on LV transduction could explain, at least in part, why in previous studies it did not improve LV transduction in HSPC, as low concentrations were used (Kahl, C. A. et al. (2008) *Gene Therapy* 15: 1079-89; and Uchida, N. et al. (2013) *Exp. Hematol.* 41: 779-88 e771).

Interestingly, CsA did not impact on late-RT nor 2LTR circle formation during WT LV transduction, while an increase was observed in integrated proviral copies. In this regard, recent reports describe how the IFN-induced human MxB protein is able to potently reduce the permissiveness of cells lines to HIV-1 (Goujon, C. et al. (2013) *Nature* 502: 559-62; Kane, M. et al. (2013) *Nature* 502: 563-6; Liu, Z. et al. (2013) *Cell Host Microbe* 14: 398-410). In one study, reverse transcription of the HIV-1 RNA within incoming particles to cDNA occurred normally, whereas integration of HIV-1 proviruses into the host cell genome was markedly diminished in MxB-expressing cells. However, an MxB-dependent reduction of 2LTR circles was also observed in two other studies (Goujon, C. et al. (2013) *Nature* 502: 559-62; Kane, M. et al. (2013) *Nature* 502: 563-6). These results place the anti-HIV activity of MxB in the post-entry phase of HIV-1 infection after cDNA synthesis, possibly involving nuclear import, nuclear stability and/or integration of the viral cDNA. The viral capsid was shown to govern HIV-1 sensitivity to MxB as the A88T CA mutant escaped MxB restriction (Goujon, C. et al. (2013) *Nature* 502: 559-62; Kane, M. et al. (2013) *Nature* 502: 563-6; Liu, Z. et al. (2013) *Cell Host Microbe* 14: 398-410) and the action of MxB might be associated with that of CypA, as silencing of CypA expression or disruption of the CA-CypA interaction by addition CsA abrogated the anti-HIV activity of MxB (Liu, Z. et al. (2013) *Cell Host Microbe* 14: 398-410).

Based on our observations that CsA most likely affects post-nuclear entry steps of the WT LV life cycle, host factors potentially directly impairing the HIV-1 integration process could be involved. In this regard, it has recently been demonstrated that the host factor TRIM28 (also known as KAP-1), previously discovered to be involved in the transcriptional silencing of endogenous retroviruses and MLV in murine embryonic stem cells (Rowe, H. M. et al. (2010) *Nature* 463: 237-40; Wolf, D. et al. (2007) *Cell* 131: 46-57), inhibits HIV-1 integration through acetylation of the viral integrase in HeLa cells and primary CD4$^+$ T cells (Allouch, A. et al. (2011) *Cell Host Microbe* 9: 484-95). Similar mechanisms, whether KAP-1 mediated or not, could be involved in limiting the LV integration in HSPC.

The rapamycin-associated host immunophilin FKBP12 is unlikely to be involved in rapamycin-mediated effects on LV transduction in HSPC, as another inhibitor of this PPlase, FK506, did not lead to improved transduction. Interestingly, rapamycin has been shown to abrogate the ability of TLR7 and TLR9 agonists to induce IFNα/β in plasmacytoid dendritic cells (pDCs) through mTOR inhibition and consequent disruption of the MyD88-TLR complex (Cao, W. et al. (2008) *Nat. Immunol.* 9: 1157-64; Colina, R. et al. (2008) *Nature* 452: 323-8). In this regard, recent reports indicate that LVs activate myeloid dendritic cells (DC) through TLR 3 and 7 (Breckpot, K. et al. (2010) *J. Virol.* 84: 5627-36) and trigger TLR-dependent and independent innate signalling in murine hepatocytes, leading to decreased transduction (Agudo, J. et al. (2012) A TLR and Non-TLR Mediated Innate Response to Lentiviruses Restricts Hepatocyte Entry and Can be Ameliorated by Pharmacological Blockade. *Molecular therapy: The Journal of the American Society of Gene Therapy*). Along these lines, inhibition of TLR signalling in human Natural Killer (NK) cells can lead to improved transduction (Sutlu, T. et al. (2012) Inhibition of Intracellular Antiviral Defense Mechanisms Augments Lentiviral Transduction of Human Natural Killer Cells: Implications for Gene Therapy. *Human Gene Therapy*). Noteworthy, TLRs are present on the surface of haematopoietic progenitors and actively signal upon stimulation (Nagai, Y. et al. (2006) *Immunity* 24: 801-12; Esplin, B. L. et al. (2011) *J. Immunol.* 186: 5367-75). Moreover, HIV-1 infection has been shown to be blocked after efficient entry but prior to reverse transcription in TLR-ligand activated primary human macrophages (Wang, X. et al. (2011) PLoS One 6: e24193). In this regard, we observed that rapamycin acts on the early phases of the lentiviral transduction based on an observed increase in late-RT products. Although no reports regarding LV-mediated signal transduction in human HSPCs is currently available, it is possible to envision that rapamycin could prevent TLR-mediated activation of innate immune responses in human HSPCs leading to improved transduction efficiency.

Rapamycin induces autophagy in a variety of cell types (Sabers, C. J. et al. (1995) *J. Biol. Chem.* 270: 815-22; Sarkar, S. et al. (2008) *Molecular bioSystems* 4: 895-901). Interestingly, CsA and proteasomal inhibition (previously shown to increase LV transduction efficiency in human HSPC (Santoni de Sio, F. R. et al. (2008) *Stem Cells* 26: 2142-52; Leuci, V. et al, (2011) *J. Biotechnol.* 156: 218-26) have also been shown to increase autophagy (Werneck, M. B. et al. (2012) *Cell Cycle* 11: 3997-4008; Zhu, K. et al. (2010) *Oncogene* 29: 451-62). Therefore, it was tempting to speculate that autophagy could somehow be the common denominator behind these different treatments, all yielding more efficient gene transfer in human HSPCs. In this setting, the use of an autophagy inhibitor could have been expected to impair rapamycin and CsA-mediated increase in LV transduction in HSPC. However, we saw quite the opposite as combination of the autophagy inhibitor 3-methyladenine (3-MA) together with either rapamycin or CsA actually further improved gene transfer efficiency, despite some toxicity. As autophagy-inducing agents have been shown to inhibit HIV replication in primary human MDM (Rubinsztein, D. C. et al. (2012) *Nat. Rev. Drug Discovery* 11: 709-30; Campbell, G. R. et al. (2011) *J. Biol. Chem.* 286: 18890-902), it is therefore reasonable to think that rapamycin/CsA-mediated increase in autophagy could be deleterious for LV transduction, despite an overall improved gene transfer yield, and that blocking it will further improved transduction efficiency. However, no increase with 3-MA alone was observed suggesting that basal levels of autophagy are not sufficient per se to impact on LV transduction in HSPC, although autophagy has been shown to be essential for the life-long maintenance of the haematopoietic stem cell compartment and for supporting an old, failing blood system (Warr, M. R. et al. (2013) *Nature* 494: 323-7).

The CD34$^+$ HSPC population is in reality comprised of only a minority of true stem cells endowed with self-renewal and repopulating capacity (Doulatov, S. et al. (2012) *Cell Stem Cell* 10: 120-36). The vast majority of the cells are more committed progenitors that will be lost after initial engraftment and will not contribute to sustained haematopoiesis in a transplanted individual. Based on these considerations, our observation that CsA and rapamycin release LV restriction not only in a fraction of the bulk CD34+ HSPC but in all subpopulations, including the most primitive CD34+CD133+CD90+ is of importance in view of potential applications of CsA/rapamycin in clinical gene therapy settings. Along these lines, no differences in transduction efficiencies were measured among all human peripheral blood subsets monitored in transplanted NSG mice, indicating overall improved gene transfer in the entire haematopoietic compartment in vivo. Improved gene transfer efficiency was obtained also with a SINLV that had been processed with the same downstream protocols as vectors used in current clinical trials (Biffi, A. et al. (2013) Science 341: 1233158; Aiuti, A. et al. (2013) Science 341: 1233151), reaching a robust 70% of transduction efficiency at the low MOI of 10. This observation is of particular value keeping in mind that clinical-grade vectors usually suffer from lower infectivity as compared to laboratory-grade preparations (Merten, O. W. et al. (2011) Human Gene Therapy 22: 343-56). Importantly, increased transduction efficiencies were maintained long-term in vivo and no effects on HSPC engraftment or repopulation capacities were observed among the different treatment groups, except for the rapamycin-treated cells. Indeed, in line with previous reports (Rohrabaugh, S. L. et al. (2011) Blood Cells, Molecules & Diseases 46: 318-20; Huang, J. et al. (2012) Nat. Medicine 18: 1778-85), we saw a modest but statistically significant increase in HSPC engraftment in NSG mice in the rapamycin-treated group, that could be of further benefit in clinical settings in which engraftment kinetics are crucial for successful gene therapy outcome (Naldini, L. (2011) Nat. Rev. Genetics 12: 301-15).

Overall, our results provide an important step forward in the development of more efficient LV gene therapy protocols and bring insight into the LV restriction bottlenecks hampering lentiviral gene transfer in human HSPCs.

All publications mentioned in the above specification are herein incorporated by reference. Various modifications and variations of the described uses and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method of transducing a population of human haematopoietic stem and/or progenitor cells comprising the steps of:
   a) contacting the population of cells with cyclosporin A (CsA) at a concentration of about 5-50 μM; and
   b) transducing the population of cells with a HIV-1, HIV-2, FIV, BIV, EIAV, CAEV or visna lentiviral vector, wherein the vector does not comprise SIV capsid proteins;
   wherein transduction efficiency is increased in comparison to transduction in the absence of the CsA.

2. The method of claim 1 wherein steps (a) and (b) are carried out ex vivo or in vitro.

3. The method of claim 1, wherein the percentage of haematopoietic stem and/or progenitor cells transduced by the vector is increased and/or the vector copy number per cell is increased.

4. The method of claim 1, wherein the vector comprises a capsid comprising glutamic acid at a position analogous to amino acid 92 and/or threonine at a position analogous to amino acid 88 of SEQ ID NO: 1, wherein the N-terminal proline of SEQ ID NO: 1 is assigned to be position 1.

5. The method of claim 1, wherein the cyclosporin A (CsA) is at a concentration of about 6-15 μM.

6. The method of claim 1, wherein the population of cells is contacted with cyclosporin A (CsA) in combination with rapamycin.

7. The method of claim 1, wherein the population of cells is contacted with cyclosporin A (CsA) in combination with 3-methyladenine (3-MA).

8. The method of claim 1, wherein the population of haematopoietic stem and/or progenitor cells is obtained from mobilised peripheral blood, bone marrow or umbilical cord blood.

9. The method of claim 1, comprising a further step of enriching the population for haematopoietic stem and/or progenitor cells.

10. A method of gene therapy comprising the steps of:
    a) transducing a population of human haematopoietic stem and/or progenitor cells according to the method of claim 1; and
    b) administering the transduced cells to a subject.

11. The method of claim 10 wherein the transduced cells are administered to a subject as part of an autologous stem cell transplant procedure or an allogeneic stem cell transplant procedure.

12. A method of transducing a population of haematopoietic stem and/or progenitor cells with a HIV-1, HIV-2, FIV, BIV, EIAV, CAEV or visna lentiviral vector, wherein the vector comprises a capsid comprising glutamic acid at a position analogous to amino acid 92 and/or threonine at a position analogous to amino acid 88 of SEQ ID NO: 1, wherein the N-terminal proline of SEQ ID NO: 1 is assigned to be position 1.

13. The method of claim 12 wherein the transduction is carried out ex vivo or in vitro.

14. The method of claim 1, wherein the lentiviral vector is a HIV-1 vector.

15. The method of claim 1, wherein the lentiviral vector is a wild-type HIV-1 vector.

* * * * *

SEQUENCE LISTING

```
<160> NUMBER OF SEQ ID NOS: 24

<210> SEQ ID NO 1
<211> LENGTH: 230
<212> TYPE: PRT
<213> ORGANISM: Artificial Sequence
<220> FEATURE:
<223> OTHER INFORMATION: Sequence of mature capsid derived from the
      pMDLg/pRRE

<400> SEQUENCE: 1

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr His Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
```

```
                    180                 185                 190
Asn Ala Asn Pro Asp Cys Lys Thr Ile Leu Lys Ala Leu Gly Pro Gly
            195                 200                 205

Ala Thr Leu Glu Glu Met Met Thr Ala Cys Gln Gly Val Gly Gly Pro
        210                 215                 220

Gly His Lys Ala Arg Val
225                 230
```

```
<210> SEQ ID NO 2
<211> LENGTH: 19
<212> TYPE: DNA
<213> ORGANISM: Artificial Sequence
<220> FEATURE:
<223> OTHER INFORMATION: Primer LATE RT (5NC2rev)

<400> SEQUENCE: 2
gagtcctgcg tcgagagag                                               19

<210> SEQ ID NO 3
<211> LENGTH: 23
<212> TYPE: DNA
<213> ORGANISM: Artificial Sequence
<220> FEATURE:
<223> OTHER INFORMATION: Primer LATE RT fw DU3 sense

<400> SEQUENCE: 3
tcactcccaa cgaagacaag atc                                          23

<210> SEQ ID NO 4
<211> LENGTH: 25
<212> TYPE: DNA
<213> ORGANISM: Artificial Sequence
<220> FEATURE:
<223> OTHER INFORMATION: Primer 2junct

<400> SEQUENCE: 4
cagtgtggaa aatctctagc agtac                                        25

<210> SEQ ID NO 5
<211> LENGTH: 21
<212> TYPE: DNA
<213> ORGANISM: Artificial Sequence
<220> FEATURE:
<223> OTHER INFORMATION: Primer J2 rev

<400> SEQUENCE: 5
gccgtgcgcg cttcagcaag c                                            21

<210> SEQ ID NO 6
<211> LENGTH: 23
<212> TYPE: DNA
<213> ORGANISM: Artificial Sequence
<220> FEATURE:
<223> OTHER INFORMATION: Primer 2LTR fw

<400> SEQUENCE: 6
aactagggaa cccactgctt aag                                          23

<210> SEQ ID NO 7
<211> LENGTH: 23
<212> TYPE: DNA
<213> ORGANISM: Artificial Sequence
<220> FEATURE:
<223> OTHER INFORMATION: Primer 2LTR rv
```

```
<400> SEQUENCE: 7
gatcttgtct tcgttgggag tga                                        23

<210> SEQ ID NO 8
<211> LENGTH: 29
<212> TYPE: DNA
<213> ORGANISM: Artificial Sequence
<220> FEATURE:
<223> OTHER INFORMATION: Primer 2LTR probe
<220> FEATURE:
<221> NAME/KEY: misc_feature
<222> LOCATION: (1)..(1)
<223> OTHER INFORMATION: FAM reporter dye
<220> FEATURE:
<221> NAME/KEY: misc_feature
<222> LOCATION: (29)..(29)
<223> OTHER INFORMATION: TAMRA quencher dye

<400> SEQUENCE: 8
acactacttg aagcactcaa ggcaagctt                                  29

<210> SEQ ID NO 9
<211> LENGTH: 18
<212> TYPE: DNA
<213> ORGANISM: Artificial Sequence
<220> FEATURE:
<223> OTHER INFORMATION: Primer hTelo fw

<400> SEQUENCE: 9
ggcacacgtg gcttttcg                                              18

<210> SEQ ID NO 10
<211> LENGTH: 24
<212> TYPE: DNA
<213> ORGANISM: Artificial Sequence
<220> FEATURE:
<223> OTHER INFORMATION: Primer hTelo rev

<400> SEQUENCE: 10
ggtgaacctc gtaagtttat gcaa                                       24

<210> SEQ ID NO 11
<211> LENGTH: 24
<212> TYPE: DNA
<213> ORGANISM: Artificial Sequence
<220> FEATURE:
<223> OTHER INFORMATION: Primer hTelo probe

<400> SEQUENCE: 11
tcaggacgtc gagtggacac ggtg                                       24

<210> SEQ ID NO 12
<211> LENGTH: 8889
<212> TYPE: DNA
<213> ORGANISM: Artificial Sequence
<220> FEATURE:
<223> OTHER INFORMATION: pMDLg/pRRE complete vector sequence

<400> SEQUENCE: 12
ggatcccctg agggggcccc catgggctag aggatccggc ctcggcctct gcataaataa    60
aaaaaattag tcagccatga gcttggccca ttgcatacgt tgtatccata tcataatatg   120
tacatttata ttggctcatg tccaacatta ccgccatgtt gacattgatt attgactagt   180
tattaatagt aatcaattac ggggtcatta gttcatagcc catatatgga gttccgcgtt   240
acataactta cggtaaatgg cccgcctggc tgaccgccca acgacccccg cccattgacg   300
```

```
tcaataatga cgtatgttcc catagtaacg ccaataggga ctttccattg acgtcaatgg    360
gtggagtatt tacggtaaac tgcccacttg gcagtacatc aagtgtatca tatgccaagt    420 acgccccta ttgacgtcaa tgacggtaaa tggcccgcct ggcattatgc ccagtacatg    480
accttatggg actttcctac ttggcagtac atctacgtat tagtcatcgc tattaccatg    540
gtgatgcggt tttggcagta catcaatggg cgtggatagc ggtttgactc acggggattt    600
ccaagtctcc accccattga cgtcaatggg agtttgtttt ggcaccaaaa tcaacgggac    660
tttccaaaat gtcgtaacaa ctccgcccca ttgacgcaaa tgggcggtag cgtgtacgg    720 tgggaggtct atataagcag agctcgttta gtgaaccgtc agatcgcctg gagacgccat    780
ccacgctgtt ttgacctcca tagaagacac cgggaccgat ccagcctccc ctcgaagctt    840
acatgtggta ccgagctcgg atcctgagaa cttcagggtg agtctatggg acccttgatg    900
ttttctttcc ccttctttc tatggttaag ttcatgtcat aggaagggga gaagtaacag    960
ggtacacata ttgaccaaat cagggtaatt ttgcatttgt aattttaaaa aatgctttct   1020
tcttttaata tactttttg tttatcttat ttctaatact ttccctaatc tcttctttc   1080 agggcaataa tgatacaatg tatcatgcct ctttgcacca ttctaaagaa taacagtgat   1140
aatttctggg ttaaggcaat agcaatattt ctgcatataa atatttctgc atataaattg   1200
taactgatgt aagaggtttc atattgctaa tagcagctac aatccagcta ccattctgct   1260
tttattttat ggttgggata aggctggatt attctgagtc caagctaggc ccttttgcta   1320
atcatgttca tacctcttat cttcctccca cagctcctgg gcaacgtgct ggtctgtgtg   1380
ctggcccatc actttggcaa agcacgtgag atctgaattc gagatctgcc gccgccatgg   1440
gtgcgagagc gtcagtatta gcggggggag aattagatcg atgggaaaaa attcggttaa   1500
ggccaggggg aaagaaaaaa tataaattaa acatatagt atgggcaagc agggagctag   1560
aacgattcgc agttaatcct ggcctgttag aaacatcaga aggctgtaga caaatactgg   1620
gacagctaca accatccctt cagacaggat cagaagaact tagatcatta tataatacag   1680
tagcaaccct ctattgtgtg catcaaagga tagagataaa agacaccaag gaagctttag   1740
acaagataga ggaagagcaa aacaaaagta agaaaaaagc acagcaagca gcagctgaca   1800
caggacacag caatcaggtc agccaaaatt accctatagt gcagaacatc caggggcaaa   1860
tggtacatca ggccatatca cctagaactt taaatgcatg ggtaaaagta gtagaagaga   1920
aggctttcag cccagaagtg atacccatgt tttcagcatt atcagaagga gccaccccac   1980
aagatttaaa caccatgcta aacacagtgg ggggacatca agcagccatg caaatgttaa   2040 agagaccat caatgaggaa gctgcagaat gggatagagt gcatccagtg catgcagggc   2100
ctattgcacc aggccagatg agagaaccaa ggggaagtga catagcagga actactagta   2160
cccttcagga caaatagga tggatgacac ataatccacc tatcccagta ggagaaatct   2220
ataaaagatg gataatcctg ggattaaata aaatagtaag aatgtatagc cctaccagca   2280
ttctggacat aagacaagga ccaaaggaac cctttagaga ctatgtagac cgattctata   2340
aaactctaag agccgagcaa gcttcacaag aggtaaaaaa ttggatgaca gaaaccttgt   2400
tggtccaaaa tgcgaaccca gattgtaaga ctattttaaa agcattggga ccaggagcga   2460
cactagaaga aatgatgaca gcatgtcagg gagtgggggg acccggccat aaagcaagag   2520
ttttggctga agcaatgagc caagtaacaa atccagctac cataatgata cagaaaggca   2580
attttaggaa ccaaagaaag actgttaagt gtttcaattg tggcaaagaa gggcacatag   2640
```

```
ccaaaaattg cagggcccct aggaaaaagg gctgttggaa atgtggaaag gaaggacacc    2700
aaatgaaaga ttgtactgag agacaggcta atttttagg gaagatctgg ccttcccaca     2760
agggaaggcc agggaatttt cttcagagca gaccagagcc aacagcccca ccagaagaga    2820
gcttcaggtt tggggaagag acaacaactc cctctcagaa gcaggagccg atagacaagg    2880
aactgtatcc tttagcttcc ctcagatcac tctttggcag cgacccctcg tcacaataaa    2940 gataggggggg caattaaagg aagctctatt agatacagga gcagatgata cagtattaga   3000
agaaatgaat ttgccaggaa gatggaaacc aaaaatgata gggggaattg gaggttttat    3060
caaagtagga cagtatgatc agatactcat agaaatctgc ggacataaag ctataggtac    3120
agtattagta ggacctacac ctgtcaacat aattggaaga aatctgttga ctcagattgg    3180
ctgcacttta aattttccca ttagtcctat tgagactgta ccagtaaaat taaagccagg    3240
aatggatggc ccaaaagtta aacaatggcc attgacagaa gaaaaaataa aagcattagt    3300
agaaatttgt acagaaatgg aaaaggaagg aaaaatttca aaaattgggc ctgaaaatcc    3360
atacaatact ccagtatttg ccataaagaa aaaagacagt actaaatgga gaaaattagt    3420
agatttcaga gaacttaata agagaactca agatttctgg gaagttcaat taggaatacc    3480
acatcctgca gggttaaaac agaaaaaatc agtaacagta ctggatgtgg gcgatgcata    3540
tttttcagtt cccttagata aagacttcag gaagtatact gcatttacca tacctagtat    3600
aaacaatgag acaccaggga ttagatatca gtacaatgtg cttccacagg gatggaaagg    3660
atcaccagca atattccagt gtagcatgac aaaaatctta gagccttta gaaaacaaaa    3720 tccagacata gtcatctatc aatacatgga tgatttgtat gtaggatctg acttagaaat    3780
agggcagcat agaacaaaaa tagaggaact gagacaacat ctgttgaggt ggggatttac    3840
cacaccagac aaaaaacatc agaaagaacc tccattcctt tggatgggtt atgaactcca    3900
tcctgataaa tggacagtac agcctatagt gctgccagaa aaggacagct ggactgtcaa    3960
tgacatacag aaattagtgg gaaaattgaa ttgggcaagt cagatttatg cagggattaa    4020
agtaaggcaa ttatgtaaac ttcttagggg aaccaaagca ctaacagaag tagtaccact    4080
aacagaagaa gcagagctag aactggcaga aaacagggag attctaaaag aaccggtaca    4140
tggagtgtat tatgacccat caaaagactt aatagcagaa atacagaagc aggggcaagg    4200
ccaatggaca tatcaaattt atcaagagcc atttaaaaat ctgaaaacag gaaaatatgc    4260
aagaatgaag ggtgcccaca ctaatgatgt aaaacaatta acagaggcag tacaaaaaat    4320
agccacagaa agcatagtaa tatggggaaa gactcctaaa tttaaattac ccatacaaaa    4380
ggaaacatgg gaagcatggt ggacagagta ttggcaagcc acctggattc ctgagtggga    4440
gtttgtcaat acccctccct tagtgaagtt atggtaccag ttagagaaag aacccataat    4500
aggagcagaa actttctatg tagatggggc agccaatagg gaaactaaat taggaaaagc    4560
aggatatgta actgacagag gaagacaaaa agttgtcccc ctaacggaca caacaaatca    4620
gaagactgag ttacaagcaa ttcatctagc tttgcaggat tcgggattag aagtaaacat    4680
agtgacagac tcacaatatg cattgggaat cattcaagca caaccagata agagtgaatc    4740
agagttagtc agtcaaataa tagagcagtt aataaaaaag gaaaaagtct acctggcatg    4800
ggtaccagca cacaaaggaa ttggaggaaa tgaacaagta gatgggttgg tcagtgctgg    4860
aatcaggaaa gtactatttt tagatggaat agataaggcc caagaagaac atgagaaata    4920
tcacagtaat tggagagcaa tggctagtga ttttaaccta ccacctgtag tagcaaaaga    4980
aatagtagcc agctgtgata aatgtcagct aaaaggggaa gccatgcatg gacaagtaga    5040
```

```
ctgtagccca ggaatatggc agctagattg tacacattta gaaggaaaag ttatcttggt    5100
agcagttcat gtagccagtg gatatataga agcagaagta attccagcag agacagggca    5160
agaaacagca tacttcctct taaaattagc aggaagatgg ccagtaaaaa cagtacatac    5220
agacaatggc agcaatttca ccagtactac agttaaggcc gcctgttggt gggcggggat    5280
caagcaggaa tttggcattc cctacaatcc ccaaagtcaa ggagtaatag aatctatgaa    5340
taaagaatta agaaaatta taggacaggt aagagatcag gctgaacatc ttaagacagc    5400
agtacaaatg gcagtattca tccacaattt taaaagaaaa ggggggattg ggggtacag    5460 tgcaggggaa agaatagtag acataatagc aacagacata caaactaaag aattacaaaa    5520
acaaattaca aaaattcaaa attttcgggt ttattacagg gacagcagag atccagtttg    5580
gaaaggacca gcaaagctcc tctggaaagg tgaaggggca gtagtaatac aagataatag    5640
tgacataaaa gtagtgccaa gaagaaaagc aaagatcatc agggattatg gaaaacagat    5700
ggcaggtgat gattgtgtgg caagtagaca ggatgaggat taacacatgg aattccggag    5760
cggccgcagg agctttgttc cttgggttct tgggagcagc aggaagcact atgggcgcag    5820
cctcaatgac gctgacggta caggccagac aattattgtc tggtatagtg cagcagcaga    5880
acaatttgct gagggctatt gaggcgcaac agcatctgtt gcaactcaca gtctggggca    5940
tcaagcagct ccaggcaaga atcctggctg tggaaagata cctaaaggat caacagctcc    6000
tggggatttg gggttgctct ggaaaactca tttgcaccac tgctgtgcct tggaatgcta    6060
gttggagtaa taaatctctg aacagatttt ggaatcacac gacctggatg gagtgggaca    6120
gagaaattaa caattacaca agcttccgcg gaattcaccc caccagtgca ggctgcctat    6180
cagaaagtgg tggctggtgt ggctaatgcc ctggcccaca gtttcacta agctcgcttc    6240 cttgctgtcc aatttctatt aaaggttcct tggttcccta agtccaacta ctaaactggg    6300
ggatattatg aagggccttg agcatctgga ttctgcctaa taaaaaacat ttattttcat    6360
tgcaatgatg tatttaaatt atttctgaat attttactaa aaagggaatg tgggaggtca    6420
gtgcatttaa aacataaaga aatgaagagc tagttcaaac cttgggaaaa tacactatat    6480
cttaaactcc atgaaagaag gtgaggctgc aaacagctaa tgcacattgg caacagcccc    6540
gatgcctatg ccttattcat ccctcagaaa aggattcaag tagaggcttg atttggaggt    6600
taaagtttgg ctatgctgta ttttacatta cttattgttt tagctgtcct catgaatgtc    6660
ttttcactac ccatttgctt atcctgcatc tctcagcctt gactccactc agttctcttg    6720
cttagagata ccacctttcc cctgaagtgt tccttccatg ttttacggcg agatggtttc    6780
tcctcgcctg gccactcagc cttagttgtc tctgttgtct tatagaggtc tacttgaaga    6840
aggaaaaaca gggggcatgg tttgactgtc ctgtgagccc ttcttccctg cctccccac    6900 tcacagtgac ccggaatccc tcgacatggc agtctagcac tagtgcggcc gcagatctgc    6960
ttcctcgctc actgactcgc tgcgctcggt cgttcggctg cggcgagcgg tatcagctca    7020
ctcaaaggcg gtaatacggt tatccacaga atcagggat aacgcaggaa agaacatgtg    7080
agcaaaaggc cagcaaaagg ccaggaaccg taaaaaggcc gcgttgctgg cgttttccca    7140
taggctccgc cccctgacg agcatcacaa aaatcgacgc tcaagtcaga ggtggcgaaa    7200
cccgacagga ctataaagat accaggcgtt tccccctgga agctccctcg tgcgctctcc    7260
tgttccgacc ctgccgctta ccggatacct gtccgccttt ctcccttcgg gaagcgtggc    7320
gctttctcaa tgctcacgct gtaggtatct cagttcggtg taggtcgttc gctccaagct    7380
```

| | |
|---|---|
| gggctgtgtg cacgaacccc ccgttcagcc cgaccgctgc gccttatccg gtaactatcg | 7440 |
| tcttgagtcc aacccggtaa gacacgactt atcgccactg gcagcagcca ctggtaacag | 7500 |
| gattagcaga gcgaggtatg taggcggtgc tacagagttc ttgaagtggt ggcctaacta | 7560 |
| cggctacact agaaggacag tatttggtat ctgcgctctg ctgaagccag ttaccttcgg | 7620 |
| aaaaagagtt ggtagctctt gatccggcaa acaaaccacc gctggtagcg gtggtttttt | 7680 |
| tgtttgcaag cagcagatta cgcgcagaaa aaaggatct caagaagatc ctttgatctt | 7740 |
| ttctacgggg tctgacgctc agtggaacga aaactcacgt taagggattt tggtcatgag | 7800 |
| attatcaaaa aggatcttca cctagatcct tttaaattaa aaatgaagtt ttaaatcaat | 7860 |
| ctaaagtata tatgagtaaa cttggtctga cagttaccaa tgcttaatca gtgaggcacc | 7920 |
| tatctcagcg atctgtctat ttcgttcatc catagttgcc tgactccccg tcgtgtagat | 7980 |
| aactacgata cgggagggct taccatctgg ccccagtgct gcaatgatac cgcgagaccc | 8040 |
| acgctcaccg gctccagatt tatcagcaat aaaccagcca gccggaaggg ccgagcgcag | 8100 |
| aagtggtcct gcaactttat ccgcctccat ccagtctatt aattgttgcc gggaagctag | 8160 |
| agtaagtagt tcgccagtta atagtttgcg caacgttgtt gccattgcta caggcatcgt | 8220 |
| ggtgtcacgc tcgtcgtttg gtatggcttc attcagctcc ggttcccaac gatcaaggcg | 8280 |
| agttacatga tcccccatgt tgtgcaaaaa agcggttagc tccttcggtc ctccgatcgt | 8340 |
| tgtcagaagt aagttggccg cagtgttatc actcatggtt atggcagcac tgcataattc | 8400 |
| tcttactgtc atgccatccg taagatgctt ttctgtgact ggtgagtact caaccaagtc | 8460 |
| attctgagaa tagtgtatgc ggcgaccgag ttgctcttgc ccggcgtcaa tacgggataa | 8520 |
| taccgcgcca catagcagaa ctttaaaagt gctcatcatt ggaaaacgtt cttcggggcg | 8580 |
| aaaactctca aggatcttac cgctgttgag atccagttcg atgtaaccca ctcgtgcacc | 8640 |
| caactgatct tcagcatctt ttactttcac cagcgtttct gggtgagcaa aaacaggaag | 8700 |
| gcaaaatgcc gcaaaaaagg gaataagggc gacacggaaa tgttgaatac tcatactctt | 8760 |
| cctttttcaa tattattgaa gcatttatca gggttattgt ctcatgagcg gatacatatt | 8820 |
| tgaatgtatt tagaaaaata aacaataggg gttccgcgc acatttcccc gaaaagtgcc | 8880 |
| acctgacgt | 8889 |

<210> SEQ ID NO 13
<211> LENGTH: 1503
<212> TYPE: DNA
<213> ORGANISM: Artificial Sequence
<220> FEATURE:
<223> OTHER INFORMATION: Gag ORF from pMDLg/pRRE

<400> SEQUENCE: 13

| | |
|---|---|
| atgggtgcga gagcgtcagt attaagcggg ggagaattag atcgatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta gtgtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |

-continued

```
ccacaagatt taaacaccat gctaaacaca gtgggggggac atcaagcagc catgcaaatg      600
ttaaaagaga ccatcaatga ggaagctgca gaatgggata gagtgcatcc agtgcatgca      660
gggcctattg caccaggcca gatgagagaa ccaaggggaa gtgacatagc aggaactact      720
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt taaaagcatt gggaccagga     1020
gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaatttta ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga aagattgtac tgagagacag gctaattttt tagggaagat ctggccttcc     1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taa                                                                    1503
```

<210> SEQ ID NO 14
<211> LENGTH: 690
<212> TYPE: DNA
<213> ORGANISM: Artificial Sequence
<220> FEATURE:
<223> OTHER INFORMATION: Capsid (CA or p24) CDS from pMDLg/pRRE

<400> SEQUENCE: 14

```
cctatagtgc agaacatcca ggggcaaatg gtacatcagg ccatatcacc tagaacttta       60
aatgcatggg taaaagtagt agaagagaag gctttcagcc cagaagtgat acccatgttt      120
tcagcattat cagaaggagc cacccccacaa gatttaaaca ccatgctaaa cacagtgggg      180
ggacatcaag cagccatgca aatgttaaaa gagaccatca atgaggaagc tgcagaatgg      240
gatagagtgc atccagtgca tgcagggcct attgcaccag gccagatgag agaaccaagg      300
ggaagtgaca tagcaggaac tactagtacc cttcaggaac aaataggatg gatgacacat      360
aatccaccta tcccagtagg agaaatctat aaaagatgga taatcctggg attaaataaa      420
atagtaagaa tgtatagccc taccagcatt ctggacataa gacaaggacc aaaggaaccc      480
tttagagact atgtagaccg attctataaa actctaagag ccgagcaagc ttcacaagag      540
gtaaaaaatt ggatgacaga accttgttg gtccaaaatg cgaacccaga ttgtaagact      600
attttaaaag cattgggacc aggagcgaca ctagaagaaa tgatgacagc atgtcaggga      660
gtggggggac ccggccataa agcaagagtt                                        690
```

<210> SEQ ID NO 15
<211> LENGTH: 231
<212> TYPE: PRT
<213> ORGANISM: Artificial Sequence
<220> FEATURE:
<223> OTHER INFORMATION: Capsid (CA or p24) protein sequence encoded by
      pMDLg/pRRE
<220> FEATURE:
<221> NAME/KEY: misc_feature
<222> LOCATION: (231)..(231)
<223> OTHER INFORMATION: Xaa can be any naturally occurring amino acid

<400> SEQUENCE: 15

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr His Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Xaa
225                 230

<210> SEQ ID NO 16
<211> LENGTH: 500
<212> TYPE: PRT
<213> ORGANISM: Human immunodeficiency virus type 1

<400> SEQUENCE: 16

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

-continued

```
Lys Lys Ala Gln Gln Ala Ala Asp Thr Gly His Ser Ser Gln Val
            115                 120                 125
Ser Gln Asn Tyr Pro Ile Val Gln Asn Ile Gln Gly Gln Met Val His
    130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
        195                 200                 205
Ala Ala Glu Trp Asp Arg Val His Pro Val His Ala Gly Pro Ile Ala
    210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
        275                 280                 285
Pro Lys Glu Pro Phe Arg Asp Tyr Val Asp Arg Phe Tyr Lys Thr Leu
    290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
        355                 360                 365
Gln Val Thr Asn Ser Ala Thr Ile Met Met Gln Arg Gly Asn Phe Arg
    370                 375                 380
Asn Gln Arg Lys Ile Val Lys Cys Phe Asn Cys Gly Lys Glu Gly His
385                 390                 395                 400
Ile Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
        435                 440                 445
Leu Gln Ser Arg Pro Glu Pro Thr Ala Pro Glu Glu Ser Phe Arg
    450                 455                 460
Ser Gly Val Glu Thr Thr Thr Pro Ser Gln Lys Gln Glu Pro Ile Asp
465                 470                 475                 480
Lys Glu Leu Tyr Pro Leu Thr Ser Leu Arg Ser Leu Phe Gly Asn Asp
                485                 490                 495
Pro Ser Ser Gln
            500

<210> SEQ ID NO 17
<211> LENGTH: 231
<212> TYPE: PRT
```

<213> ORGANISM: Artificial Sequence
<220> FEATURE:
<223> OTHER INFORMATION: p24 sequence of the WT packaging construct (pMDL)
<220> FEATURE:
<221> NAME/KEY: misc_feature
<222> LOCATION: (231)..(231)
<223> OTHER INFORMATION: Xaa can be any naturally occurring amino acid

<400> SEQUENCE: 17

```
Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr His Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Xaa
225                 230
```

<210> SEQ ID NO 18
<211> LENGTH: 500
<212> TYPE: PRT
<213> ORGANISM: Human immunodeficiency virus type 1

<400> SEQUENCE: 18

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80
```

```
Thr Val Ala Thr Leu Tyr Cys Val His Gln Arg Ile Glu Ile Lys Asp
                85                  90                  95
Thr Lys Glu Ala Leu Asp Lys Ile Glu Glu Gln Asn Lys Ser Lys
            100                 105                 110
Lys Lys Ala Gln Gln Ala Ala Asp Thr Gly His Ser Asn Gln Val
        115                 120                 125
Ser Gln Asn Tyr Pro Ile Val Gln Asn Ile Gln Gly Gln Met Val His
130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
        195                 200                 205
Ala Ala Glu Trp Asp Arg Val His Pro Val His Ala Gly Pro Ile Ala
    210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
        275                 280                 285
Pro Lys Glu Pro Phe Arg Asp Tyr Val Asp Arg Phe Tyr Lys Thr Leu
290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
        355                 360                 365
Gln Val Thr Asn Ser Ala Thr Ile Met Met Gln Arg Gly Asn Phe Arg
    370                 375                 380
Asn Gln Arg Lys Ile Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
        435                 440                 445
Leu Gln Ser Arg Pro Glu Pro Thr Ala Pro Glu Glu Ser Phe Arg
    450                 455                 460
Ser Gly Val Glu Thr Thr Thr Pro Pro Gln Lys Gln Glu Pro Ile Asp
465                 470                 475                 480
Lys Glu Leu Tyr Pro Leu Thr Ser Leu Arg Ser Leu Phe Gly Asn Asp
                485                 490                 495
Pro Ser Ser Gln
```

<210> SEQ ID NO 19
<211> LENGTH: 501
<212> TYPE: PRT
<213> ORGANISM: Human immunodeficiency virus type 1

<400> SEQUENCE: 19

```
Ala Arg Ala Ser Val Leu Ser Gly Gly Glu Leu Asp Arg Trp Glu Lys
1               5                   10                  15

Ile Arg Leu Arg Pro Gly Gly Lys Lys Lys Tyr Arg Leu Lys His Ile
            20                  25                  30

Val Trp Ala Ser Arg Glu Leu Glu Arg Phe Ala Val Asn Pro Gly Leu
        35                  40                  45

Leu Glu Thr Ser Glu Gly Cys Arg Gln Ile Leu Gly Gln Leu Gln Pro
    50                  55                  60

Ser Leu Gln Thr Gly Ser Glu Glu Ile Arg Ser Leu Tyr Asn Thr Ile
65                  70                  75                  80

Ala Thr Leu Tyr Cys Val His Gln Lys Ile Glu Val Lys Asp Thr Lys
                85                  90                  95

Glu Ala Leu Asp Lys Ile Glu Glu Gln Asn Lys Ser Lys Lys Lys
            100                 105                 110

Ala Gln Gln Ala Ala Ala Asp Thr Gly Asn Ser Gly Gln Val Ser Gln
        115                 120                 125

Asn Phe Pro Ile Val Gln Asn Leu Gln Gly Gln Met Val His Gln Ala
130                 135                 140

Ile Ser Pro Arg Thr Leu Asn Ala Trp Val Lys Val Val Glu Glu Lys
145                 150                 155                 160

Ala Phe Ser Pro Glu Val Ile Pro Met Phe Ser Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Glu Thr Ile Asn Glu Glu Ala Ala
        195                 200                 205

Glu Trp Asp Arg Leu His Pro Val Gln Ala Gly Pro Val Ala Pro Gly
    210                 215                 220

Gln Ile Arg Asp Pro Arg Gly Ser Asp Ile Ala Gly Thr Thr Ser Thr
225                 230                 235                 240

Leu Gln Glu Gln Ile Gly Trp Met Thr Ser Asn Pro Pro Ile Pro Val
                245                 250                 255

Gly Glu Ile Tyr Lys Arg Trp Ile Ile Leu Gly Leu Asn Lys Ile Val
            260                 265                 270

Arg Met Tyr Ser Pro Thr Ser Ile Leu Asp Ile Arg Gln Gly Pro Lys
        275                 280                 285

Glu Pro Phe Arg Asp Tyr Val Asp Arg Phe Tyr Lys Thr Leu Arg Ala
    290                 295                 300

Glu Gln Ala Ser Gln Glu Val Lys Asn Trp Met Thr Glu Thr Leu Leu
305                 310                 315                 320

Val Gln Asn Ala Asn Pro Asp Cys Lys Thr Ile Leu Lys Ala Leu Gly
                325                 330                 335

Pro Ala Ala Thr Leu Glu Glu Met Met Thr Ala Cys Gln Gly Val Gly
            340                 345                 350

Gly Pro Ser His Lys Ala Arg Ile Leu Ala Glu Ala Met Ser Gln Val
        355                 360                 365
```

Thr Asn Ser Ala Thr Ile Met Met Gln Lys Gly Asn Phe Arg Asn Gln
    370                 375                 380

Arg Lys Ile Val Lys Cys Phe Asn Cys Gly Lys Glu Gly His Ile Ala
385                 390                 395                 400

Arg Asn Cys Arg Ala Pro Arg Lys Arg Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser His Lys Gly Arg Pro Gly Asn Phe Leu Gln
                435                 440                 445

Ser Arg Pro Glu Pro Thr Ala Pro Pro Ala Pro Pro Glu Glu Ser Phe
450                 455                 460

Arg Phe Gly Glu Glu Thr Thr Thr Pro Ser Gln Lys Gln Glu Leu Ile
465                 470                 475                 480

Asp Lys Glu Leu Tyr Pro Leu Ala Ser Leu Arg Ser Leu Phe Gly Asn
                485                 490                 495

Asp Pro Ser Ser Gln
            500

<210> SEQ ID NO 20
<211> LENGTH: 231
<212> TYPE: PRT
<213> ORGANISM: Artificial Sequence
<220> FEATURE:
<223> OTHER INFORMATION: Infectious molecular clone pNL4.3
<220> FEATURE:
<221> NAME/KEY: misc_feature
<222> LOCATION: (231)..(231)
<223> OTHER INFORMATION: Xaa can be any naturally occurring amino acid

<400> SEQUENCE: 20

Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr His Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Xaa
225                 230

<210> SEQ ID NO 21
<211> LENGTH: 690
<212> TYPE: DNA
<213> ORGANISM: Artificial Sequence
<220> FEATURE:
<223> OTHER INFORMATION: Capsid (CA or p24) nucleotide sequence

<400> SEQUENCE: 21

| | | | | | |
|---|---|---|---|---|---|
| cctatagtgc | agaacatcca | ggggcaaatg | gtacatcagg | ccatatcacc | tagaactttta | 60 |
| aatgcatggg | taaaagtagt | agaagagaag | gctttcagcc | cagaagtgat | acccatgttt | 120 |
| tcagcattat | cagaaggagc | caccccacaa | gatttaaaca | ccatgctaaa | cacagtgggg | 180 |
| ggacatcaag | cagccatgca | aatgttaaaa | gagaccatca | atgaggaagc | tgcagaatgg | 240 |
| gatagagtgc | atccagtgca | tgcagggcct | attgcaccag | gccagatgag | agaaccaagg | 300 |
| ggaagtgaca | tagcaggaac | tactagtacc | cttcaggaac | aaataggatg | gatgacacat | 360 |
| aatccaccta | tcccagtagg | agaaatctat | aaaagatgga | taatcctggg | attaaataaa | 420 |
| atagtaagaa | tgtatagccc | taccagcatt | ctggacataa | gacaaggacc | aaaggaaccc | 480 |
| tttagagact | atgtagaccg | attctataaa | actctaagag | ccgagcaagc | ttcacaagag | 540 |
| gtaaaaaatt | ggatgacaga | aaccttgttg | gtccaaaatg | cgaacccaga | ttgtaagact | 600 |
| attttaaaag | cattgggacc | aggagcgaca | ctagaagaaa | tgatgacagc | atgtcaggga | 660 |
| gtggggggac | ccggccataa | agcaagagtt | | | | 690 |

<210> SEQ ID NO 22
<211> LENGTH: 8889
<212> TYPE: DNA
<213> ORGANISM: Artificial Sequence
<220> FEATURE:
<223> OTHER INFORMATION: pMDLg/pRRE Gag-Pol-expressing packaging
      construct

<400> SEQUENCE: 22

| | | | | | |
|---|---|---|---|---|---|
| ggatccctg | aggggccccc | catgggctag | aggatccggc | tcggcctct | gcataaataa | 60 |
| aaaaaattag | tcagccatga | gcttggccca | ttgcatacgt | tgtatccata | tcataatatg | 120 |
| tacatttata | ttggctcatg | tccaacatta | ccgccatgtt | gacattgatt | attgactagt | 180 |
| tattaatagt | aatcaattac | ggggtcatta | gttcatagcc | catatatgga | gttccgcgtt | 240 |
| acataactta | cggtaaatgg | cccgcctggc | tgaccgccca | acgacccccg | cccattgacg | 300 |
| tcaataatga | cgtatgttcc | catagtaacg | ccaataggga | ctttccattg | acgtcaatgg | 360 |
| gtggagtatt | tacggtaaac | tgcccacttg | gcagtacatc | aagtgtatca | tatgccaagt | 420 |
| acgccccta | ttgacgtcaa | tgacggtaaa | tggcccgcct | ggcattatgc | ccagtacatg | 480 |
| accttatggg | actttcctac | ttggcagtac | atctacgtat | tagtcatcgc | tattaccatg | 540 |
| gtgatgcggt | tttggcagta | catcaatggg | cgtggatagc | ggtttgactc | acggggattt | 600 |
| ccaagtctcc | accccattga | cgtcaatggg | agtttgtttt | ggcaccaaaa | tcaacgggac | 660 |
| tttccaaaat | gtcgtaacaa | ctccgcccca | ttgacgcaaa | tgggcggtag | gcgtgtacgg | 720 |
| tgggaggtct | atataagcag | agctcgttta | gtgaaccgtc | agatcgcctg | gagacgccat | 780 |
| ccacgctgtt | ttgacctcca | tagaagacac | cgggaccgat | ccagcctccc | ctcgaagctt | 840 |

```
acatgtggta ccgagctcgg atcctgagaa cttcagggtg agtctatggg acccttgatg    900
ttttctttcc ccttcttttc tatggttaag ttcatgtcat aggaagggga gaagtaacag    960
ggtacacata ttgaccaaat cagggtaatt ttgcatttgt aattttaaaa aatgctttct   1020
tcttttaata tacttttttg tttatcttat ttctaatact ttccctaatc tctttctttc   1080
agggcaataa tgatacaatg tatcatgcct cttttgcacca ttctaaagaa taacagtgat   1140
aatttctggg ttaaggcaat agcaatattt ctgcatataa atatttctgc atataaattg   1200
taactgatgt aagaggtttc atattgctaa tagcagctac aatccagcta ccattctgct   1260
tttattttat ggttgggata aggctggatt attctgagtc caagctaggc ccttttgcta   1320
atcatgttca tacctcttat cttcctccca cagctcctgg gcaacgtgct ggtctgtgtg   1380
ctggcccatc actttggcaa agcacgtgag atctgaattc gagatctgcc gccgccatgg   1440
gtgcgagagc gtcagtatta agcggggggag aattagatcg atgggaaaaa attcggttaa   1500
ggccaggggg aaagaaaaaa tataaattaa aacatatagt atgggcaagc agggagctag   1560
aacgattcgc agttaatcct ggcctgttag aaacatcaga aggctgtaga caaatactgg   1620
gacagctaca accatcccct cagacaggat cagaagaact tagatcatta tataatacag   1680
tagcaaccct ctattgtgtg catcaaagga tagagataaa agacaccaag gaagctttag   1740
acaagataga ggaagagcaa aacaaaagta agaaaaaagc acagcaagca gcagctgaca   1800
caggacacag caatcaggtc agccaaaatt accctatagt gcagaacatc cagggggcaaa   1860 tggtacatca ggccatatca cctagaactt taaatgcatg ggtaaaagta gtagaagaga   1920
aggctttcag cccagaagtg atacccatgt tttcagcatt atcagaagga gccaccccac   1980
aagatttaaa caccatgcta aacacagtgg ggggacatca agcagccatg caaatgttaa   2040
aagagaccat caatgaggaa gctgcagaat gggatagagt gcatccagtg catacagggc   2100
ctattgcacc aggccagatg agagaaccaa ggggaagtga catagcagga actactagta   2160
cccttcagga acaaatagga tggatgacac ataatccacc tatcccagta ggagaaatct   2220
ataaaagatg gataatcctg ggattaaata aaatagtaag aatgtatagc cctaccagca   2280
ttctggacat aagacaagga ccaaaggaac ccttagaga ctatgtagac cgattctata   2340
aaactctaag agccgagcaa gcttcacaag aggtaaaaaa ttggatgaca gaaaccttgt   2400
tggtccaaaa tgcgaaccca gattgtaaga ctattttaaa agcattggga ccaggagcga   2460
cactagaaga aatgatgaca gcatgtcagg gagtgggggg acccggccat aaagcaagag   2520
ttttggctga agcaatgagc caagtaacaa atccagctac cataatgata cagaaaggca   2580
attttaggaa ccaaagaaag actgttaagt gtttcaattg tggcaaagaa gggcacatag   2640
ccaaaaattg cagggcccct aggaaaaagg gctgttggaa atgtggaaag gaaggacacc   2700
aaatgaaaga ttgtactgag agacaggcta attttttagg gaagatctgg ccttcccaca   2760
agggaaggcc agggaatttt cttcagagca gaccagagcc aacagcccca ccagaagaga   2820
gcttcaggtt tggggaagag acaacaactc cctctcagaa gcaggagccg atagacaagg   2880
aactgtatcc tttagcttcc ctcagatcac tctttggcag cgacccctcg tcacaataaa   2940 gataggggg caattaaagg aagctctatt agatacagga gcagatgata cagtattaga   3000
agaaatgaat ttgccaggaa gatggaaacc aaaaatgata ggggaattg gaggttttat   3060 caaagtagga cagtatgatc agatactcat agaaatctgc ggacataaag ctataggtac   3120
agtattagta ggacctacac ctgtcaacat aattggaaga aatctgttga ctcagattgg   3180
```

```
ctgcacttta aatttttccca ttagtcctat tgagactgta ccagtaaaat taaagccagg      3240
aatggatggc ccaaaagtta aacaatggcc attgacagaa gaaaaaataa aagcattagt      3300
agaaatttgt acagaaatgg aaaaggaagg aaaaatttca aaaattgggc ctgaaaatcc      3360
atacaatact ccagtatttg ccataaagaa aaaagacagt actaaatgga gaaaattagt      3420
agatttcaga gaacttaata agagaactca agatttctgg gaagttcaat taggaatacc      3480
acatcctgca gggttaaaac agaaaaaatc agtaacagta ctggatgtgg gcgatgcata      3540
tttttcagtt cccttagata aagacttcag gaagtatact gcatttacca tacctagtat      3600
aaacaatgag acaccaggga ttagatatca gtacaatgtg cttccacagg gatggaaagg      3660
atcaccagca atattccagt gtagcatgac aaaaatctta gagccttttta gaaaacaaaa      3720 tccagacata gtcatctatc aatacatgga tgatttgtat gtaggatctg acttagaaat      3780
agggcagcat agaacaaaaa tagaggaact gagacaacat ctgttgaggt ggggatttac      3840
cacaccagac aaaaaacatc agaaagaacc tccattcctt tggatgggtt atgaactcca      3900
tcctgataaa tggacagtac agcctatagt gctgccagaa aaggacagct ggactgtcaa      3960
tgacatacag aaattagtgg gaaaattgaa ttgggcaagt cagatttatg cagggattaa      4020
agtaaggcaa ttatgtaaac ttcttagggg aaccaaagca ctaacagaag tagtaccact      4080
aacagaagaa gcagagctag aactggcaga aaacagggag attctaaaag aaccggtaca      4140
tggagtgtat tatgacccat caaaagactt aatagcagaa atacagaagc aggggcaagg      4200
ccaatggaca tatcaaattt atcaagagcc atttaaaaat ctgaaaacag gaaaatatgc      4260
aagaatgaag ggtgcccaca ctaatgatgt gaaacaatta acagaggcag tacaaaaaat      4320
agccacagaa agcatagtaa tatggggaaa gactcctaaa tttaaattac ccatacaaaa      4380
ggaaacatgg gaagcatggt ggacagagta ttggcaagcc acctggattc ctgagtggga      4440
gtttgtcaat acccctccct tagtgaagtt atggtaccag ttagagaaag aacccataat      4500
aggagcagaa actttctatg tagatggggc agccaatagg gaaactaaat taggaaaagc      4560
aggatatgta actgacagag gaagacaaaa agttgtcccc ctaacggaca acaaaatca      4620 gaagactgag ttacaagcaa ttcatctagc tttgcaggat tcgggattag aagtaaacat      4680
agtgacagac tcacaatatg cattgggaat cattcaagca caaccagata agagtgaatc      4740
agagttagtc agtcaaataa tagagcagtt aataaaaaag gaaaagtct acctggcatg      4800 ggtaccagca cacaaaggaa ttggaggaaa tgaacaagta gatgggttgg tcagtgctgg      4860
aatcaggaaa gtactatttt tagatggaat agataaggcc caagaagaac atgagaaata      4920
tcacagtaat tggagagcaa tggctagtga ttttaaccta ccacctgtag tagcaaaaga      4980
aatagtagcc agctgtgata atgtcagct aaaaggggaa gccatgcatg gacaagtaga      5040
ctgtagccca ggaatatggc agctagattg tacacattta gaaggaaaag ttatcttggt      5100
agcagttcat gtagccagtg gatatataga agcagaagta attccagcag agacagggca      5160
agaaacagca tacttcctct taaaattagc aggaagatgg ccagtaaaaa cagtacatac      5220
agacaatggc agcaatttca ccagtactac agttaaggcc gcctgttggt gggcggggat      5280
caagcaggaa tttggcattc cctacaatcc ccaaagtcaa ggagtaatag aatctatgaa      5340
taaagaatta aagaaaatta taggacaggt aagagatcag gctgaacatc ttaagacagc      5400
agtacaaatg gcagtattca tccacaattt taaaagaaaa ggggggattg ggggtacag      5460 tgcagggaa agaatagtag acataatagc aacagacata caaactaaag aattacaaaa      5520
acaaattaca aaaattcaaa attttcgggt ttattacagg gacagcagag atccagtttg      5580
```

| | | | | | |
|---|---|---|---|---|---|
| gaaaggacca | gcaaagctcc | tctggaaagg | tgaaggggca | gtagtaatac | aagataatag | 5640 |
| tgacataaaa | gtagtgccaa | gaagaaaagc | aaagatcatc | agggattatg | gaaaacagat | 5700 |
| ggcaggtgat | gattgtgtgg | caagtagaca | ggatgaggat | taacacatgg | aattccggag | 5760 |
| cggccgcagg | agctttgttc | cttgggttct | tgggagcagc | aggaagcact | atgggcgcag | 5820 |
| cctcaatgac | gctgacggta | caggccagac | aattattgtc | tggtatagtg | cagcagcaga | 5880 |
| acaatttgct | gagggctatt | gaggcgcaac | agcatctgtt | gcaactcaca | gtctggggca | 5940 |
| tcaagcagct | ccaggcaaga | atcctggctg | tggaaagata | cctaaaggat | caacagctcc | 6000 |
| tggggatttg | gggttgctct | ggaaaactca | tttgcaccac | tgctgtgcct | tggaatgcta | 6060 |
| gttggagtaa | taaatctctg | aacagatttt | ggaatcacac | gacctggatg | gagtgggaca | 6120 |
| gagaaattaa | caattacaca | agcttccgcg | gaattcaccc | caccagtgca | ggctgcctat | 6180 |
| cagaaagtgg | tggctggtgt | ggctaatgcc | ctggcccaca | gtttcacta | agctcgcttc | 6240 |
| cttgctgtcc | aatttctatt | aaaggttcct | tggttcccta | agtccaacta | ctaaactggg | 6300 |
| ggatattatg | aagggccttg | agcatctgga | ttctgcctaa | taaaaaacat | ttattttcat | 6360 |
| tgcaatgatg | tatttaaatt | atttctgaat | attttactaa | aaagggaatg | tgggaggtca | 6420 |
| gtgcatttaa | aacataaaga | aatgaagagc | tagttcaaac | cttgggaaaa | tacactatat | 6480 |
| cttaaactcc | atgaaagaag | gtgaggctgc | aaacagctaa | tgcacattgg | caacagccct | 6540 |
| gatgcctatg | ccttattcat | ccctcagaaa | aggattcaag | tagaggcttg | atttggaggt | 6600 |
| taaagtttgg | ctatgctgta | ttttacatta | cttattgttt | tagctgtcct | catgaatgtc | 6660 |
| ttttcactac | ccatttgctt | atcctgcatc | tctcagcctt | gactccactc | agttctcttg | 6720 |
| cttagagata | ccacctttcc | cctgaagtgt | tccttccatg | ttttacggcg | agatggtttc | 6780 |
| tcctcgcctg | gccactcagc | cttagttgtc | tctgttgtct | tatagaggtc | tacttgaaga | 6840 |
| aggaaaaaca | gggggcatgg | tttgactgtc | ctgtgagccc | ttcttccctg | cctcccccac | 6900 |
| tcacagtgac | ccggaatccc | tcgacatggc | agtctagcac | tagtgcggcc | gcagatctgc | 6960 |
| ttcctcgctc | actgactcgc | tgcgctcggt | cgttcggctg | cggcgagcgg | tatcagctca | 7020 |
| ctcaaaggcg | gtaatacggt | tatccacaga | atcagggat | aacgcaggaa | agaacatgtg | 7080 |
| agcaaaaggc | cagcaaaagg | ccaggaaccg | taaaaaggcc | gcgttgctgg | cgttttttcca | 7140 |
| taggctccgc | cccctgacg | agcatcacaa | aaatcgacgc | tcaagtcaga | ggtggcgaaa | 7200 |
| cccgacagga | ctataaagat | accaggcgtt | tcccctgga | agctccctcg | tgcgctctcc | 7260 |
| tgttccgacc | ctgccgctta | ccggatacct | gtccgccttt | ctcccttcgg | gaagcgtggc | 7320 |
| gctttctcaa | tgctcacgct | gtaggtatct | cagttcggtg | taggtcgttc | gctccaagct | 7380 |
| gggctgtgtg | cacgaacccc | ccgttcagcc | cgaccgctgc | gccttatccg | gtaactatcg | 7440 |
| tcttgagtcc | aacccggtaa | gacacgactt | atcgccactg | gcagcagcca | ctggtaacag | 7500 |
| gattagcaga | gcgaggtatg | taggcggtgc | tacagagttc | ttgaagtggt | ggcctaacta | 7560 |
| cggctacact | agaaggacag | tatttggtat | ctgcgctctg | ctgaagccag | ttaccttcgg | 7620 |
| aaaaagagtt | ggtagctctt | gatccggcaa | acaaaccacc | gctggtagcg | gtggtttttt | 7680 |
| tgtttgcaag | cagcagatta | cgcgcagaaa | aaaggatct | caagaagatc | ctttgatctt | 7740 |
| ttctacgggg | tctgacgctc | agtggaacga | aaactcacgt | taagggattt | tggtcatgag | 7800 |
| attatcaaaa | aggatcttca | cctagatcct | tttaaattaa | aaatgaagtt | ttaaatcaat | 7860 |
| ctaaagtata | tatgagtaaa | cttggtctga | cagttaccaa | tgcttaatca | gtgaggcacc | 7920 |

| | |
|---|---:|
| tatctcagcg atctgtctat ttcgttcatc catagttgcc tgactccccg tcgtgtagat | 7980 |
| aactacgata cgggagggct taccatctgg ccccagtgct gcaatgatac cgcgagaccc | 8040 |
| acgctcaccg gctccagatt tatcagcaat aaaccagcca gccggaaggg ccgagcgcag | 8100 |
| aagtggtcct gcaactttat ccgcctccat ccagtctatt aattgttgcc gggaagctag | 8160 |
| agtaagtagt tcgccagtta atagtttgcg caacgttgtt gccattgcta caggcatcgt | 8220 |
| ggtgtcacgc tcgtcgtttg gtatggcttc attcagctcc ggttcccaac gatcaaggcg | 8280 |
| agttacatga tcccccatgt tgtgcaaaaa agcggttagc tccttcggtc ctccgatcgt | 8340 |
| tgtcagaagt aagttggccg cagtgttatc actcatggtt atggcagcac tgcataattc | 8400 |
| tcttactgtc atgccatccg taagatgctt ttctgtgact ggtgagtact caaccaagtc | 8460 |
| attctgagaa tagtgtatgc ggcgaccgag ttgctcttgc ccggcgtcaa tacgggataa | 8520 |
| taccgcgcca catagcagaa ctttaaaagt gctcatcatt ggaaaacgtt cttcggggcg | 8580 |
| aaaactctca aggatcttac cgctgttgag atccagttcg atgtaaccca ctcgtgcacc | 8640 |
| caactgatct tcagcatctt ttactttcac cagcgtttct gggtgagcaa aaacaggaag | 8700 |
| gcaaaatgcc gcaaaaaagg gaataagggc gacacggaaa tgttgaatac tcatactctt | 8760 |
| cctttttcaa tattattgaa gcatttatca gggttattgt ctcatgagcg gatacatatt | 8820 |
| tgaatgtatt tagaaaaata aacaaatagg ggttccgcgc acatttcccc gaaaagtgcc | 8880 |
| acctgacgt | 8889 |

<210> SEQ ID NO 23
<211> LENGTH: 8889
<212> TYPE: DNA
<213> ORGANISM: Artificial Sequence
<220> FEATURE:
<223> OTHER INFORMATION: pMDLg/pRRE Gag-Pol-expressing packaging construct

<400> SEQUENCE: 23

| | |
|---|---:|
| ggatcccctg agggggcccc catgggctag aggatccggc ctcggcctct gcataaataa | 60 |
| aaaaaattag tcagccatga gcttggccca ttgcatacgt tgtatccata tcataatatg | 120 |
| tacatttata ttggctcatg tccaacatta ccgccatgtt gacattgatt attgactagt | 180 |
| tattaatagt aatcaattac ggggtcatta gttcatagcc catatatgga gttccgcgtt | 240 |
| acataactta cggtaaatgg cccgcctggc tgaccgccca acgaccccccg cccattgacg | 300 |
| tcaataatga cgtatgttcc catagtaacg ccaatagggga ctttccattg acgtcaatgg | 360 |
| gtggagtatt tacggtaaac tgcccacttg gcagtacatc aagtgtatca tatgccaagt | 420 |
| acgccccta ttgacgtcaa tgacggtaaa tggcccgcct ggcattatgc ccagtacatg | 480 |
| accttatggg actttcctac ttggcagtac atctacgtat tagtcatcgc tattaccatg | 540 |
| gtgatgcggt tttggcagta catcaatggg cgtggatagc ggtttgactc acggggattt | 600 |
| ccaagtctcc accccattga cgtcaatggg agtttgtttt ggcaccaaaa tcaacgggac | 660 |
| tttccaaaat gtcgtaacaa ctccgcccca ttgacgcaaa tgggcggtag gcgtgtacgg | 720 |
| tgggaggtct atataagcag agctcgttta gtgaaccgtc agatcgcctg gagacgccat | 780 |
| ccacgctgtt ttgacctcca tagaagacac cgggaccgat ccagcctccc ctcgaagctt | 840 |
| acatgtggta ccgagctcgg atcctgagaa cttcagggtg agtctatggg acccttgatg | 900 |
| ttttctttcc cctttctttc tatggttaag ttcatgtcat aggaaggga gaagtaacag | 960 |
| ggtacacata ttgaccaaat cagggtaatt ttgcatttgt aattttaaaa aatgctttct | 1020 |

```
tcttttaata tacttttttg tttatcttat ttctaatact ttccctaatc tctttctttc    1080
agggcaataa tgatacaatg tatcatgcct ctttgcacca ttctaaagaa taacagtgat    1140
aatttctggg ttaaggcaat agcaatattt ctgcatataa atatttctgc atataaattg    1200
taactgatgt aagaggtttc atattgctaa tagcagctac aatccagcta ccattctgct    1260
tttattttat ggttgggata aggctggatt attctgagtc caagctaggc cctttgcta     1320 atcatgttca tacctcttat cttcctccca cagctcctgg caacgtgct ggtctgtgtg     1380 ctggcccatc actttggcaa agcacgtgag atctgaattc gagatctgcc gccgccatgg    1440
gtgcgagagc gtcagtatta agcgggggag aattagatcg atgggaaaaa attcggttaa    1500
ggccaggggg aaagaaaaaa tataaattaa acatatagt atgggcaagc agggagctag     1560
aacgattcgc agttaatcct ggcctgttag aaacatcaga aggctgtaga caaatactgg    1620
gacagctaca accatcccct cagacaggat cagaagaact tagatcatta tataatacag   1680
tagcaaccct ctattgtgtg catcaaagga tagagtaaa agacaccaag gaagctttag    1740
acaagataga ggaagagcaa aacaaaagta agaaaaaagc acagcaagca gcagctgaca   1800
caggacacag caatcaggtc agccaaaatt accctatagt gcagaacatc caggggcaaa   1860
tggtacatca ggccatatca cctagaactt taaatgcatg ggtaaaagta gtagaagaga   1920 aggcttttcag cccagaagtg atacccatgt tttcagcatt atcagaagga gccaccccac   1980
aagatttaaa caccatgcta aacacagtgg ggggacatca agcagccatg caaatgttaa   2040
aagagaccat caatgaggaa gctgcagaat gggatagagt gcatccagtg catgcagggc   2100
ctattgaacc aggccagatg agagaaccaa ggggaagtga catagcagga actactagta   2160
cccttcagga caaatagga tggatgacac ataatccacc tatcccagta ggagaaatct    2220
ataaaagatg gataatcctg ggattaaata aaatagtaag aatgtatagc cctaccagca   2280
ttctggacat aagacaagga ccaaaggaac cctttagaga ctatgtagac cgattctata   2340
aaactctaag agccgagcaa gcttcacaag aggtaaaaaa ttggatgaca gaaaccttgt   2400
tggtccaaaa tgcgaaccca gattgtaaga ctattttaaa agcattggga ccaggagcga   2460
cactagaaga aatgatgaca gcatgtcagg gagtgggggg acccggccat aaagcaagag   2520
ttttggctga agcaatgagc caagtaacaa atccagctac cataatgata cagaaaggca   2580
attttaggaa ccaaagaaag actgttaagt gtttcaattg tggcaaagaa gggcacatag   2640
ccaaaaattg cagggcccct aggaaaaagg gctgttggaa atgtggaaag gaaggacacc   2700
aaatgaaaga ttgtactgag agacaggcta attttttagg gaagatctgg ccttcccaca   2760
agggaaggcc agggaatttt cttcagagca gaccagagcc aacagcccca ccagaagaga   2820
gcttcaggtt tggggaagag acaacaactc cctctcagaa gcaggagccg atagacaagg   2880
aactgtatcc tttagcttcc ctcagatcac tctttggcag cgacccctcg tcacaataaa   2940
gatagggggg caattaaagg aagctctatt agatacagga gcagatgata cagtattaga   3000
agaaatgaat ttgccaggaa gatggaaacc aaaaatgata gggggaattg gaggttttat   3060
caaagtagga cagtatgatc agatactcat agaaatctgc ggacataaag ctataggtac   3120
agtattagta ggacctacac ctgtcaacat aattggaaga atctgttga ctcagattgg    3180 ctgcacttta aattttccca ttagtcctat tgagactgta ccagtaaaat taaagccagg   3240
aatggatggc ccaaaagtta acaatggcc attgacagaa gaaaaaataa agcattagt    3300 agaaatttgt acagaaatgg aaaaggaagg aaaaatttca aaaattgggc ctgaaaatcc   3360
atacaatact ccagtatttg ccataaagaa aaaagacagt actaaatgga gaaaattagt   3420
```

```
agatttcaga gaacttaata agagaactca agatttctgg gaagttcaat taggaatacc    3480
acatcctgca gggttaaaac agaaaaaatc agtaacagta ctggatgtgg gcgatgcata    3540
tttttcagtt cccttagata aagacttcag gaagtatact gcatttacca tacctagtat    3600
aaacaatgag acaccaggga ttagatatca gtacaatgtg cttccacagg gatggaaagg    3660
atcaccagca atattccagt gtagcatgac aaaaatctta gagccttttta gaaaacaaaa    3720
tccagacata gtcatctatc aatacatgga tgatttgtat gtaggatctg acttagaaat    3780
agggcagcat agaacaaaaa tagaggaact gagacaacat ctgttgaggt ggggatttac    3840
cacaccagac aaaaaacatc agaaagaacc tccattcctt tggatgggtt atgaactcca    3900
tcctgataaa tggacagtac agcctatagt gctgccagaa aaggacagct ggactgtcaa    3960
tgacatacag aaattagtgg gaaaattgaa ttgggcaagt cagatttatg cagggattaa    4020
agtaaggcaa ttatgtaaac ttcttagggg aaccaaagca ctaacagaag tagtaccact    4080
aacagaagaa gcagagctag aactggcaga aaacagggag attctaaaag aaccggtaca    4140
tggagtgtat tatgacccat caaaagactt aatagcagaa atacagaagc aggggcaagg    4200
ccaatggaca tatcaaattt atcaagagcc atttaaaaat ctgaaaacag gaaaatatgc    4260
aagaatgaag ggtgcccaca ctaatgatgt gaaacaatta acagaggcag tacaaaaaat    4320
agccacagaa agcatagtaa tatggggaaa gactcctaaa tttaaattac ccatacaaaa    4380
ggaaacatgg gaagcatggt ggacagagta ttggcaagcc acctggattc ctgagtggga    4440
gtttgtcaat acccctccct tagtgaagtt atggtaccag ttagaaaag aacccataat    4500
aggagcagaa actttctatg tagatggggc agccaatagg gaaactaaat taggaaaagc    4560
aggatatgta actgacagag gaagacaaaa agttgtcccc ctaacggaca caacaaatca    4620
gaagactgag ttacaagcaa ttcatctagc tttgcaggat tcgggattag aagtaaacat    4680
agtgacagac tcacaatatg cattgggaat cattcaagca caaccagata gagtgaatc    4740
agagttagtc agtcaaataa tagagcagtt aataaaaaag gaaaaagtct acctggcatg    4800
ggtaccagca cacaaaggaa ttggaggaaa tgaacaagta gatgggttgg tcagtgctgg    4860
aatcaggaaa gtactatttt tagatggaat agataaggcc caagaagaac atgagaaata    4920
tcacagtaat tggagagcaa tggctagtga ttttaaccta ccacctgtag tagcaaaaga    4980
aatagtagcc agctgtgata atgtcagct aaaagggaa gccatgcatg gacaagtaga    5040
ctgtagccca ggaatatggc agctagattg tacacattta gaaggaaaag ttatcttggt    5100
agcagttcat gtagccagtg gatatataga agcagaagta attccagcag agacagggca    5160
agaaacagca tacttcctct taaaattagc aggaagatgg ccagtaaaaa cagtacatac    5220
agacaatggc agcaatttca ccagtactac agttaaggcc gcctgttggt gggcggggat    5280
caagcaggaa tttggcattc cctacaatcc ccaaagtcaa ggagtaatag aatctatgaa    5340
taaagaatta aagaaaatta taggacaggt aagagatcag gctgaacatc ttaagacagc    5400
agtacaaatg gcagtattca tccacaattt taaaagaaaa ggggggattg ggggtacag    5460
tgcaggggaa agaatagtag acataatagc aacagacata caaactaaag aattacaaaa    5520
acaaattaca aaaattcaaa attttcgggt ttattacagg gacagcagag atccagtttg    5580
gaaaggacca gcaaagctcc tctggaaagg tgaagggca gtagtaatac aagataatag    5640
tgacataaaa gtagtgccaa gaagaaaagc aaagatcatc agggattatg gaaaacagat    5700
ggcaggtgat gattgtgtgg caagtagaca ggatgaggat taacacatgg aattccggag    5760
```

```
cggccgcagg agctttgttc cttgggttct tgggagcagc aggaagcact atgggcgcag    5820
cctcaatgac gctgacggta caggccagac aattattgtc tggtatagtg cagcagcaga    5880
acaatttgct gagggctatt gaggcgcaac agcatctgtt gcaactcaca gtctggggca    5940
tcaagcagct ccaggcaaga atcctggctg tggaaagata cctaaaggat caacagctcc    6000
tggggatttg gggttgctct ggaaaactca tttgcaccac tgctgtgcct tggaatgcta    6060
gttggagtaa taaatctctg aacagatttg gaatcacac gacctggatg gagtgggaca    6120
gagaaattaa caattacaca agcttccgcg gaattcaccc caccagtgca ggctgcctat    6180
cagaaagtgg tggctggtgt ggctaatgcc ctggcccaca gtttcacta agctcgcttc    6240 cttgctgtcc aatttctatt aaaggttcct tggttcccta agtccaacta ctaaactggg    6300
ggatattatg aagggccttg agcatctgga ttctgcctaa taaaaaacat ttattttcat    6360
tgcaatgatg tatttaaatt atttctgaat attttactaa aaagggaatg tgggaggtca    6420
gtgcatttaa aacataaaga aatgaagagc tagttcaaac cttgggaaaa tacactatat    6480
cttaaactcc atgaaagaag gtgaggctgc aaacagctaa tgcacattgg caacagccct    6540
gatgcctatg ccttattcat ccctcagaaa aggattcaag tagaggcttg atttggaggt    6600
taaagtttgg ctatgctgta ttttacatta cttattgttt tagctgtcct catgaatgtc    6660
ttttcactac ccatttgctt atcctgcatc tctcagcctt gactccactc agttctcttg    6720
cttagagata ccacctttcc cctgaagtgt tccttccatg ttttacggcg agatggtttc    6780
tcctcgcctg gccactcagc cttagttgtc tctgttgtct tatagaggtc tacttgaaga    6840
aggaaaaaca gggggcatgg tttgactgtc ctgtgagccc ttcttccctg cctcccccac    6900
tcacagtgac ccggaatccc tcgacatggc agtctagcac tagtgcggcc gcagatctgc    6960
ttcctcgctc actgactcgc tgcgctcggt cgttcggctg cggcgagcgg tatcagctca    7020
ctcaaaggcg gtaatacggt tatccacaga atcagggat aacgcaggaa agaacatgtg    7080
agcaaaaggc cagcaaaagg ccaggaaccg taaaaaggcc gcgttgctgg cgttttccca    7140
taggctccgc cccctgacg agcatcacaa aaatcgacgc tcaagtcaga ggtggcgaaa    7200
cccgacagga ctataaagat accaggcgtt tcccctgga agctccctcg tgcgctctcc    7260
tgttccgacc ctgccgctta ccggatacct gtccgccttt ctcccttcgg gaagcgtggc    7320
gctttctcaa tgctcacgct gtaggtatct cagttcggtg taggtcgttc gctccaagct    7380
gggctgtgtg cacgaacccc ccgttcagcc cgaccgctgc gccttatccg gtaactatcg    7440
tcttgagtcc aacccggtaa gacacgactt atcgccactg gcagcagcca ctggtaacag    7500
gattagcaga gcgaggtatg taggcggtgc tacagagttc ttgaagtggt ggcctaacta    7560
cggctacact agaaggacag tatttggtat ctgcgctctg ctgaagccag ttaccttcgg    7620
aaaaagagtt ggtagctctt gatccggcaa acaaaccacc gctggtagcg tggttttttt    7680
tgtttgcaag cagcagatta cgcgcagaaa aaaaggatct caagaagatc ctttgatctt    7740
ttctacgggg tctgacgctc agtggaacga aaactcacgt taagggattt tggtcatgag    7800
attatcaaaa aggatcttca cctagatcct tttaaattaa aaatgaagtt ttaaatcaat    7860
ctaaagtata tatgagtaaa cttggtctga cagttaccaa tgcttaatca gtgaggcacc    7920
tatctcagcg atctgtctat ttcgttcatc catagttgcc tgactccccg tcgtgtagat    7980
aactacgata cgggagggct taccatctgg ccccagtgct gcaatgatac cgcgagaccc    8040
acgctcaccg gctccagatt tatcagcaat aaaccagcca gccggaaggg ccgagcgcag    8100
aagtggtcct gcaactttat ccgcctccat ccagtctatt aattgttgcc gggaagctag    8160
```

```
agtaagtagt tcgccagtta atagtttgcg caacgttgtt gccattgcta caggcatcgt    8220
ggtgtcacgc tcgtcgtttg gtatggcttc attcagctcc ggttcccaac gatcaaggcg    8280
agttacatga tcccccatgt tgtgcaaaaa agcggttagc tccttcggtc ctccgatcgt    8340
tgtcagaagt aagttggccg cagtgttatc actcatggtt atggcagcac tgcataattc    8400
tcttactgtc atgccatccg taagatgctt ttctgtgact ggtgagtact caaccaagtc    8460
attctgagaa tagtgtatgc ggcgaccgag ttgctcttgc ccggcgtcaa tacgggataa    8520
taccgcgcca catagcagaa ctttaaaagt gctcatcatt ggaaaacgtt cttcggggcg    8580
aaaactctca aggatcttac cgctgttgag atccagttcg atgtaaccca ctcgtgcacc    8640
caactgatct tcagcatctt ttactttcac cagcgtttct gggtgagcaa aacaggaag    8700 gcaaaatgcc gcaaaaaagg gaataagggc gacacggaaa tgttgaatac tcatactctt    8760 ccttttttcaa tattattgaa gcatttatca gggttattgt ctcatgagcg gatacatatt    8820
tgaatgtatt tagaaaaata aacaataggg gttccgcgc acatttcccc gaaaagtgcc    8880
acctgacgt                                                             8889
```

<210> SEQ ID NO 24
<211> LENGTH: 8889
<212> TYPE: DNA
<213> ORGANISM: Artificial Sequence
<220> FEATURE:
<223> OTHER INFORMATION: pMDLg/pRRE Gag-Pol-expressing packaging
      construct

<400> SEQUENCE: 24

```
ggatcccctg aggggccccc catgggctag aggatccggc ctcggcctct gcataaataa      60
aaaaaattag tcagccatga gcttggccca ttgcatacgt tgtatccata tcataatatg     120
tacatttata ttggctcatg tccaacatta ccgccatgtt gacattgatt attgactagt     180
tattaatagt aatcaattac ggggtcatta gttcatagcc catatatgga gttccgcgtt     240
acataactta cggtaaatgg cccgcctggc tgaccgccca acgacccccg cccattgacg     300
tcaataatga cgtatgttcc catagtaacg ccaatagga cttccattg acgtcaatgg     360 gtggagtatt tacggtaaac tgcccacttg gcagtacatc aagtgtatca tatgccaagt     420 acgccccta ttgacgtcaa tgacggtaaa tggcccgcct ggcattatgc ccagtacatg     480
accttatggg actttcctac ttggcagtac atctacgtat tagtcatcgc tattaccatg     540
gtgatgcggt tttggcagta catcaatggg cgtggatagc ggtttgactc acggggattt     600
ccaagtctcc accccattga cgtcaatggg agtttgtttt ggcaccaaaa tcaacgggac     660
tttccaaaat gtcgtaacaa ctccgcccca ttgacgcaaa tgggcggtag gcgtgtacgg     720
tgggaggtct atataagcag agctcgttta gtgaaccgtc agatcgcctg gagacgccat     780
ccacgctgtt ttgacctcca tagaagacac cgggaccgat ccagcctccc ctcgaagctt     840
acatgtggta ccgagctcgg atcctgagaa cttcaggg tg agtctatggg acccttgatg     900
ttttctttcc ccttcttttc tatggttaag ttcatgtcat aggaagggga gaagtaacag     960
ggtacacata ttgaccaaat cagggtaatt ttgcatttgt aattttaaaa aatgcttttct    1020 tctttaata tactttttg tttatcttat ttctaatact ttccctaatc tctttctttc     1080
agggcaataa tgatacaatg tatcatgcct ctttgcacca ttctaaagaa taacagtgat    1140
aatttctggg ttaaggcaat agcaatattt ctgcatataa atatttctgc atataaattg    1200
taactgatgt aagaggtttc atattgctaa tagcagctac aatccagcta ccattctgct    1260
```

```
tttattttat ggttgggata aggctggatt attctgagtc caagctaggc ccttttgcta   1320
atcatgttca tacctcttat cttcctccca cagctcctgg gcaacgtgct ggtctgtgtg   1380
ctggcccatc actttggcaa agcacgtgag atctgaattc gagatctgcc gccgccatgg   1440
gtgcgagagc gtcagtatta agcgggggag aattagatcg atgggaaaaa attcggttaa   1500
ggccaggggg aaagaaaaaa tataaattaa acatatagt atgggcaagc agggagctag    1560
aacgattcgc agttaatcct ggcctgttag aaacatcaga aggctgtaga caaatactgg   1620
gacagctaca accatccctt cagacaggat cagaagaact tagatcatta tataatacag   1680
tagcaaccct ctattgtgtg catcaaagga tagagataaa agacaccaag gaagctttag   1740
acaagataga ggaagagcaa aacaaaagta agaaaaaagc acagcaagca gcagctgaca   1800
caggacacag caatcaggtc agccaaaatt accctatagt gcagaacatc caggggcaaa   1860
tggtacatca ggccatatca cctagaactt taaatgcatg ggtaaaagta gtagaagaga   1920
aggctttcag cccagaagtg atacccatgt tttcagcatt atcagaagga gccaccccac   1980
aagatttaaa caccatgcta aacacagtgg ggggacatca agcagccatg caaatgttaa   2040
aagagaccat caatgaggaa gctgcagaat gggatagagt gcatccagtg catcagggc    2100 ctattgaacc aggccagatg agagaaccaa ggggaagtga catagcagga actactagta   2160
cccttcagga caaatagga tggatgacac ataatccacc tatcccagta ggagaaatct    2220
ataaaagatg gataatcctg ggattaaata aaatagtaag aatgtatagc cctaccagca   2280
ttctggacat aagacaagga ccaaaggaac cctttagaga ctatgtagac cgattctata   2340
aaactctaag agccgagcaa gcttcacaag aggtaaaaaa ttggatgaca gaaaccttgt   2400
tggtccaaaa tgcgaaccca gattgtaaga ctattttaaa agcattggga ccaggagcga   2460
cactagaaga aatgatgaca gcatgtcagg gagtgggggg acccggccat aaagcaagag   2520
ttttggctga agcaatgagc caagtaacaa atccagctac cataatgata cagaaaggca   2580
attttaggaa ccaaagaaag actgttaagt gtttcaattg tggcaaagaa gggcacatag   2640
ccaaaaattg cagggcccct aggaaaaagg gctgttggaa atgtggaaag gaaggacacc   2700
aaatgaaaga ttgtactgag agacaggcta attttttagg gaagatctgg ccttcccaca   2760
agggaaggcc agggaatttt cttcagagca gaccagagcc aacagcccca ccagaagaga   2820
gcttcaggtt tggggaagag acaacaactc cctctcagaa gcaggagccg atagacaagg   2880
aactgtatcc tttagcttcc ctcagatcac tctttggcag cgaccnctcg tcacaataaa   2940
gatagggggg caattaaagg aagctctatt agatacagga gcagatgata cagtattaga   3000
agaaatgaat ttgccaggaa gatggaaacc aaaaatgata gggggaattg gaggttttat   3060
caaagtagga cagtatgatc agatactcat agaaatctgc ggacataaag ctataggtac   3120
agtattagta ggacctacac ctgtcaacat aattggaaga atctgttga ctcagattgg    3180 ctgcacttta aattttccca ttagtcctat tgagactgta ccagtaaaat taaagccagg   3240
aatggatggc ccaaaagtta acaatggcc attgacagaa gaaaaaataa aagcattagt    3300
agaaatttgt acagaaatgg aaaggaagg aaaaatttca aaaattgggc ctgaaaatcc    3360
atacaatact ccagtatttg ccataaagaa aaaagacagt actaaatgga gaaaattagt   3420
agatttcaga gaacttaata agagaactca agatttctgg gaagttcaat taggaatacc   3480
acatcctgca gggttaaaac agaaaaaatc agtaacagta ctggatgtgg gcgatgcata   3540
tttttcagtt cccttagata aagacttcag gaagtatact gcatttacca tacctagtat   3600
```

```
aaacaatgag acaccaggga ttagatatca gtacaatgtg cttccacagg gatggaaagg    3660
atcaccagca atattccagt gtagcatgac aaaaatctta gagcctttta gaaaacaaaa    3720
tccagacata gtcatctatc aatacatgga tgatttgtat gtaggatctg acttagaaat    3780
agggcagcat agaacaaaaa tagaggaact gagacaacat ctgttgaggt ggggatttac    3840
cacaccagac aaaaacatc agaaagaacc tccattcctt tggatgggtt atgaactcca     3900
tcctgataaa tggacagtac agcctatagt gctgccagaa aaggacagct ggactgtcaa    3960
tgacatacag aaattagtgg gaaaattgaa ttgggcaagt cagatttatg cagggattaa    4020
agtaaggcaa ttatgtaaac ttcttagggg aaccaaagca ctaacagaag tagtaccact    4080
aacagaagaa gcagagctag aactggcaga aaacagggag attctaaaag aaccggtaca    4140
tggagtgtat tatgacccat caaaagactt aatagcagaa atacagaagc aggggcaagg    4200
ccaatggaca tatcaaattt atcaagagcc atttaaaaat ctgaaaacag gaaaatatgc    4260
aagaatgaag ggtgcccaca ctaatgatgt gaaacaatta acagaggcag tacaaaaaat    4320
agccacagaa agcatagtaa tatggggaaa gactcctaaa tttaaattac ccatacaaaa    4380
ggaaacatgg gaagcatggt ggacagagta ttggcaagcc acctggattc ctgagtggga    4440
gtttgtcaat acccctccct tagtgaagtt atggtaccag ttagagaaag aacccataat    4500
aggagcagaa actttctatg tagatggggc agccaatagg gaaactaaat taggaaaagc    4560
aggatatgta actgacagag gaagacaaaa agttgtcccc ctaacggaca caacaaatca    4620
gaagactgag ttacaagcaa ttcatctagc tttgcaggat tcgggattag aagtaaacat    4680
agtgacagac tcacaatatg cattgggaat cattcaagca caaccagata agagtgaatc    4740
agagttagtc agtcaaataa tagagcagtt aataaaaaag gaaaaagtct acctggcatg    4800
ggtaccagca cacaaaggaa ttggaggaaa tgaacaagta gatgggttgg tcagtgctgg    4860
aatcaggaaa gtactatttt tagatggaat agataaggcc caagaagaac atgagaaata    4920
tcacagtaat tggagagcaa tggctagtga ttttaaccta ccacctgtag tagcaaaaga    4980
aatagtagcc agctgtgata atgtcagcta aaaggggaa gccatgcatg gacaagtaga    5040
ctgtagccca ggaatatggc agctagattg tacacattta gaaggaaaag ttatcttggt    5100
agcagttcat gtagccagtg gatatataga agcagaagta attccagcag agacagggca    5160
agaaacagca tacttcctct taaaattagc aggaagatgg ccagtaaaaa cagtacatac    5220
agacaatggc agcaatttca ccagtactac agttaaggcc gcctgttggt gggcggggat    5280
caagcaggaa tttggcattc cctacaatcc ccaaagtcaa ggagtaatag aatctatgaa    5340
taaagaatta aagaaaatta taggacaggt aagagatcag gctgaacatc ttaagacagc    5400
agtacaaatg gcagtattca tccacaattt taaaagaaaa ggggggattg ggggtacag    5460 tgcagggaa agaatagtag acataatagc aacagacata caaactaaag aattacaaaa    5520
acaaattaca aaaattcaaa attttcgggt ttattacagg gacagcagag atccagtttg    5580
gaaaggacca gcaaagctcc tctggaaagg tgaaggggca gtagtaatac aagataatag    5640
tgacataaaa gtagtgccaa gaagaaaagc aaagatcatc agggattatg gaaaacagat    5700
ggcaggtgat gattgtgtgg caagtagaca ggatgaggat taacacatgg aattccggag    5760
cggccgcagg agctttgttc cttgggttct tgggagcagc aggaagcact atgggcgcag    5820
cctcaatgac gctgacggta caggccagac aattattgtc tggtatagtg cagcagcaga    5880
acaatttgct gagggctatt gaggcgcaac agcatctgtt gcaactcaca gtctgggca     5940 tcaagcagct ccaggcaaga atcctggctg tggaaagata cctaaaggat caacagctcc    6000
```

```
tggggatttg gggttgctct ggaaaactca tttgcaccac tgctgtgcct tggaatgcta   6060
gttggagtaa taaatctctg aacagattt ggaatcacac gacctggatg gagtgggaca    6120
gagaaattaa caattacaca agcttccgcg gaattcaccc caccagtgca ggctgcctat   6180
cagaaagtgg tggctggtgt ggctaatgcc ctggcccaca gtttcacta agctcgcttc    6240 cttgctgtcc aatttctatt aaaggttcct tggttcccta agtccaacta ctaaactggg   6300
ggatattatg aagggccttg agcatctgga ttctgcctaa taaaaaacat ttattttcat   6360
tgcaatgatg tatttaaatt atttctgaat attttactaa aaagggaatg tgggaggtca   6420
gtgcatttaa aacataaaga aatgaagagc tagttcaaac cttgggaaaa tacactatat   6480
cttaaactcc atgaaagaag gtgaggctgc aaacagctaa tgcacattgg caacagccct   6540
gatgcctatg ccttattcat ccctcagaaa aggattcaag tagaggcttg atttggaggt   6600
taaagtttgg ctatgctgta ttttacatta cttattgttt tagctgtcct catgaatgtc   6660
ttttcactac ccatttgctt atcctgcatc tctcagcctt gactccactc agttctcttg   6720
cttagagata ccacctttcc cctgaagtgt tccttccatg ttttacggcg agatggtttc   6780
tcctcgcctg gccactcagc cttagttgtc tctgttgtct tatagaggtc tacttgaaga   6840
aggaaaaaca gggggcatgg tttgactgtc ctgtgagccc ttcttccctg cctcccccac   6900
tcacagtgac ccggaatccc tcgacatggc agtctagcac tagtgcggcc gcagatctgc   6960
ttcctcgctc actgactcgc tgcgctcggt cgttcggctg cggcgagcgg tatcagctca   7020
ctcaaaggcg gtaatacggt tatccacaga atcaggggat aacgcaggaa agaacatgtg   7080
agcaaaaggc cagcaaaagg ccaggaaccg taaaaaggcc gcgttgctgg cgttttttcca   7140 taggctccgc cccctgacg agcatcacaa aaatcgacgc tcaagtcaga ggtggcgaaa    7200
cccgacagga ctataaagat accaggcgtt tccccctgga agctccctcg tgcgctctcc   7260
tgttccgacc ctgccgctta ccggatacct gtccgccttt ctcccttcgg gaagcgtggc   7320
gctttctcaa tgctcacgct gtaggtatct cagttcggtg taggtcgttc gctccaagct   7380
gggctgtgtg cacgaacccc ccgttcagcc cgaccgctgc gccttatccg gtaactatcg   7440
tcttgagtcc aacccggtaa gacacgactt atcgccactg gcagcagcca ctggtaacag   7500
gattagcaga gcgaggtatg taggcggtgc tacagagttc ttgaagtggt ggcctaacta   7560
cggctacact agaaggacag tatttggtat ctgcgctctg ctgaagccag ttaccttcgg   7620
aaaaagagtt ggtagctctt gatccggcaa acaaaccacc gctggtagcg gtggttttt    7680 tgtttgcaag cagcagatta cgcgcagaaa aaaaggatct caagaagatc ctttgatctt   7740
ttctacgggg tctgacgctc agtggaacga aaactcacgt taagggattt tggtcatgag   7800
attatcaaaa aggatcttca cctagatcct tttaaattaa aaatgaagtt ttaaatcaat   7860
ctaaagtata tatgagtaaa cttggtctga cagttaccaa tgcttaatca gtgaggcacc   7920
tatctcagcg atctgtctat ttcgttcatc catagttgcc tgactccccg tcgtgtagat   7980
aactacgata cgggagggct taccatctgg ccccagtgct gcaatgatac cgcgagaccc   8040
acgctcaccg gctccagatt tatcagcaat aaaccagcca gccggaaggg ccgagcgcag   8100
aagtggtcct gcaactttat ccgcctccat ccagtctatt aattgttgcc gggaagctag   8160
agtaagtagt tcgccagtta atagtttgcg caacgttgtt gccattgcta caggcatcgt   8220
ggtgtcacgc tcgtcgtttg gtatggcttc attcagctcc ggttcccaac gatcaaggcg   8280
agttacatga tcccccatgt tgtgcaaaaa agcggttagc tccttcggtc ctccgatcgt   8340
```

```
tgtcagaagt aagttggccg cagtgttatc actcatggtt atggcagcac tgcataattc    8400
tcttactgtc atgccatccg taagatgctt ttctgtgact ggtgagtact caaccaagtc    8460
attctgagaa tagtgtatgc ggcgaccgag ttgctcttgc ccggcgtcaa tacgggataa    8520
taccgcgcca catagcagaa ctttaaaagt gctcatcatt ggaaaacgtt cttcggggcg    8580
aaaactctca aggatcttac cgctgttgag atccagttcg atgtaaccca ctcgtgcacc    8640
caactgatct tcagcatctt ttactttcac cagcgtttct gggtgagcaa aaacaggaag    8700
gcaaaatgcc gcaaaaaagg gaataagggc gacacggaaa tgttgaatac tcatactctt    8760
cctttttcaa tattattgaa gcatttatca gggttattgt ctcatgagcg gatacatatt    8820
tgaatgtatt tagaaaaata aacaaatagg ggttccgcgc acatttcccc gaaaagtgcc    8880
acctgacgt                                                            8889
```